(12) United States Patent
Horvitz et al.

(10) Patent No.: US 6,465,617 B1
(45) Date of Patent: Oct. 15, 2002

(54) IDENTIFICATION AND CHARACTERIZATION OF A GENE WHICH PROTECTS CELLS FROM PROGRAMMED CELL DEATH AND USES THEREFOR

(75) Inventors: H. Robert Horvitz, Cambridge; Michael Hengartner, Boston, both of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/233,527

(22) Filed: Jan. 20, 1999

Related U.S. Application Data

(60) Division of application No. 08/801,248, filed on Feb. 19, 1997, now abandoned, which is a continuation of application No. 08/288,295, filed on Aug. 10, 1994, now abandoned, which is a division of application No. 07/927,681, filed on Aug. 10, 1992, now abandoned, which is a continuation-in-part of application No. 07/898,933, filed on Jun. 12, 1992, now abandoned.

(51) Int. Cl.[7] .......................... C07K 1/00; C07K 14/00; C07K 17/00; C07H 21/02; C07H 21/04

(52) U.S. Cl. .................... 530/350; 536/23.1; 536/23.5

(58) Field of Search .................. 530/350; 536/23.1, 536/23.5

(56) References Cited

U.S. PATENT DOCUMENTS

| | | | |
|---|---|---|---|
| 5,196,133 A | | 3/1993 | Chalfie et al. .............. 435/325 |
| 5,523,393 A | * | 6/1996 | Tsujimoto et al. |

FOREIGN PATENT DOCUMENTS

| | | |
|---|---|---|
| EP | 0252 685 | 1/1988 |
| EP | WO 9 300 909 | 1/1993 |

OTHER PUBLICATIONS

J.U. Bowie et al., Science, vol. 247, Mar. 1990, pp. 1306–1310*
E. Lazar et al., Molecular and Cellular Biology, vol. 8, No. 3, Mar. 1988, pp. 1247–1252.*
W.H. Burgess et al., Journal of Cell Biology, vol. 111, Nov. 1990, pp. 2129–2138.*
Cazals–Hatem et al., "Molecular Cloning and DNA Sequence Analysis of cDNA Encoding Chicken Homologue of the Bcl–2 Oncoprotein", Biochimica et Biophysica Acta 1132:109–113 (1992).
Cleary et al., "Cloning and Structural Analysis of cDNAs for bcl–2 and a Hybrid bcl–2/Immunoglobulin Transcript Resulting from the t(14;18) Translocation", Cell 47:19–28 (1986).
Clem et al., "Prevention of Apoptosis by a Baculovirus Gene During Infection of Insect Cells", Science 254:1388–1390 (1991).

Coulson et al., "Genome Linking with Yeast Artificial Chromosomes" Nature 335:184–186 (1988).
Desai et al., Nature 336:638–646 (1988).
Eguchi et al., "Isolation and Characterization of the Chicken bcl–2 Gene: Expression in a Variety of Tissues Including Lymphoid and Neuronal Organs in Adult and Embryo", Nucleic Acids Res. 20(16):4187–4192 (1992).
Ellis et al., Development 112:591–603 (1991).
Ellis et al., "Mechanisms and Functions of Cell death", Annu. Rev. Cell Biol. 7:663–698 (1991).
Gregory et al., "Activation of Epstein–Barr Virus Latent Genes Protects Human B Cells from Death by Apoptosis", Nature 349:612–614 (1991).
Henderson et al., "Induction of bcl–2 Expression by Epstein– Barr Virus Latent Membrane Protein 1 Protects Infected B Cells from Programmed Cell death", Cell 65:1107–1115 (1991).
Hengartner et al., "Caenorhabditis elegans gene ced–9 Protects Cells from Programmed Cell Death", Nature 356:494–499 (1992).
Hockenbery et al., "Bcl–2 is an inner mitochondrial membrane protein that blocks programmed cell death," Nature 348:334–336 (1990).
Horvitz and Chalfie, "Implications of Nematode Neuronal Cell Death for Human Neurological Disorders", in Neurodegenerative Disorders: Mech. & Pros. for Therapy, Price et al., (eds.), Wiley & Sons, 1991, pp. 5–19.
Negrini et al., "Molecular Analysis of mbcl–2: Structure and Expression of the Murine Gene Homologous to the Human Gene Involved in Follicular Lymphoma", Cell 49:455–463 (1987).

(List continued on next page.)

*Primary Examiner*—Deborah Crouch
*Assistant Examiner*—Peter Paras, Jr.
(74) *Attorney, Agent, or Firm*—Clark & Elbing LLP; Kristina Bieker-Brady

(57) ABSTRACT

The present invention relates to genes, referred to herein as cell death-protective genes, which protect cells against programmed cell death by antagonizing the activities of genes which cause cell death. As described herein, a cell death-protective gene from the nematode *Caenorhabditis elegans*, called ced-9, has been identified, sequenced, and characterized. ced-9 is essential for *C. elegans* development and apparently functions by protecting cells which normally live during development from programmed cell death. Mutations which constitutively activate and inactivate the ced-9 gene are also described. ced-9 was shown to function by antagonizing the activities of the cell death genes, ced-3 and ced-4. As further described, the protein product of the human oncogene bcl-2 was found to have a similar sequence to the ced-9 protein. Methods and agents for both increasing and decreasing the occurrence of cell death are described that are potentially useful for diagnosis, prevention and therapy of diseases and conditions involving cell death; for the treatment of viral, parasitic, and other types of infection; and for killing organisms that are detrimental or potentially detrimental to the environment or to humans, pets, livestock, or agriculture.

4 Claims, 22 Drawing Sheets

OTHER PUBLICATIONS

Sentman et al., Bcl–2 inhibits Multiple Forms of Apoptosis but not Negative Selectrion in Thymocytes Cell 67:879–888 (1991).

Seto et al., "Alternative Promoters and Exons, Somatic Mutation and Deregulation of the Bci–2–1g Fusion Gene in Lymphoma", The EMBO Journal 7:123–131 (1988).

Strasser et al., "bcl–2 Transgene Inhibits T Cell Death and Perturbs Thymic Self–Censorship", Cell 67:889=899 (1991).

Tsujimoto & Croce, "Analysis of the Structure, Transcripts, and Protein Products of bcl–2, the Gene Involved in Human Follicular Lymphoma", Proc. Natl. Acad. Sci. USA, 83:5214–5218 (1986).

Tsujimoto et al., "Cloning of the Chromosome Breakpoint of Neoplastic B Cells with the t(14;18) Chromosome Translocation", Science 226:1097–1099 (1984).

Vaux et al., "Prevention of Programmed Cell Death in Caenorhaboditis elegans by Human Bcl–2" Science 258:1955–1957 (1992).

Vaux et al., "Bcl–2 Gene Promotes Haemopoietic Cell Survival and Cooperates with c–myc to immortalize pre–B Cells", Nature 335:440–442 (1988).

* cited by examiner

```
              10         20         30         40         50         60         70         80         90        100
     1234567890 1234567890 1234567890 1234567890 1234567890 1234567890 1234567890 1234567890 1234567890 1234567890

XhoI
      ClaI                                   SpeI NcoI                                 PaeR7I
       ▼                                       ▼  ▼                                      ▼
     ATCGATAGTC GTCACCAAAT GGATTTTCCG ATTTCTCACT AGTCCATGGC TCACAATTTA CAAAATCTCG AGAAAAGAAA GGATGCAAGG AGTATGAAGA  100

SspI       DraI         BstBI
                         ▼          ▼            ▼
     GGTTCCGAAT CTAAATATTT TAATTTAAAA AAATCAATTT CGAATTGAAA TTCAACTCCT ACTCGTTTTG AAAATGCCAA TCCTTTAAGT AAACTTCTGG  200

BstBI
                                                                                      ▼
     ATCGCCCATT TCTTCCAGAA ATTCCTTCAA AGTAGTGGTT TTGTACTGAT TTCCTCCGCA AAGAATAGGA ACTTTCGAAT CTCCTGGAGC GAAACGGGAT  300

SspI
                                            ▼
     TTTSATAACA AAAAACTATC CAGACAAACC ATAGGACTTT TTCAAATATT CCTTATTTGG CTGTCCATTT GGAAGCACCC AATCTTTAAC GCTGTCCAGC  400

NcoI
                                                                                  ▼
     CAGAAGTGCT CCACTCGCCA AGGATAAAAG GCTCATTTTT GAAGCCGAAT TTTACTAAAA TCTCTAGCCA TGGAGTCGAT GGATCAGAAA TTCGAGGAAT  500

TTTAGATTTC ATCTTGAAAT TTGCAATGGA AAAAATAATT ATTCAAAGAA AATCACAGAA AATGCAACAA AAAAAACAAA AAAAGAACAA AAAACAAGTC  600

SmaI
           XmaI
           ▼▼
     GAAAAGTGCG CCCGGGTCGT TTGCTGACGC ATCTCTTCAA ACGAGACGCG CTGCTGGCGA CTTCTCGTGC CCTGTGCGTG CATTTCCGCA ACAAAATTCA  700

ACACTTGTTT TGAAACGCAC CGCCCTGTTT CTTTTTTCAA TTTTGATAAG AAAATCAGCA TTGTTTCAGG ATGATTAACA TTCCAACTGC GATTCTGTGC  800
```

PvuI
         NarI                               ClaI
          ▼                                  ▽  ▼
CGCTTGGGCG CCAGATCGTC GATTTCCCGC TCCTTTGGAA CATCGATCGT CACCAAGGTG GGGATTTTTT GAATTTTTCC GTGAAAATTG TTGATTTTTT  900

AseI       SspI
                                         ▼          ▼
GTGTACGCAT GAAGGAGAAA TGTATAACAG ACACATTCTT TTCAATTAAT TATTTATAAT ATTCACAGTC CGAGGCAAAG ACGCCAATCC AGAAGTTCGG 1000

Eco47III                                                             BspMII
                        ▼                                                                   ▼
ATGGGAATAC CTGTTGAAGC AGCGCTCCAA GAATCGCCCA ATCGCTCCAC ATCTCACCGT CTACCAGCCA CAATTGACCT GGATGCTCTC CGGATTCCAT 1100

AGAATCAGCG GTTGTGTAAT GGCCGGAACC CTTCTCGTCG GAGGAATCGG ATTCGCAGTT TTGCCGTTCG ATTTCACCGC TTTTGTGGAT TTCATCCGTA 1200

EcoRI
                                                                                     ▼
GCTGGAACTT ACCATGCSSG GTGACCGCTG TCTTCAAGTA CATCATTGCT TTCCCCATCA TTTTCCATAC TCTTAACGGA ATTCGCTTCT TAGGATTCGA 1300

AseI      DraI      AseI   BglII
                                                  ▼         ▼         ▼      ▼
TTTGGCTAAG GGAGTCAATA ATGTTGGACA GGTAGGAGTT GAAATTATTA ATTTAATTGT TTTAAAATAA AAATTAATTT TCAGATCTAC AAATCGGGAT 1400

EcoRV                                                                   AvrII
▼                                                                         ▼
ATCTCGTATC TGGACTTTCG GCTATTCTTG CTCTCGCCAT TGTCTTCAAC TCTTGCCAGA ACAAGAGCAA CAAGACTGCC TAGGCACAGA TGCTCCGCCT 1500

TCTTTTTTCT TACTCCGCCC CAGCCCTCGA CAATTCTCGT CAATTTACTT TTACCGTTGA TTTCTTCGAT TTTCTCTCTT TTCCGTAGAT TTACCTCTCC 1600
```

```
                     XbaI
                     ▼
TCTTCGTTTT TTTTTCTCTG TCTAGAATGT ATATTATGAT TATGAAAACG AATAAAAATT TTAGATGACA CGCTGCACGG CGGACAACTC GCTGACGAAT  1700

CCGGCGTATC GGCGACGAAC GATGGCGACT GGCGAGATGA AGGAGTTTCT GGGGATAAAA GGCACAGAGC CCACCGATTT TGGAATCAAT AGTGATGCTC  1800

AGGACTTGCC ATCACCGAGT AGGCAGGCTT CGACGCGAAG AATGTCCATC GGAGAGTCAA TTGATGGAAA AATCAATGAT TGGGAAGAGC CAAGGCTTGA  1900

EcoRV                                                                   SalI
▼                                                                       ▼
TATCGAGGGA TTTGTGGTAA TTTTTTAATT TTTTTTTGTA AATAAAATTT CCTGCTGCTT CCAGGTCGAC TATTTCACGC ACCGAATCCG GCAAAACGGA  2000

ATGGAATGGT TTGGAGCACC GGGATTGCCG TGTGGAGTGC AACCGGAGCA CGAAATGATG CGAGTTATGG GAACGATATT CGAGAAGAAG CACGCGGAAA  2100

PvuII
                     ▼
ATTTTGAGAC CTTCTGTGAG CAGCTGCTCG CAGTGCCCAG AATCTCATTT TCACTGTATC AGGATGTGGT TCGGACGGTT GGAAATGCAC AGACAGATCA  2200

BstBI
                                                                        ▼
ATGTCCAATG TCTTATGGAC GTTTGGTAAG GGAGAAAATA CTGAAAAAAA GTTTGCAAAA ATTCGAAAAT TCGCCAGAAA GGTGGCAGAA AAAACATTTG  2300

CAAAAATTGT TGTTTTCCT TCAGGAAATC AGCAAAACTT GGTCAAAAAT AGCCCAATTA TGTGTCTTTT TTGAAAGTTT TCCATTAAAA AACCACGAAT  2400
```

SspI
                                                    EcoRI                           BstBI      DraI
                                                      ▼                               ▼    ▼   ▼
TTTGATCCCG GATTGTAATT TTTTTTGTTG ATAAATTAGC AGAAAACTTT ACGAATTCGA TTAAAAACGT TATTTTCTAT TCGAATATTT TTAAAGCATA  2500

BglII                                    DraI
                      ▼                                        ▼
TTTTCCTTGA TTTGTATTTG CGAAAAAGAT CTGCTGATTT ATCAAAAATC GGTTTTTAAA TGTAAAATTT GTGGAAAATA CATTAAAATT CGATTTTTGA  2600

BstBI                                              BstBI
           ▼                                                  ▼
ACTTTTTTCT TCGAAAAACA GGTTTTTCTG CTGATTTGCT GAACGAAAAA CCCCAAAAAT TCAATTTTCG AACATTAAAA ACCAGAAAAA TCGTTTTTTT  2700

HindIII
▼
AAGCTTAATT TTCCGCCAGA AATGAACGAA TTAAATTGCA AATTTCTAAT TTTCAGATAG GTCTAATCTC GTTCGGCGGT TTCGTAGCTG CAAAAATGAT  2800

PstI                                        BamHI
                ▼                                           ▼
GGAATCCGTG GAACTGCAGG GACAAGTGCG AAACCTCTTC GTTTACACAT CGCTGTTCAT CAAAACGCGG ATCCGCAACA ACTGGAAGGA ACACAATCGG  2900

SmaI
                                                        XmaI
                                                        ▼▼
AGCTGGGTAA GGAGTATTTG CATAGACATT AGAAGTCAAT ATCCCCCTTT CCCTAGTACC CTTGACTTCC CGGGGTGTTG GTAAGCCGAT AATTACAGGG  3000

PvuII                                                                          BsmI
                            ▼                                                                              ▼
TTCGGTAGCC TCTTGGGGGG ACAGCTGGAA ACATATTCAA GTATATTACT GTTTATGATA ATGTTATTGT TACGGGAATA CAAAATTCGC AGAATGCTAT  3100

DraI    DraI
                                                        ▼       ▼
TTCACAACAT ATTTGACGCG CAAAATATCC AGTAGAGAAA ACTACAGTAA TTCTTTAAAT TTTTAAAATT TTTACAATTA AAGAAAATAA CCACTAATCA  3200
```

AseI                                         DraI
      ▼                                            ▼
AAAGAAATTA ATTTCAAAAA TCGAGCCCGT AAATCGACTA CAGTAGGCAT TTAAAGAATT ACTGTAGTTT TCGCTACGAG ATATTCCGC CTCAAATATG  3300

BsmI
           ▼
TTGTGAAATA CGCATTCACG GATTTTTGTG TTCCCCGGAA TATGCTCTAA AGCATTATTT GTGAAAATAA AAAATCAAGA AAAAAATTGC AGGACGACTT  3400

BspHI
▼
CATGACACTC GGAAAACAAA TGAAAGAGGA CTACGAACGA GCAGAAGCTG AAAAAGTGGG ACGCCGGAAG CAGAACAGAC GGTGGTCGAT GATTGGCGCT  3500

PvuII                                                                              AseI
           ▼                                                                                  ▼
GGAGTAACAG CTGGAGCCAT TGGAATCGTT GGAGTCGTCG TGTGTGGGCG GATGATGTTC AGCTTGAAGT AACGTATTCA ATTTGTGTAA ATAATTAATT  3600

TATGTACAAC TCCTTACATT TGAATCTCAT TTTTGCTCAC TGATTCTCTC ATCCTTTGAA CTGGAAGAAG TGGGAAAGCT AGGCCACAAA TTACGGCTCT  3700

BalI
                                                              ▼
CTGTGTCGAT TTACGATTTT ACTGCAATTT TTTCCGATTG CCTTTTTTTT TGGCCAAACC CTACTTCCGC GTAATATCAA CTTTTCCGTG TTCTGTACAT  3800

TTCGTCAAAA ACCCTGAAAC CCTAACTTTT CTCGCCGTGG CCTAGCCTCC CGCTTCTCTT CCACATTTCC AAAGTACCCC TGTATCTCAA TAATTCATCT  3900

SplI
                                                             MluI
                                                             ▼▼
TCACTTTAAC TGTCTCTTTT CGTGTGGCCT CTTCCAACTC CCCCCAAATT CCTGTACGCG TACGCGACTT TGTATTTATT TTTTCAAAT TGTTTTCTCT  4000
```

FspI
                                                                                               ▼
CTACAACAAC AAAAAAAACG GTTCTTTTAT TCAACCCTTT TTTCGGAACG AAACTGCAAT TTTGATAATA GGCGTGCGCA AGAGAATCCG GTTTTCATTT  4100

XhoI
                                                                                     PaeR7I
                                                                                      ▼
TCGCCATCAC GTCATCCAAA AAAGTTTAGT AGGAAAATAT CATTTTTTAA TATAATGATT CATCTTTCTC GCCTCTTCTG TCTCGAGACG ACGGTCAATT  4200

BstBI
             ▼
CGATGGCCTT GAATTTTTCG AAAACAAAAA TGTTTTTGTT TAGTGTAAAC GATCCCCCCG CCTTATCGCT GTTTCACCAT CAGATAGGCT CCGCCATTTG  4300

ApaLI
                                                        ▼
ATTCCCTTGA ATTTTGTCGG TATATAAAAC AAAAAACGTT AGTGCACGAT TCAAAAAACA ACAATGCGTG CTTTACTATT CACCTCTGTT GTTCTTTTGG  4400

EcoRI
                                                                                    ▼
CTTTGGCTTT TGTTGAGGCA AGAAGCAGA CTATCACTGT CAAGGGTACA ACTATTTGTA ATAAGAAGAG AATTCAGGMG RAGGTTACCT TTGGGAGAAA  4500

StuI
                                                                         ▼
GATACTCGTG AGTTTTCAGT CTTGTTTAGC TTGAAACGGC TTAAAAAGGA CTAAAAAGGC CTAAAAATTG AAGTTTTCCA CCTGTTTTCA AAAGAAAGCC  4600

GAATTGCACA GCTTTACACG AGATTTCTCA ATAATTTGTA TTTGAAATTT TCATATTCAT CCCCAAACGT TCTTTACACG AAATTTTGCG ATTTTTGAGC  4700

DraI
                                                                  ▼
TTAAAATACG ATACCTGGTC TCGACACGAA ACATTTTTGT TAAATTCAAA AAGATGTGCG CCTTTAAAGA GTGCTGTAGT TTGAAACTTC TGTTGTTGCG  4800
```

ClaI                                                                        NruI
           ▼                                                                           ▼
GACTTTTCAT CGATTTTTCG TAGCGTTTTT TTATAAGAAA AATGTATTTA TTTATTCAAA AATTTAATTT TACCGAATCG CGAAAAACAA AATGAAGAAC  4900
                                                        SacI
                                                        ApaI
                                                        FspI
                                                        BalI
                                                        BclI                                            SmaI
                         ScaI                  NarI                                             XmaI
                         ▼                     ▼▼                                               ▼▼
ACCGATAAAA ATATCGCAGC AACAATAGTT TGAAATTACA GTACTCTTTT AAGGNGNNCA CATTTCCTAT ATTTCACACA AACTTGTCGT GTCGNNNCNG  5000

HindIII
                                                                   ▼
GGTATCGTCA TTTTGATGCA GAAATCAAGA AAATTGCATA TATGTTCAAA AAACCACAAT TATGGCGAAT TTCAAGCTTG AAACGAAAAT TCAGGAAATT  5100

BstBI                     NdeI
           ▼                         ▼
CTAAAAATTA AAAAAAAATC ATTCGAAATG TGAAATTTGA TATTCAACTT GAAGTCCATA TGGCAAATTT CGTCTATTCC GNNNTTCGAN NATTTTGTTC  5200

CACGTGGCCG CGAAAAGAGA AAGCACGANN ACTGATTTCT GGCAATTTTT TCCTGTACCG TGTCAATTAT TTGAAACTCT AATAAGCTGG TATTTTCTG  5300

SspI
                                      ▼
CTATTGACAA CTAACTGAAT CCATAATTTG CAATTATAAT ATTGACTTTT GATGTGTGGC TTAGAAAAAA AAAACCAAAA ACCTCATCTA GCTTTAGGCT  5400

AvrII                                                                               SalI
          ▼                                                                                   ▼
GCCAATATAT TCCTAGGACA TATAAAAAAC CCTTAAAATT CTCTGCAACA CCTACAAGCT ATCAAACGTA CTATTAGTAT TCAATTTTCC AGTCGACCCC  5500

BamHI
                                                    ▼
GATGACAAGC TCGCCTCAAT GCAATCGAAC AAAGAAGGAG AGTTCTCACT TACCGGATCC GACGACGAGA TCACCTCAAT CTCTCCATAC CTCATAATCA  5600
```

CCCACAACTG CAACGTGAAG AAGGCCGGAT GCAAGCGTGT TTCAGAGTAT TTGATTCCAA AGGAGAAGAT CGGTGGAACC TATGATATGA CATACGTCAC  5700

TCTTGATATT CTTTCCGCTA AAGACAAGGA GAAGTGCTAA GAAAATGTTT TTTTTGTTTG GTTTGCTTGT TTGGAAGGGA AGGACTTTCT ATCTCTTTTA  5800

ATTCAACAAT AAACTATTGG AAAACCGTTG AAATTTTAAC CTTGAACTGT AAGAAAAGTT GCGTGATTAT GTTGACAATT TTGCCAAGTA TATCTTTGTG  5900

BsmI
  EcoRV                  SspI                 AseI              FspI
   ▼                      ▼                    ▼                 ▼
GATATCACAA TAAACGAAGT CAAAGCACGA AATATTACGG AAACACAAAA TTAATGAGAA TGCGCAACAT ATTTGACCGC AAAATATCTC GTAGCGAAAC  6000

Eco47III         SacI                                                   SspI
                              ▼                ▼                                                     ▼
TACAGTAATT CTTCAAAAGA CTACTGTAGC GCTGTGTCGA TTTACGAGCT CGATTTTTGA AATGAATCAG ACTAGAAGAA AAGGAGGAAA ATATTGAACA  6100

TCAATTGAAC ATCAATTCAA AAAGTCGAAC CCTTGACTAC AGTAGTCTTC TAAAGAATTA CTGTAGTTTT CGCTACGAGA TATTTTGNGN GTCAAATATG  6200

FspI                                                                                                PstI
   ▼                                                                                                   ▼
TTGNGCAATA CGCATCCTCA GAATTGTGTG TTCTCGTAAT GTCTTGAAAA TTTTCCATTT CAACATCAAA TAAGCAAATC TAAAAATGTG GGTTCTGCAG  6300

DraI                                      NheI
                                                           ▼                                         ▼
CGACCACTAT GACTGTGATC GTGGCAAGAC CCACTCAGAA AACTACGTGT TCCTTTAAAC AAATACATTT TTAAGTATTG TAGGTATAAA AATTGTTGGC  6400
```

SalI                                                                HindIII
                         ▼                                                                     ▼
TAGCAGTCTA GGCTGCCTTT TTCAGTCGAC AAACTTCTAA TTTAATCGGC GGGTCTTCAA AAAGTCGTTT CTTTGAAAAT ATAAAGCTTT ATATATTTAT  6500

EcoRV    SpeI
                    ▼       ▼
ATATTAAAAA TTTTGATTAC ATGATATCAA AAGCGACTAG TTTGTATAAA AATTATCAA                                             6559
```

TTTGAGATGA CACGCTGCAC GGCGGACAAC TCGCTGACGA ATCCGGCGTA TCGGCGACGA ACGATGGCGA CTGGCGAGAT GAAGGAGTTT CTGGGGATAA  100
      MetT hrArgCysTh rAlaAspAsn SerLeuThrA snProAlaTy rArgArgArg ThrMetAlaT hrGlyGluMe tLysGluPhe LeuGlyIleL

AAGGCACAGA GCCCACCGAT TTTGAATCA  ATAGTGATGC TCAGGACTTG CCATCACCGA GTAGGCAGGC TTCGACGCGA AGAATGTCCA TCGGAGAGTC  200
ysGlyThrGl uProThrAsp PheGlyIleA snSerAspAl aGlnAspLeu ProSerProS erArgGlnAl aSerThrArg ArgMetSerI leGlyGluSe
                                                               EcoRV              SalI
                                                                 ▼                 ▼
AATTGATGGA AAAATCAATG ATTGGGAAGA GCCAAGGCTT GATATCGAGG GATTTGTGGT CGACTATTTC ACGCACCGAA TCCGGCAAAA CGGAATGGAA  300
rIleAspGly LysIleAsnA spTrpGluGl uProArgLeu AspIleGluG lyPheValVa lAspTyrPhe ThrHisArgI leArgGlnAs nGlyMetGlu

TGGTTTGGAG CACCGGGATT GCCGTGTGGA GTGCAACCGG AGCACGAAAT GATGCGAGTT ATGGGAACGA TATTCGAGAA GAAGCACGCG GAAAATTTTG  400
TrpPheGlyA laProGlyLe uProCysGly ValGlnProG luHisGluMe tMetArgVal MetGlyThrI lePheGluLy sLysHisAla GluAsnPheG
                      PvuII
                        ▼
AGACCTTCTG TGAGCAGCTG CTCGCAGTGC CCAGAATCTC ATTTTCACTG TATCAGGATG TGGTTCGGAC GGTTGGAAAT GCACAGACAG ATCAATGTCC  500
luThrPheCy sGluGlnLeu LeuAlaValP roArgIleSe rPheSerLeu TyrGlnAspV alValArgTh rValGlyAsn AlaGlnThrA spGlnCysPr
                                                                                                   PstI
                                                                                                    ▼
AATGTCTTAT GGACGTTTGA TAGGTCTAAT CTCGTTCGGC GGTTTCGTAG CTGCAAAAAT GATGGAATCC GTGGAACTGC AGGGACAAGT GCGAAACCTC  600
oMetSerTyr GlyArgLeuI leGlyLeuIl eSerPheGly GlyPheValA laAlaLysMe tMetGluSer ValGluLeuG lnGlyGlnVa lArgAsnLeu
                      BamHI                                                  BspHI
                        ▼                                                      ▼
TTCGTTTACA CATCGCTGTT CATCAAAACG CGGATCCGCA ACAACTGGAA GGAACACAAT CGGAGCTGGG ACGACTTCAT GACACTCGGA AAACAAATGA  700
PheValTyrT hrSerLeuPh eIleLysThr ArgIleArgA snAsnTrpLy sGluHisAsn ArgSerTrpA spAspPheMe tThrLeuGly LysGlnMetL
                                                                                                   PvuII
                                                                                                     ▼
AAGAGGACTA CGAACGAGCA GAAGCTGAAA AAGTGGGACG CCGGAAGCAG AACAGACGGT GGTCGATGAT TGGCGCTGGA GTAACAGCTG GAGCCATTGG  800
ysGluAspTy rGluArgAla GluAlaGluL ysValGlyAr gArgLysGln AsnArgArgT rpSerMetIl eGlyAlaGly ValThrAlaG lyAlaIleGl
                                                                                     AseI
                                                                                       ▼
AATCGTTGGA GTCGTCGTGT GTGGCGGAT  GATGTTCAGC TTGAAGTAAC GTATTCAATT TGTGTAAATA ATTAATTTAT GTACAACTCC TTACATTTGA  900
yIleValGly ValValValC ysGlyArgMe tMetPheSer LeuLys...

ATCTCATTTT KGCTCACTGA TTCTCTCATC CTTTGAACTG GAAGAAGTGG GAAAGCTAGG CCACAAATTA CGGCTCTCTG TGTCGATTTA CGATTTTACT 1000
                  BalI
                   ▼
GCAATTTTTT CCGATTGCCT TTTTTTTGG  CCAAACCCTA CTTCCGCGTA ATATCAACTT TTCCGTGTTC TGTACATTTC GTCAAAAACC CTGAAACCCT 1100

AACTTTTCTC GCCGTGGCCT AGCCTCCCGC TTCTCTTCCA CATTTCCAAA GTACCCCTGT ATCTCAATAA TTCATCTTCA CTTTAACTGT CTCTTTTCGT 1200
                                                   SplI
                                                   MluI
                                                   ▼ ▼
GTGGCCTCTT CCAACTCCCC CCAAATTCCT GTACGCGTAC GCGACTTTGT ATTTATTTTT TTCAAATTGT TTTCTCTCTA CAACAACAAA AAAAACGGTT 1300

CAAAAAAAAA AAAAA                                                                                            1315
```

MTRCTADNSL TNPAYRRRTM ATGEMKEFLG IKGTEPTDFG INSDAQDLPS  50

PSRQASTRRM SIGESIDGKI NDWEEPRLDI EGFVVDYFTH RIRQNGMEWF 100

GAPGLPCGVQ PEHEMMRVMG TTFEKKHAEN FETFCEQLLA VPRISFSLYQ 150

DVVRTVGNAQ TDQCPMSYGR LIGLISFGGF VAAKMMESVE LQGQVRNLFV 200

YTSLFIKTRI RNNWKEHNRS WDDFMTLGKQ MKEDYERAEA EKVGRRKQNR 250

RWSMIGAGVT AGAIGIVGVV VCGRMMFSLK                      280
```

Fig. 4

MTRCTADNSL TNPAYRRRTM ATGEMKEFLG IKGTEPTDFG INSDAQDLPS 50

PSRQASTRRM SIGESIDGKI NDWEEPRLDI EGFVVDYFTH RIRQNGMEWF 100
              n1653ts (TAT -> AAT) N 

GAPGLPCGVQ PEHEMMRVMG TIFEKKHAEN FETFCEQLLA VPRISFSLYQ 150
     E (GGA -> GAA) n1950 

DVVRTVGNAQ TDQCPMSYGR LIGLISFGGF VAAKMMESVE LQGQVRNLFV 200
STOP (CAG -> TAG) n2077
YTSLFIKTRI RNNWKEHNRS WDDFMTLGKQ MKEDYERAEA EKVGRRKQNR 250

RWSMIGAGVT AGAIGIVGVV VCGRMMFSLK           280

Fig. 5

```
                Gap Weight:  3.000     Average Match:   0.540
             Length Weight:  0.100     Average Mismatch: -0.396

Quality:  89.8             Length:    298
                     Ratio:  0.376              Gaps:     11
         Percent Similarity: 47.059     Percent Identity: 23.077

1  ...MTRCTADN..........SLTNPAYRRRTMATGEMKEFLGIKGTEPT   37
        .|.. ||            .|...:| :   ..|::. .  :..|.
  1  MAHAGRTGYDNREIVMKYIHYKLSQRGYEW...DAGDVGAAPPGAAPAPG   47

38  DFGINSDAQDLPSPSRQASTRRMSIGESIDGKINDWEEPRLDIEGFVVDY   87
     |: ...:   .  |.:||::  .|    .:.... ..  .
 48  IFSSQPGHTPHPAASRDPVARTSPLQTPAAPGAA.................  81

88  FTHRIRQNGMEWFGAPGLPCGVQPEHEMMRVMGTIFEKKHAKNFETFCEQ  137
       ::|:|......  |  :|  |. |.::.  :|..::.|
 82  ..............AGPALSPVPPVVHLALRQAGDDFSRRYRGDFAEMSSQ  118

138  LLAVPRISFSLYQDVVRTVGNAQTDQCPMSY[GR]LIGLISFGGFVAAKMME  187
     | .|  .. :  :... ||  .: ..       .:::|||::::.|||.:.   :|
119  LHLTPFTARGRFATVVEELFRD.....GVNW[GR]IVAFFEFGGVMC...VE  160
  conserved residue mutated in n1950 →

188  SV..ELQGQVRNLFVYTSLFIKTRIRNNWKEHNRSWDDFMTL.GKQMKE.  233
     ||  |: . | |: ::. ::. :: :.|  :.|  :||.|:.|  |. |:.
161  SVNREMSPLVDNIALWMTEYLNRHL.HTWIQDNGGWDAFVELYGPSMRPL  209

234  .DYERAEAEKVGRRKQNRRWSMIGAGVTAGAIGIVGVVVCGRMMFSLK   280
      |:.: . ...:        .:.::||.:|  ||.           :||  |
210  FDFSWLSLKTL......LSLALVGACITLGAY............LSHK   239
```

Fig. 6

```
  1 GCGCCCGCCC CTCCGCGCCG CCTGCCCGCC CGCCCGCCGC GCTCCCGCCC
 51 GCCGCTCTCC GTGGCCCCGC CGCGCTGCCG CCGCCGCCGC TGCCAGCGAA
101 GGTGCCGGGG CTCCGGGCCC TCCCTGCCGG CGGCCGTCAG CGCTCGGAGC
151 GAACTGCGCG ACGGGAGGTC CGGGAGGCGA CCGTAGTCGC GCCGCCGCGC
201 AGGACCAGGA GGAGGAGAAA GGGTGCGCAG CCCGGAGGCG GGGTGCGCCG
251 GTGGGGTGCA GCGGAAGAGG GGGTCCAGGG GGGAGAACTT CGTAGCAGTC
301 ATCCTTTTTA GGAAAAGAGG GAAAAAATAA AACCCTCCCC CACCACCTCC
351 TTCTCCCCAC CCCTCGCCGC ACCACACACA GCGCGGGCTT CTAGCGCTCG
401 GCACCGGCGG GCCAGGCGCG TCCTGCCTTC ATTTATCCAG CAGCTTTTCG
451 GAAAATGCAT TGCTGTTCG GAGTTTAATC AGAAGACGAT TCCTGCCTCC
```

Fig. 7-1

```
 501 GTCCCCGGCT CCTTCATCGT CCCATCTCCC CTGTCTCTCT CCTGGGGAGG
 551 CGTGAAGCGG TCCCGTGGAT AGAGATTCAT GCCTGTGTCC GCGCGTGTGT
 601 GCGCGCGTAT AAATTGCCGA GAAGGGGAAA ACATCACAGG ACTTCTGCGA
 651 ATACCGGACT GAAAATTGTA ATTCATCTGC CGCCGCCGCT GCCAAAAAAA
 701 AACTCGAGCT CTTGAGATCT CCGGTTGGGA TTCCTGCGGA TTGACATTTC
 751 TGTGAAGCAG AAGTCTGGGA ATCGATCTGG AAATCCTCCT AATTTTTACT
 801 CCCTCTCCCC CCGACTCCTG ATTCATTGGG AAGTTTCAAA TCAGCTATAA
 851 CTGGAGAGTG CTGAAGATTG ATGGGATCGT TGCCTTATGC ATTTGTTTTG
 901 GTTTTACAAA AAGGAAACTT GACAGAGGAT CATGCTGTAC TTAAAAAATA
 951 CAAGTAAGTC TCGCACAGGA AATTGGTTTA ATGTAACTTT CAATGGAAAC
1001 CTTTGAGATT TTTTACTTAA AGTGCATTCG AGTAAATTTA ATTTCCAGGC
1051 AGCTTAATAC ATTGTTTTTA GCCGTGTTAC TTGTAGTGTG TATGCCCTGC
1101 TTTCACTCAG TGTGTACAGG GAAACGCACC TGATTTTTTA CTTATTAGTT
1151 TGTTTTTTCT TTAACCTTTC AGCATCACAG AGGAAGTAGA CTGATATTAA
1201 CAATACTTAC TAATAATAAC GTGCCTCATG AAATAAAGAT CCGAAAGGAA
1251 TTGGAATAAA AATTTCCTGC GTCTCATGCC AAGAGGGAAA CACCAGAATC
1301 AAGTGTTCCG CGTGATTGAA GACACCCCCT CGTCCAAGAA TGCAAAGCAC
1351 ATCCAATAAA ATAGCTGGAT TATAACTCCT CTTCTTTCTC TGGGGGCCGT
1401 GGGGTGGGAG CTGGGGCGAG AGGTGCCGTT GGCCCCCGTT GCTTTTCCTC
1451 TGGGAAGGAT GGCGCACGCT GGGAGAACGG GGTACGACAA CCGGGAGATA
1501 GTGATGAAGT ACATCCATTA TAAGCTGTCG CAGAGGGGCT ACGAGTGGGA
1551 TGCGGGAGAT GTGGGCGCCG CGCCCCGGG GGCCGCCCCC GCACCGGGCA
1601 TCTTCTCCTC CCAGCCCGGG CACACGCCCC ATCCAGCCGC ATCCCGCGAC
1651 CCGGTCGCCA GGACCTCGCC GCTGCAGACC CCGGCTGCCC CCGGCGCCGC
1701 CGCGGGGCCT GCGCTCAGCC CGGTGCCACC TGTGGTCCAC CTGGCCCTCC
1751 GCCAAGCCGG CGACGACTTC TCCCGCCGCT ACCGCGGCGA CTTCGCCGAG
1801 ATGTCCAGCC AGCTGCACCT GACGCCCTTC ACCGCGCGGG GACGCTTTGC
1851 CACGGTGGTG GAGGAGCTCT TCAGGGACGG GGTGAACTGG GGGAGGATTG
1901 TGGCCTTCTT TGAGTTCGGT GGGGTCATGT GTGTGGAGAG CGTCAACCGG
```

Fig. 7-2

1951 GAGATGTCGC CCCTGGTGGA CAACATCGCC CTGTGGATGA CTGAGTACCT
2001 GAACCGGCAC CTGCACACCT GGATCCAGGA TAACGGAGGC TGGGATGCCT
2051 TTGTGGAACT GTACGGCCCC AGCATGCGGC CTCTGTTTGA TTTCTCCTGG
2101 CTGTCTCTGA AGACTCTGCT CAGTTTGGCC CTGGTGGGAG CTTGCATCAC
2151 CCTGGGTGCC TATCTGAGCC ACAAGTGAAG TCAACATGCC TGCCCCAAAC
2201 AAATATGCAA AAGGTTCACT AAAGCAGTAG AAATAATATG CATTGTCAGT
2251 GATGTACCAT GAAACAAAGC TGCAGGCTGT TTAAGAAAAA ATAACACACA
2301 TATAAACATC ACACACACAG ACAGACACAC ACACACACAA CAATTAACAG
2351 TCTTCAGGCA AAACGTCGAA TCAGCTATTT ACTGCCAAAG GGAAATATCA
2401 TTTATTTTTT ACATTATTAA GAAAAAGAT TTATTTATTT AAGACAGTCC
2451 CATCAAAACT CCGTCTTTGG AAATCCGACC ACTAATTGCC AAACACCGCT
2501 TCGTGTGGCT CCACCTGGAT GTTCTGTGCC TGTAAACATA GATTCGCTTT
2551 CCATGTTGTT GGCCGGATCA CCATCTGAAG AGCAGACGGA TGGAAAAAGG
2601 ACCTGATCAT TGGGGAAGCT GGCTTTCTGG CTGCTGGAGG CTGGGGAGAA
2651 GGTGTTCATT CACTTGCATT TCTTTGCCCT GGGGGCGTGA TATTAACAGA
2701 GGGAGGGTTC CCGTGGGGGG AAGTCCATGC CTCCCTGGCC TGAAGAAGAG
2751 ACTCTTTGCA TATGACTCAC ATGATGCATA CCTGGTGGGA GGAAAAGAGT
2801 TGGGAACTTC AGATGGACCT AGTACCCACT GAGATTTCCA CGCCGAAGGA
2851 CAGCGATGGG AAAAATGCCC TTAAATCATA GGAAAGTATT TTTTTAAGCT
2901 ACCAATTGTG CCGAGAAAAG CATTTTAGCA ATTTATACAA TATCATCCAG
2951 TACCTTAAAC CCTGATTGTG TATATTCATA TATTTTGGAT ACGCACCCCC
3001 CAACTCCCAA TACTGGCTCT GTCTGAGTAA GAAACAGAAT CCTCTGGAAC
3051 TTGAGGAAGT GAACATTTCG GTGACTTCCG ATCAGGAAGG CTAGAGTTAC
3101 CCAGAGCATC AGGCCGCCAC AAGTGCCTGC TTTTAGGAGA CCGAAGTCCG
3151 CAGAACCTAC CTGTGTCCCA GCTTGGAGGC CTGGTCCTGG AACTGAGCCG
3201 GGCCCTCACT GGCCTCCTCC AGGGATGATC AACAGGGTAG TGTGGTCTCC
3251 GAATGTCTGG AAGCTGATGG ATGGAGCTCA GAATTCCACT GTCAAGAAAG
3301 AGCAGTAGAG GGGTGTGGCT GGGCCTGTCA CCCTGGGGCC CTCCAGGTAG
3351 GCCCGTTTTC ACGTGGAGCA TAGGAGCCAC GACCCTTCTT AAGACATGTA

Fig. 7-3

```
3401 TCACTGTAGA GGGAAGGAAC AGAGGCCCTG GGCCTTCCTA TCAGAAGGAC
3451 ATGGTGAAGG CTGGGAACGT GAGGAGAGGC AATGGCCACG GCCCATTTTG
3501 GCTGTAGCAC ATGGCACGTT GGCTGTGTGG CCTTGGCCAC CTGTGAGTTT
3551 AAAGCAAGGC TTTAAATGAC TTTGGAGAGG GTCACAAATC CTAAAAGAAG
3601 CATTGAAGTG AGGTGTCATG GATTAATTGA CCCCTGTCTA TGGAATTACA
3651 TGTAAAACAT TATCTTGTCA CTGTAGTTTG GTTTTATTTG AAAACCTGAC
3701 AAAAAAAAAG TTCCAGGTGT GGAATATGGG GGTTATCTGT ACATCCTGGG
3751 GCATTAAAAA AAAATCAATG GTGGGGAACT ATAAAGAAGT AACAAAAGAA
3801 GTGACATCTT CAGCAAATAA ACTAGGAAAT TTTTTTTTCT TCCAGTTTAG
3851 AATCAGCCTT GAAACATTGA TGGAATAACT CTGTGGCATT ATTGCATTAT
3901 ATACCATTTA TCTGTATTAA CTTTGGAATG TACTCTGTTC AATGTTTAAT
3951 GCTGTGGTTG ATATTTCGAA AGCTGCTTTA AAAAAATACA TGCATCTCAG
4001 CGTTTTTTTG TTTTTAATTG TATTTAGTTA TGGCCTATAC ACTATTTGTG
4051 AGCAAAGGTG ATCGTTTTCT GTTTGAGATT TTTATCTCTT GATTCTTCAA
4101 AAGCATTCTG AGAAGGTGAG ATAAGCCCTG AGTCTCAGCT ACCTAAGAAA
4151 AACCTGGATG TCACTGGCCA CTGAGGAGCT TTGTTTCAAC CAAGTCATGT
4201 GCATTTCCAC GTCAACAGAA TTGTTTATTG TGACAGTTAT ATCTGTTGTC
4251 CCTTTGACCT TGTTTCTTGA AGGTTTCCTC GTCCCTGGGC AATTCCGCAT
4301 TTAATTCATG GTATTCAGGA TTACATGCAT GTTTGGTTAA ACCCATGAGA
4351 TTCATTCAGT TAAAAATCCA GATGGCGAAT GACCAGCAGA TTCAAATCTA
4401 TGGTGGTTTG ACCTTTAGAG AGTTGCTTTA CGTGGCCTGT TTCAACACAG
4451 ACCCACCCAG AGCCCTCCTG CCCTCCTTCC GCGGGGGCTT TCTCATGGCT
4501 GTCCTTCAGG GTCTTCCTGA AATGCAGTGG TCGTTACGCT CCACCAAGAA
4551 AGCAGGAAAC CTGTGGTATG AAGCCAGACC TCCCCGGCGG GCCTCAGGGA
4601 ACAGAATGAT CAGACCTTTG AATGATTCTA ATTTTAAGC AAAATATTAT
4651 TTATGAAAG GTTTACATTG TCAAAGTGAT GAATATGGAA TATCCAATCC
4701 TGTGCTGCTA TCCTGCCAAA ATCATTTTAA TGGAGTCAGT TTGCAGTATG
4751 CTCCACGTGG TAAGATCCTC CAAGCTGCTT TAGAAGTAAC AATGAAGAAC
4801 GTGGACGTTT TTAATATAAA GCCTGTTTTG TCTTTTGTTG TTGTTCAAAC
```

Fig. 7-4

```
4851 GGGATTCACA GAGTATTTGA AAAATGTATA TATATTAAGA GGTCACGGGG

4901 GCTAATTGCT AGCTGGCTGC CTTTTGCTGT GGGGTTTTGT TACCTGGTTT

4951 TAATAACAGT AAATGTGCCC AGCCTCTTGG CCCCAGAACT GTACAGTATT

5001 GTGGCTGCAC TTGCTCTAAG AGTAGTTGAT GTTGCATTTT CCTTATTGTT

5051 AAAAACATGT TAGAAGCAAT GAATGTATAT AAAAGC
```

Fig. 7-5

IDENTIFICATION AND CHARACTERIZATION OF A GENE WHICH PROTECTS CELLS FROM PROGRAMMED CELL DEATH AND USES THEREFOR

RELATED APPLICATION

This application is a divisional of U.S. Ser. No. 08/801,248 filed Feb. 19, 1997 (now abandoned); which is a file wrapper continuation of U.S. Ser. No. 08/288,295, filed Aug. 10, 1994 (now abandoned), which is a divisional of U.S. Ser. No. 07/927,681, filed Aug. 10, 1992 (now abandoned), which is a continuation-in-part of U.S. Ser. No. 07/898,933, filed Jun. 12, 1992 (now abandoned).

GOVERNMENT FUNDING

Work described herein was supported by grant number GM24663 from the U.S. Public Health Service. The United States government has certain rights in the invention.

BACKGROUND

Cell death is a fundamental aspect of animal development. A considerable proportion of the cells that are generated die during the normal development of both vertebrates (Glucksmann, *Biol. Rev. Cambridge Philos. Soc.* 26:59–86 (1951)) and invertebrates (Truman and Schwartz, *Ann. Rev. Neurosci.* 7:171–188 (1984)). Cell death plays a role in morphogenesis (e.g., of the eye, secondary palate, heart, nervous system and limbs in vertebrate embryos), metamorphosis (e.g., in moths and other insects), and tissue homeostasis (e.g., of epithelial linings and the thymus), as well as in neuron selection during the establishment of synaptic connections and in sexual dimorphism (reviewed by Ellis et al., *Ann. Rev. Cell Biol.* 7:663–698 (1991)). Cell death which occurs as a part of normal development will be referred to herein as physiological cell death.

Besides physiological cell death, cell death may occur as a pathological manifestation of disease, in which case it will be referred to herein as pathological cell death (see review by Trump and Mergner (1974), in: *The Inflammatory Process*, vol. 1, 2nd ed. (eds. Zweifach et al.), Academic Press, New York, pp. 115–257). Cell death can result from a variety of injuries to the cell, including toxins, ischemia (lack of blood supply), hypoxia (lack of oxygen) and infectious agents, as well as from genetic mutations. The major clinical aspects of most degenerative diseases are a consequence of cell death. For example, Huntingtons's disease, Parkinson's disease, Alzheimer's disease and amyotrophic lateral sclerosis are marked by degeneration of neurons, while Duchenne muscular dystrophy is characterized by muscle degeneration. In addition, some cancers are thought to be caused by a defect in cell death processes. Thus, understanding and preventing cell death can be viewed as one of the major goals of biomedical research.

The simple and invariant anatomy and development of the nematode *Caenorhabditis elegans* have made it an attractive system for the study of cell death. Because *C. elegans* is small, cellularly simple and transparent, Nomarski differential interference microscopy can be used to observe individual cells throughout development. As a result, the complete cell lineage of *C. elegans*, from zygote to adult, has been elucidated (Sulston and Horvitz, *Dev. Biol.* 82:110–156 (1977); Kimble and Hirsh, *Dev. Biol.* 70:396–417 (1979); Sulston et al., *Dev. Biol.* 100:64–119 (1983)).

Cell death is an important component of the development of *C. elegans*: during the development of the adult hermaphrodite, the generation of 816 nongonadal cells is accompanied by the generation and subsequent deaths of an additional 131 cells. Cell death appears to be an integral part of the differentiation of a variety of tissues. The pattern of cell deaths is essentially invariant among different animals, i.e, the same set of cells die at the same developmental time. In addition, a vast majority of cell deaths in *C. elegans* does not appear to be initiated by interaction with surrounding cells or diffusible factors.

Genetic analysis has identified many genes that affect programmed cell death in *C. elegans* (reviewed by Ellis et al. (1991) supra). The activities of two genes, ced-3 and ced-4, seem to be required for the onset of almost all *C. elegans* programmed cell deaths (Ellis and Horvitz, *Cell* 44:817–829 (1986)). Mutations in ced-3 and ced-4 block essentially all programmed cell deaths. In ced-3 and ced-4 mutants, cells that normally undergo programmed cell death instead survive, differentiate and even function (Ellis and Horvitz (1986) supra; Avery and Horvitz, *Cell* 51:1071–1078 (1987); White et al., *Phil. Trans. R. Soc. Lond. B.* 331:263–172 (1991)). Genetic analyses indicate that ced-3 and ced-4 genes most likely act within dying cells; this suggests that of these genes are expressed within dying cells and either encode cytotoxic molecules or control the activities of cytotoxic molecules (Yuan and Horvitz, *Dev. Biol.* 138:33–41 (1990)).

Relatively little is known about the mechanism of cell death. Initiation of cell death occurs in response to a variety of signals. External injuries and cytotoxic agents cause cells to die. Endocrine signals trigger cell death during insect metamorphosis, thymocyte death and regression of the prostate in the male rat after castration. Lack of neuronal growth factors is suspected to be the cause of certain neuronal cell deaths during vertebrate development and may also be the cause of cell deaths in certain neurodegenerative diseases. A specific protein, Mullerian inhibiting substance, is responsible for the regression of the Mullerian duct during the development of male mammals. In addition, genetically programmed cell deaths which occur apparently autonomously of cell—cell interaction or diffusible factors are observed in *C. elegans* and other invertebrates. (Truman and Schwartz, *Neuro. Comm.* 1:66–72 (1982); Cohen and Duke, *J. Immunol.* 132:38–42 (1984); Isaacs, *Prostate* 5:545–557 (1984); Martin et al., *J. Cell. Biol.* 106:829–844 (1988); Oppenheim and Prevette, *Neurosci. Abstr.* 14:368 (1988); Beal et al., *Nature* 321:168–171 (1986); Birkmayor and Hornykiewicz, *Advances in Parkinsonism, Fifth International Symposium on Parkinson's Disease, Vienna*, Roche, Basle, 1976; Lagsto et al., *Science* 219:979–980 (1983); Rossor, *Lancet* 2:1200–1204 (1982); Biel et al., *Science* 229:289–291 (1985); Cosi et al., in: *Advances in Experimental Medicine and Biology*, vol. 209, Plenum Press, New York, 1987; Bonilla et al., *Cell* 54:447–452 (1988); Picard and Josso, *Biomedicine* 25:147–150 (1976)).

Cell deaths also vary morphologically. Two major categories of cell deaths have been established based on morphological features (Kerr et al., *Br. J. Cancer* 26:239–257 (1972)). The first type of cell death, called necrosis, is characterized by cellular swelling, rupture of plasma and internal membranes, and eventual leakage of cellular contents into the extracellular space. The second, called apoptosis, involves progressive condensation of cytoplasm and nuclear chromatin and eventual fragmentation of cellular membranes into 'apoptotic bodies', which are usually digested by macrophages or adjacent epithelial cells. Necrosis is most often a manifestation of certain pathological conditions, e.g., injury by complement (Hawkins et al., Am. J. Pathol. 68:255–288 (1972)), hypoxia (Jennings et al., Am. J. Pathol. 81:179–198 (1975)), or exposure to a variety of toxins (McLean et al., Int. Rev. Exp. Pathol. 4:127–157 (1965)). In contrast, apoptosis is usually associated with physiological conditions, e.g., embryogenesis (Bellaris, J. Anat. 95:54–60 (1961); Saunders, Science 154:604–612 (1966)) and metamorphosis (Truman, Ann. Rev. Neurosci. 7:171–188 (1984). Interestingly, morphological features of physiological cell death in C. elegans resemble, in general, those of apoptosis in vertebrates (Ellis et al., Ann. Rev. Cell Biol. 7:663–698 (1991)). However, deviations from the standard descriptions of necrosis and apoptosis are often observed. It is uncertain whether this morphological classification reflects real differences in underlying mechanisms of cell death.

Although the initiation and morphology of cell death vary, there is evidence which suggests that most physiological and some pathological cell deaths may share a common feature involving the activation of cell death genes. The existence of a genetic cell death program in a variety of organisms is suggested by the observation that protein and RNA synthesis inhibitors can prevent or delay a variety of cell deaths (insect metamorphosis, prostate regression, vertebrate neuronal cell death and thymocyte cell death) (Lockshin, J. Insect Physiol. 15:1505–1516 (1969); Stanisic et al., Invest. Urol. 16:19–22 (1978); Martin et al. (1988) supra; Oppenheim and Prevette (1988) supra; Cohen and Duke (1984) supra), New RNA and protein species have been found after the initiation of cell death in the rat prostate after castration (Buttyan et al., Molecular Endocrinology 2:650–657 (1988); Lee et al., Prostate 7:171–185 (1985)). Thus, a better understanding of the mechanisms of cell death would have wide biological application and provide a basis for altering or controlling the process.

SUMMARY OF THE INVENTION

The present invention relates to genes, referred to herein as cell death-protective genes, which function to protect cells against programmed cell death by antagonizing the activity of genes which cause cell death. As described herein, Applicants have identified what appears to be a key or master regulatory gene whose activity determines whether a cell survives or undergoes cell death.

Specifically, a cell death-protective gene from the nematode Caenorhabditis elegans, called ced-9, has been identified, sequenced, and characterized. ced-9 is essential for C. elegans development and apparently functions by protecting cells which normally live during development from programmed cell death. As is also described herein, a mutation that constitutively activates ced-9 prevents cells which normally die during development from undergoing programmed cell death, and mutations that inactivate ced-9 result in the deaths of cells which normally survive during development and consequently, in embryo lethality. ced-9 has been shown to function by antagonizing the activities of the cell death genes ced-3 and ced-4. Thus, the C. elegans ced-9 gene appears to act as a binary switch to regulate programmed cell death. Results described herein indicate that many and possibly all cells that survive during C. elegans development do so because ced-9 activity prevents them from undergoing programmed cell death.

In addition, a human equivalent of the C. elegans ced-9 gene has been discovered. The deduced amino acid sequence of the ced-9 gene product was found to have about 23% identity and about 47% similarity to the product of the human oncogene bcl-2. This structural similarity, together with previous studies on bcl-2 activity in lymphocytes, strongly suggests that bcl-2 is a human equivalent of ced-9. Applicants further provide methods for identifying other cell death-protective genes from a variety of organisms, including vertebrates (e.g., mammals and particularly humans), invertebrates (e.g., insects), microbes (e.g., yeast), and possibly plants. Furthermore, comparison of ced-9, bcl-2, and other cell death-protective genes and their encoded products provides a way to define key functional features or regions of these genes and gene products. Those features or parts that are conserved between these genes or their gene products are most likely to be functionally important.

Applicants further provide methods and agents for altering the occurrence of cell death in a population of cells and hence, affecting the proliferative capacity and longevity of tissues or organisms. Methods and agents for both decreasing and increasing cell deaths are described. The agents may be all or portions of the cell death-protective genes and encoded products, or derivatives, mimetics, activators or inactivators, or agonists or antagonists of the activity of cell death-protecting genes.

As a result of this work, methods and agents for altering cell death are available for therapeutic or preventive treatment of diseases or conditions involving cell death. Methods and agents for reducing cell death are available and are potentially useful for treating disorders and conditions, including those associated with aging, stroke, traumatic brain injury, myocardial infarction, degenerative diseases (including Huntington's disease, amyotropic lateral sclerosis, Alzheimer's disease, Parkinson's disease, and Duchenne's muscular dystrophy), and viral and other types of infection (such as with the human immunodeficiency virus or HIV). Methods and agents for increasing cell deaths are also available which are potentially useful for decreasing the growth of or for killing specific cell populations, such as infected cells or autoreactive immune cells. These methods and agents may also be useful for treating diseases or conditions characterized by excessive cell growth or an abnormally low frequency of cell death (e.g., neoplasia and other cancerous growth). Methods and agents which increase cell death are also potentially useful for treating viral, parasitic, and other infections and to kill undesirable organisms, for example, in pest control or biological containment applications.

Accordingly, in one aspect, the invention features substantially pure nucleic acid which is a cell death-protective gene. Preferably, the cell death-protective gene is the C. elegans ced-9 gene. In a related aspect, the invention features substantially pure nucleic acid consisting essentially of all or a portion of the nucleotide sequence selected from the group consisting of: a) the nucleotide sequence shown in FIG. 2; b) the nucleotide sequence shown in FIG. 3; and c) substantially pure nucleic acid encoding the amino acid sequence shown in FIG. 4. In further related aspect, the invention includes isolated protein encoded by the C. elegans ced-9 gene, preferably consisting essentially of the amino acid sequence shown in FIG. 4; and an antibody specifically reactive with the protein encoded by the C. elegans ced-9 gene.

In another aspect, the invention features substantially pure nucleic acid which is a mutated cell death-protective gene, wherein the mutation constitutively activates the gene. In one embodiment, the mutated cell death-protective gene is C. elegans ced-9, more preferably, the mutation is n1950 and, most preferably, the mutation is associated with a glycine to glutamic acid change at codon 169. In another embodiment, the constituatively activating mutation in the cell death-protective gene is human bcl-2. Preferably, the mutation is associated with a glycine to glutamic acid change at codon 145.

In additional aspects, the invention features substantially pure nucleic acid which is a mutated cell death-protective gene, wherein the mutation inactivates the gene and isolated protein encoded by this nucleic acid. In one embodiment the cell death-protective gene is *C. elegans* ced-9, and, preferably, the mutation is selected from the group consisting of: a) n2077; b) n2161; and c) n1653ts; or, the mutation is associated with a change selected from the group consisting of: a) tyrosine to asparagine at codon 149; and b) glutamine to termination at codon 160. In another embodiment, the cell death-protective gene having a mutation which inactivates the gene is human bcl-2.

In another aspect, the invention features a method for identifying a novel cell death-protective gene by the steps of: a) obtaining a structurally similar gene by: 1) identifying a gene which is structurally similar to a cell death-protective gene; or 2) identifying a gene whose gene product is similar to the gene product of a cell death-protective gene; and b) determining that the structurally similar gene protects cells in which it functions from cell death. Identification of this similarity indicates a novel cell death-protective gene.

In one embodiment of this method for identifying genes, step a) includes the steps of: i) combining DNA with a nucleic acid probe comprising the cell death-protective gene, or a portion able to specifically hybridize to the cell death-protective gene, under conditions suitable for specific hybridization of the nucleic acid probe to complementary sequences; and ii) detecting specific hybridization of the nucleic acid probe to the DNA, wherein specific hybridization indicates that a structurally similar gene, or portion, is present in the DNA. Preferably, the DNA used in this embodiment is a gene library; or the nucleic acid probe further comprises degenerate oligonucleotides derived from the amino acid sequence of the product of the cell death-protective gene. In another embodiment, step a) includes the steps of: i) combining nucleic acid with primers comprising portions of the cell death-protective gene under conditions suitable for polymerase chain reaction; and ii) detecting specific DNA amplification, wherein specific DNA amplification produces a structurally similar gene, or portion. Preferably, the primers used in this embodiment further include degenerate oligonucleotides derived from the amino acid sequence of the product of the cell death-protective gene.

In another embodiment, step a) includes the steps of: i) combining an expression gene library with an antibody which binds specifically with the protein encoded by the cell death-protective gene under conditions suitable for specific antibody-antigen binding of the antibody to antigens expressed from the gene library; and ii) detecting specific antibody-antigen binding, wherein specific antibody-antigen binding indicates that a structurally similar gene is present in the expression gene library, thereby identifying a gene which is structurally similar to a cell death-protective gene.

In additional embodiments, step a) comprises searching a database of genes for a nucleotide sequence which is similar to the nucleotide sequence of the cell death-protective gene or searching a database of proteins for an amino acid sequence which is similar to the amino acid sequence of the protein encoded by the cell death-protective gene.

In yet another embodiment, step b) includes the steps of: i) using the structurally similar gene and a nematode which lacks the activity of the ced-9 gene to produce a transgenic nematode; and ii) determining a decrease in the cell deaths which occur during the development of the transgenic nematode relative to the nontransgenic nematode. A decrease in cell deaths indicates that the structurally similar gene protects cells in which it functions from cell death.

In another embodiment, step b) includes the steps of: i) introducing the structurally similar gene into cultured mammalian cells to produce transfected cells which express the gene; and ii) determining a decrease in cell deaths among the transfected cells under conditions which induce cell death, wherein a decrease in cell deaths indicates that the gene protects cells in which it functions from cell death.

In another aspect, the invention features a bioassay for identifying a gene which has cell death-protective activity. This bioassay includes the steps of: a) using DNA and a nematode which lacks the activity of the ced-9 gene to produce a transgenic nematode; and b) determining a decrease in the cell deaths which occur during the development of the transgenic nematode relative to the nontransgenic nematode. A decrease in cell deaths indicates the activity of a cell death-protective gene in the DNA, and thereby allows identification of a gene which has cell death-protective activity. Preferably, the nematode used in the bioassay underexpresses ced-9 or expresses inactivated Ced-9 protein; and/or the DNA is from an organism other than a nematode; and/or the DNA is an expression gene library. In a related aspect, the invention features substantially pure nucleic acid which is a cell death-protective gene identified by the foregoing bioassay and mutated derivatives thereof.

In another aspect, the invention features a bioassay to identify a mutation in a cell death-protective gene which alters the activity of the gene, comprising the steps of: a) using a cell death-protective gene having a mutation and a nematode which lacks ced-9 activity to produce a transgenic nematode; and b) comparing cell deaths which occur during the development of the transgenic nematode having the mutated gene with those which occur in a transgenic nematode having a non-mutated gene, wherein a difference in cell deaths indicates that the mutation alters the activity of the cell death-protective gene. This alteration in activity indicates a mutation in a cell death-protective gene which alters the activity of the gene. In a related aspect, the invention features substantially pure nucleic acid which is a cell death-protective gene having a mutation identified by this bioassay.

In yet another aspect, the invention features a bioassay for identifying an agent which mimics the activity of a cell death-protective gene, comprising the steps of: a) introducing an agent into a nematode which lacks the activity of ced-9; and b) detecting a decrease in cell deaths which occur in the nematode, wherein a decrease indicates that the agent mimics the activity of a cell death-protective gene. Preferably, the nematode used in the bioassay underexpresses ced-9 or expresses inactivated Ced-9 protein; and/or the agent is introduced into the nematode by a method selected from: microinjection, diffusion, or ingestion. In a related aspect, the invention features an agent identified by this bioassay.

In another aspect, the invention features a bioassay for identifying an agent which affects the activity of a cell death-protective gene, and includes the steps of: a) introducing an agent into a nematode which expresses a cell death-protective gene; and b) detecting a change in the pattern of cell deaths which occur in the development of the nematode, wherein a change indicates that the agent affects the activity of the cell death-protective gene. Preferably, the cell death-protective gene used in the assay is ced-9; or the nematode is a transgenic nematode produced from the integration of cell death-protective gene (e.g., bcl-2) into a nematode which lacks ced-9 activity. The nematode used in this may overexpresses or underexpresses the cell death-protective gene, or expresses an inactivated or constitutively activated form of the cell death-protective gene.

In a related aspect, the invention features an agent which affects the activity of a cell death gene identified by this bioassay. Preferably, the agent is selected from the group consisting of: a) single stranded nucleic acid comprising all or a portion of the antisense sequence of a cell death-protective gene which is complementary to the mRNA encoded by the gene; and b) DNA encoding a). The agent may also be a gene which is not a cell death-protective gene, or may be a mutated cell death-protective gene which does not protect cells from cell death and which antagonizes the activity of cell death-protective genes.

In another aspect, the invention features a bioassay for identifying a cell death-protective gene, which includes the steps of: a) introducing DNA into cultured mammalian cells to produce transfected cells which express gene(s) in the DNA; and b) detecting cell deaths among the transfected cells under conditions which induce cell death, wherein a decrease in cell deaths indicates the activity of a cell death-protective gene in the DNA. Preferably, the DNA used in the bioassay is an expression gene library. In a related aspect, the invention features substantially pure nucleic acid identified in the bioassay.

In another aspect, the invention features a bioassay for identifying a mutation in a cell death-protective gene which alters the activity of the gene and includes the steps of: a) introducing a cell death-protective gene having a mutation into cultured mammalian cells to produce transfected cells which express the mutated gene; and b) comparing cell deaths which occur among the transfected cells under conditions which induce cell death to cell deaths which occur among cells transfected with the non-mutated gene. A difference in cell deaths indicates that the mutation alters the activity of the gene. In a related aspect, the invention features substantially pure nucleic acid which is a cell death-protective gene having a mutation identified by the bioassay.

In a further aspect, the invention features a bioassay for identifying an agent which mimics the activity of a cell death-protective gene and includes the steps of: a) exposing cultured mammalian cells to an agent under conditions which induce cell death and which are appropriate for activity of the agent; and b) detecting cell deaths in said exposed cells, wherein a decrease in cell deaths indicates that the agent protects cells from cell death. In a related aspect, the invention features an agent identified by this bioassay.

In yet another aspect, the invention features a bioassay for identifying an agent which affects the activity of a cell death-protective gene and includes the steps of: a) exposing cultured mammalian cells which are protected from conditions which induce cell death by the activity of a cell death-protective gene to an agent under conditions which are appropriate for activity of the agent; and b) detecting cell deaths in the exposed cells. A change in cell deaths by this method indicates that the agent affects the activity of the gene. In a related aspect, an invention features an agent identified by this bioassay.

In another aspect, the invention features a method for altering cell death in a cell by altering in the cell the activity of a cell death-protective gene. Preferably, the cell death-protective gene is ced-9 or bcl-2 and/or the cell is a nematode cell or a human cell. In certain embodiments, the cell death is prevented by activation of the cell death-protective gene expression of the cell death-protective gene by virtue of a mutation which activates the protective gene product. The mutation may be the n1950 mutation in ced-9, or another mutation which is associated with a change from glycine to glutamic acid at codon 169, or the mutation may be a mutation in bcl-2, e.g., a change from glycine to glutamic acid at codon 145. In another embodiment, cell death is caused. This method involves inactivation of the cell death-protective gene so that it does not provide protection against programmed cell death. Preferably, cell death is caused by inactivating a cell death gene by mutation. For example, a mutation in ced-9 or bcl-2 may be employed. Where the cell death-protective gene is *C. elegans* ced-9, the mutation may be selected from the group consisting of: a) n2077; b) n2161; and c) n1653ts. The method of altering cell death may further include exposing the cell to an agent which alters the activity of a cell death-protective gene in the cell under conditions appropriate for activity of the agent.

Where the method of altering cell death involves increasing the activity of the cell death-protective gene, the method may include exposing the cell to an agent selected from the group consisting of: a) DNA which includes the cell death-protective gene; b) RNA encoded by the cell death-protective gene; c) protein encoded by the cell death-protective gene, or active portion thereof; d) an agent which mimics the activity of the cell death-protective gene; e) an activator of the cell death protective gene; and f) an agonist of the cell death-protective gene. Where the method involves decreasing the activity of the cell death-protective gene, the method may include exposing the cell to an agent selected from the group consisting of: a) single stranded nucleic acid which is complementary to the mRNA of the cell death-protective gene; b) DNA which directs the expression of a); c) a mutated cell death-protective gene which does not protect from cell death and which antagonizes the activity of the cell death-protective gene; d) an inactivator of the cell death-protective gene; and e) an antagonist of the cell death-protective gene.

In another aspect, the invention features a method for treating a condition characterized by increased cell deaths in a tissue. The method includes increasing activity of a cell death-protective gene which functions in the cells which are affected by the condition. Preferably, the affected tissue is exposed to an agent selected from the group consisting of: a) DNA comprising the cell death-protective gene; b) RNA encoded by the cell death-protective gene; c) protein encoded by the cell death-protective gene, or active portion thereof; d) an agent which mimics the activity of the cell death-protective gene; e) an activator of the cell death protective gene; and f) an agonist of the cell death-protective gene, under conditions appropriate for activity of the agent. The cell death-protective gene is selected from the group consisting of: a) bcl-2; b) a novel human cell death-protective gene which is structurally similar to bcl-2; and c) a novel human cell death-protective gene which is structurally similar to ced-9. The condition being treated is selected from the group consisting of: a) myocardial infarction; b) stroke; c) traumatic brain injury; d) neurodegenerative disease; e) muscular degenerative disease; f) aging; g) hypoxia; h) ischemia; i) toxemia; and j) infection; or the condition is a viral infection such as infection by the human immunodeficiency virus.

In another aspect, the invention provides a method for reducing a population of cells by decreasing the activity of a cell death-protective gene which functions in the cells. Preferably, the cells of the method are exposed to an agent selected from the group consisting of: a) single stranded nucleic acid which is complementary to the mRNA of the cell death-protective gene; b) DNA which directs the expression of a); c) a mutated cell death-protective gene which does not protect from cell death and which antagonizes the activity of the cell death-protective gene; d) an inactivator of the cell death-protective gene; and e) an antagonist of the cell death-protective gene, under conditions appropriate for the activity of the agent. Also preferably, the population of cells is selected from the group consisting of: a) neoplastic growth; b) cancerous tissue; c) infected cells; and d) autoreactive immune cells; and, preferably, the cell death-protective gene is selected from the group consisting of: a) bcl-2; b) a novel human cell death-protective gene which is structurally similar to bcl-2; and c) a novel human cell death-protective gene which is structurally similar to ced-9.

In another aspect, the invention features a method for treating a parasitic infection of a host animal, which includes the steps of administering an agent which decreases the activity of a cell death-protective gene which is specific to the parasite and does not harm the host animal. Preferably, the anti-parasitic agent is selected from: a) single stranded nucleic acid having all or a portion of the antisense sequence of the cell death-protective gene which is complementary to the mRNA of the gene; and b) DNA which encodes a); and, preferably, the parasite is a nematode.

In a further aspect, the invention provides a method of pest control, comprising decreasing the activity of a cell death-protective gene in the pest. Preferably, the method includes exposing the pest to an agent selected from the group consisting of: a) single stranded nucleic acid having all or a portion of the antisense sequence of the cell death-protective gene which is complementary to the mRNA of the gene; b) DNA which directs the expression of a); c) a mutated cell death-protective gene which does not protect from cell death and which antagonizes the activity of the cell death-protective gene; d) an inactivator of the cell death-protective gene; and e) an antagonist of the cell death-protective gene, under conditions appropriate for the activity of the agent.

In yet another aspect, the invention provides a method of biological containment of a recombinant organism by introducing nucleic acid into the organism which is able to direct the expression of an agent which inactivates a cell death-protective gene in the organism under predetermined conditions. Preferably, the agent used for containment is selected from the group consisting of: a) single stranded nucleic acid which has all or a portion of the antisense sequence of the cell death-protective gene which is complementary to the mRNA of the gene; b) DNA which directs the expression of a); c) a mutated cell death-protective gene which does not protect from cell death and which antagonizes the activity of the cell death-protective gene; and d) an inactivator of the cell death-protective gene; and more preferably, the agent kills the recombinant organism upon completion of a desired task by the organism.

BRIEF DESCRIPTION OF THE DRAWINGS

FIG. 2 shows the nucleotide sequence of the genomic region containing the C. elegans ced-9 gene, with selected restriction sites.

FIG. 3 shows the nucleotide sequence of a particular ced-9 cDNA, with selected restriction sites and the predicted translation product.

FIG. 4 shows the predicted amino acid sequence of the Ced-9 protein as deduced from the genomic and cDNA sequences.

FIG. 5 shows changes observed in several ced-9 mutants. Shown are changes in the DNA sequence and the resulting predicted change in the protein sequence associated with each mutation.

FIG. 6 shows the optimized alignment of the C. elegans Ced-9 and human Bcl-2 proteins. Identical residues are indicated by vertical bars between the sequences, and similar residues are indicated by one or two dots (. or :), for weak and strong similarity, respectively. A residue that is mutated in the gain-of-function allele n1950 is conserved and has been boxed. Residues mutated in the loss-of-function alleles, n1653ts and n2077, are also indicated by boxes.

FIG. 7 shows the cDNA sequence of bcl-2. The coding sequence is from nucleotides 1459 to 2178, inclusive.

DETAILED DESCRIPTION OF THE INVENTION

Figure 1:
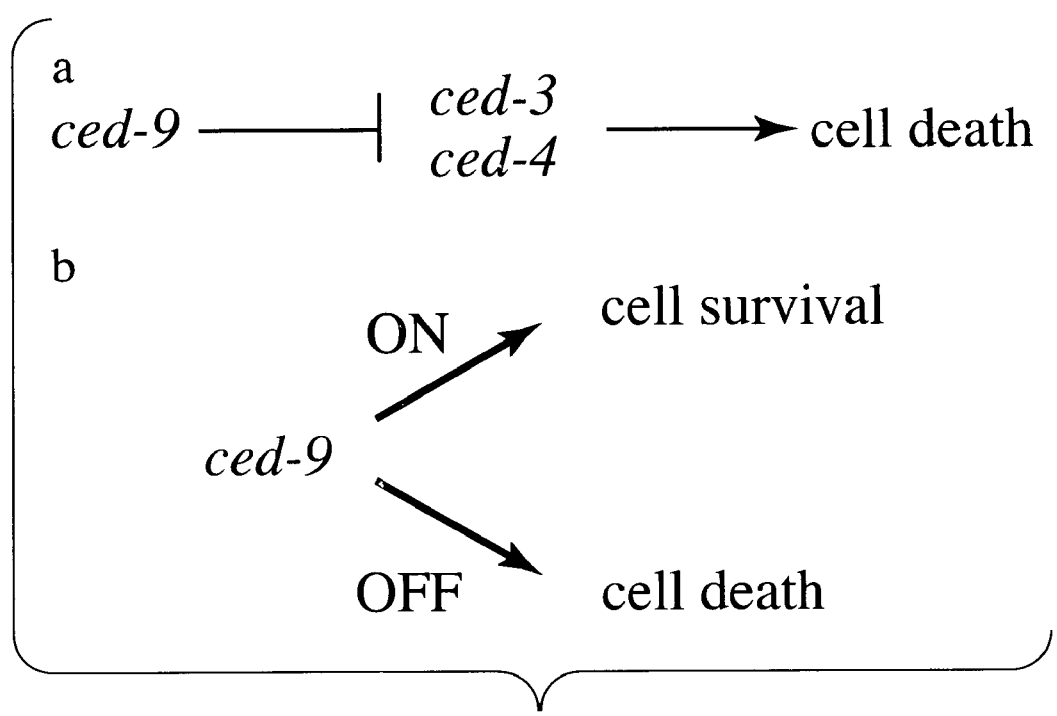
FIG. 1 is a diagrammatic representation of a model for ced-9 function. (a) ced-9 is a negative regulator of ced-3 and ced-4 activity. (b) ced-9 acts as a binary switch to regulate programmed cell death. When ced-9 is active, the activities of ced-3 and ced-4 are blocked, and the cell survives. When ced-9 is inactive, ced-3 and ced-4 are activated, leading to programmed cell death.

Programmed cell death is cell death which occurs during normal development and/or which involves the activities of cell death genes, some of which may be suicide genes. Programmed cell death is a fundamental aspect of normal development in invertebrates and vertebrates and of vertebrate tissue homeostasis, and may also be an underlying pathological mechanism in disorders which involve cell death, including degenerative diseases, stroke, traumatic brain injury, and myocardial infarction, conditions associated with aging, and viral and other types of infection. In addition, some cancers are believed to be caused in part by defects in cell death processes.

This invention relates to genes, referred to as cell death-protective genes, which protect cells against programmed cell death by antagonizing the activities of cell death genes (i.e., genes whose activity cause cell death). As described below, a cell death-protective gene from the nematode *Caenorhabditis elegans*, called ced-9, has been identified, sequenced, and characterized. Mutations which constitutively activate and inactivate ced-9 gene function have been identified and are also described below. As further described below, the deduced amino acid sequence of the ced-9 gene product was found to have about 23% identity and about 47% similarity to the product of the human oncogene bcl-2. The structural and functional similarity of bcl-2 to ced-9 strongly suggests that bcl-2 may be a human equivalent of ced-9 and thus, a cell death-protective gene. Using ced-9 and bcl-2, other cell death-protective genes from a variety of organisms can be obtained. In addition, comparison of equivalent genes and their encoded products, as well as mutational analysis, is expected to indicate key functional features or regions of the genes or gene products. The cell death-protective genes and their gene products are further useful for developing and identifying agents which affect the activity of cell death-protective genes. These agents may be useful for altering (increasing or decreasing) the occurrence of cell death in a cell population or organism, and thus, altering the longevity of the cell population or organism. Further described below are bioassays which are useful for testing and screening for novel cell death-protective genes, mutations in these genes and agents which affect the activity of the genes. Other uses of the invention are also described.

The activity of a cell death-protective gene refers herein to the activity of the encoded product(s) of the gene as well as to the gene per se. Thus, agents and mutations which affect the activity of a cell death-protective gene include those which affect the activity of the gene or a product of the gene. The agents may interact with the gene or RNA or protein encoded by the gene, or may exert its effect more indirectly. The agents may affect the level of expression as well as the function of the gene or gene product.

Genetic Analyses of the ced-9 Gene

A cell-death protective gene, called ced-9, has been identified in the nematode *C. elegans* that functions to prevent cells which normally live during development from undergoing programmed cell death. The ced-9 gene was defined by a dominant gain-of-function (gf) mutation, called n1950, which was mapped to chromosome III. The n1950 mutation constitutively activates the ced-9 gene and causes cells which normally die during development to live. Activated ced-9 prevents programmed cell deaths throughout the animal, and, as shown for certain nerve cells, not only prevents cells from dying, but also generates surviving cells that are sufficiently healthy to function. ced-9(n1950) also shows a maternal effect, suggesting that the maternal ced-9 gene product is contributed to the developing oocyte. Genetic analysis of ced-9(n1950) is further described in Example 1 and Table 1 (tables are at the end of the Detailed Description).

Loss-of-function (lf) mutations which inactivate the protective function of ced-9 and cause cells which normally live during *C. elegans* development to die were also identified. These mutations result in embryonic lethality in the progeny of homozygous animals, indicating that ced-9 function is essential for development. Four ced-9(lf) mutations were isolated, nDf40, n2077, n2161, and n1653ts. The lf mutations also show maternal effects. The amount of wild-type ced-9 product contributed by heterozygous mothers to homozygous ced-9(lf) embryos seems to be sufficient to allow these embryos to survive and develop almost normally. As a consequence of this maternal rescue, the lethality that results from an absence of ced-9 function during early development is apparent only in the second generation. Most of the ectopic cell deaths observed in the first generation of homozygous ced-9(lf) animals occur late, during post-embryonic development. It is possible that these late lineages are more seriously affected because dilution or degradation has reduced the amount of maternal ced-9 product to a level at which it cannot effectively protect against cell death. The isolation and genetic analysis of these loss-of-function mutations are further described in Examples 2 and 3 and Table 2.

As described in Example 4, the ced-9 gene appears to prevent cell death by antagonizing the activities of the cell death genes, ced-3 and ced-4, which have been shown to be required for almost all programmed cell deaths which occur in the development of *C. elegans* (Ellis and Horvitz, *Cell* 44:817–829 (1986)).

These results indicate that ced-9 acts as a binary switch to regulate programmed cell death (FIG. 1). Remarkably, it seems that many and possibly all cells that survive during *C. elegans* development do so because ced-9 gene activity prevents them from undergoing programmed cell death. Furthermore, cells protected by a constitutively activated ced-9 gene appear to be healthy and to function normally. Thus, ced-9 seems to be a key or master regulatory gene of cell death processes.

Sequence Analysis of the ced-9 Gene and Product

The genomic region containing the ced-9 gene was cloned and sequenced, as described in Example 5. FIG. 2 shows the nucleotide sequence of this region, including the location of selected restriction sites.

Several ced-9 cDNAs representing the same or different transcripts were obtained and sequenced, as described in Example 5. The nucleotide sequence of one of these cDNAs is shown in FIG. 3 with restriction sites and the amino acid sequence of the predicted translation product. As shown in FIG. 4, ced-9 encodes a 280 amino acid (aa) polypeptide.

The gain-of-function mutation, n1950, was also sequenced. As shown in FIG. 5, the n1950 mutation, which is responsible for the gain-of-function change in ced-9 activity, is associated with a glycine to glutamic acid change at codon 169. It is likely that this amino acid alteration is the consequence of the n1950 mutation and thus is functionally responsible for the increased activity of ced-9. However, although no other alterations in ced-9 are known to be present in n1950 mutant strains, it remains possible that another alteration exists and that it is this other alteration that is responsible for the gain-of-function change in ced-9 activity. If so, this other amino acid alteration is nonetheless defined by the n1950 mutation and its molecular identity can be determined by DNA sequencing, using established methods. The functional importance of DNA sequence alterations associated with ced-9 mutations can be verified in transgenic *C. elegans* animals which carry the sequence alteration alone. DNA containing alterations in the wild-type gene can be made by standard methods of in vitro mutagenesis and used to construct the transgenic animals.

The loss-of-function mutations, n1653ts and n2077, were also sequenced and found to be associated with a tyrosine to asparagine change at codon 149 and a glutamine to premature termination at codon 160, respectively.

Similarity Between ced-9 and a Human Oncogene

Sequence similarity to the ced-9 gene product was discovered in the product of the human oncogene bcl-2 (Tsujimoto et al., *Proc. Natl. Acad. Sci. USA* 83:5214–5218 (1986)). Alignment of the two sequences shows 23% identity and 47% similarity between the two proteins (FIG. 6).

Alignment of the two sequences was generated with the Gap program in the Sequence Analysis Software Package (Genetics Computer Group, Wisconsin), which uses the algorithm of Needleman and Wunsch (*J. Mol. Biol.* 48:443–453 (1970)) to find the alignment of two complete sequences that maximize the number of matches and minimizes the number of gaps.

bcl-2 is one of a number of genes, of both viral and cellular origin, which are thought to be inhibitors of cell death processes (Vaux et al., *Nature* 335:440–442 (1988); Henderson et al., *Cell* 65:1107–1115 (1991); Ciem et al., *Science* 254:1388–1390 (1991)). Overexpression of bcl-2 prevents or delays the onset of apoptic cell death in both B cells and T cells (Vaux et al. (1988) supra; Nunez et al., *J. Immun.* 144:3602–3610 (1990); Sentman et al., *Cell* 67:879–888 (1991); Strasser et al., *Cell* 67:889–899 (1991)). These cell deaths seem to involve the activities of cell death genes, as gene expression is required for the process (Duke and Cohen, *Lymphokine Res.* 5:289–299 (1986)). In many tissues in which homeostasis is regulated by cell death, bcl-2 expression occurs in progenitor and long-lived cells (Hockenbery et al., *Proc. Natl. Acad. Sci. USA* 88:6961–6965 (1991)). The structural similarity of the Bcl-2 protein to Ced-9, together with these previous findings on bcl-2 activity in lymphocytes, suggest that, like ced-9, the bcl-2 gene antagonizes the activities of cell death genes and is required in cells that survive to protect them from programmed cell death.

Cell Death-Protective Genes in Other Organisms

As a result of the work described herein, a gene which plays a key role in determining cell death has been identified, sequenced and characterized. This invention makes it possible to identify and isolate equivalent genes in other organisms, including vertebrates (e.g., mammals and particularly humans), invertebrates (e.g., insects), microbes (e.g., yeast), and possibly plants. The reasonableness of this approach has been demonstrated by the structural and functional similarity of the human gene bcl-2 to ced-9. As discussed below, there is evidence to suggest that programmed cell death is important in the development of a variety of organisms and tissues, and that different types of cell deaths, whether physiological or pathological, may share a common mechanism.

Evidence suggests that cell deaths that are mechanistically similar to the programmed cell deaths which occur in the development of *C. elegans* and other invertebrates may be very common in vertebrate development, as well. First, cell deaths that are similar to the programmed cell death seen in invertebrates were also observed in vertebrates (Glucksman (1951) supra; Saunders and Fallon, in: *Major Problems in Developmental Biology* (*25th Symposium of the Society for Developmental Biology*), Lockes (ed.) Academic Press, New York, 1966, pp. 289–314; Carr and Simpson, *Dev. Brain Res.* 2:57–162 (1982)). Some of these cells die shortly after they are born without obvious differentiation and others have been shown to be determined to die days before death occurs.

Second, some vertebrate neuronal cell deaths involve cell interactions and have been thought by some to be different from the apparently cell autonomous programmed cell deaths observed in invertebrates. However, even among the cell dependent deaths of these vertebrate neurons, the expression of new genetic information was found to be necessary for cell death, suggesting that a cell death program must be activated. Thus, it is possible that genes similar to those responsible for programmed cell death in *C. elegans* (ced-3 and ced-4) act in these vertebrate cell deaths as well.

Third, although many cell deaths in invertebrates are invariant and many in vertebrates are variable, the same mechanisms may nonetheless be responsible. Specifically, invariability does not reveal the mechanism of cell death. For example, invariability could be the result of an invariant cell—cell interaction. Thus, the linker cell in *C. elegans* males always dies at a certain specific time, but its death requires cell—cell interaction. The invariable programmed cell deaths in moths can, in fact, be prevented by manipulating their hormonal environment or changing cell—cell interactions. These observations argue that the distinction between programmed cell death during invertebrate development and cell death during vertebrate development may be more superficial than real. All of these cell deaths are influenced by genetic factors. Such argument leads to the notion that many and possibly all naturally occurring cell death during development may involve similar mechanisms.

The induction of specific genes has been found during the cell death processes in vertebrates. The induction of TRPM-2 was observed during a variety of cell death processes in rodents (Buttyan et al., *Mol. Cell. Biol.* 9:3473–3481 (1989)). TRPM-2 RNA is at high levels in cells that die during prostate regression in the adult male rat after castration, during renal atrophy following ureteral obstruction in rat, during necrosis of interdigital tissues of the mouse limb bud, and during the chemotherapeutic regression of tumors in rat. Thymocyte cell deaths induced in response to a variety of stimuli can have very similar morphological and biochemical properties, implying the involvement of a single mechanism of cell death. These observations suggest strongly that many types of cell deaths may share a similar mechanism.

In addition, it is possible that of the many human disorders characterized by extensive cell deaths, such as degenerative diseases, stroke, myocardial infarction and traumatic brain injury (for example, see Choi, *Neuron* 1:623–634 (1988)), some are caused by processes that inactivate or bypass the functions of genes like bcl-2 and ced-9. Furthermore, intracellular calcium has been implicated as a common mediator in a variety of pathological cell deaths, including deaths caused by external injury, toxins, degenerative diseases, ischemia, and hypoxia (Schanne et al., *Science* 206:700–702 (1979); Farber, *Life Science* 29:1289–1295 (1981)). Interestingly, amino acid sequence analysis of the *C. elegans* ced-4 gene product indicates that the Ced-4 protein may contain calcium-binding domains (Yuan, Ph.D. thesis, Harvard University, 1989, p. 139).

Uses of the Invention

This invention provides agents and methods based on ced-9, bcl-2, and other cell death-protective genes that are useful for diagnosis and treatment (both therapeutic and preventive) of a variety of disorders and conditions involving cell death. The invention is applicable to a variety of organisms, including humans. The genes and their encoded products can be used directly in therapeutics or provide a basis for designing and identifying agents which affect the occurrence of cell death. In addition, mutant forms of these regulatory genes, their encoded products and derivatives of the encoded proteins are available that are potentially useful for treatment.

Other cell death-protective genes can be obtained using the methods provided by this invention. As discussed above, it is likely that genes that are structurally and functionally similar to the *C. elegans* ced-9 gene function in a variety of organisms, including vertebrates (e.g., mammals and particularly humans), invertebrates (e.g., insects), microbes (e.g., yeast), and possibly plants. These equivalent genes have nucleotide sequences similar to portions of the ced-9 gene, or their encoded products have amino acid sequences similar to portions of the ced-9 protein. Equivalent genes also have similar activity to ced-9, in that they protect the cells in which they function from cell death. For example, the human gene bcl-2 was found to be equivalent to ced-9, as described herein.

Novel cell death-protective genes can be identified by any number of detection methods which utilize a defined nucleotide or amino acid sequence or antibodies as a probe. The genomic and cDNA nucleotide sequences of ced-9 and the deduced amino acid sequence of the Ced-9 protein are shown in FIGS. 2, 3, and 4, respectively. The bcl-2 gene and gene products can also be used as probes for cell death-protective genes. The cDNA nucleotide sequence of bcl-2 and the deduced amino acid sequence of the Bcl-2 protein are shown in FIGS. 6 and 7. For example, nucleic acid (DNA or RNA) containing all or part of the ced-9 or bcl-2 genes can be used as hybridization probes or as polymerase chain reaction (PCR) primers. Degenerate oligonucleotides derived from the amino acid sequences of the ced-9 or bcl-2 gene products can be used in these methods. In addition, antibodies, both polyclonal and monoclonal, which bind specifically to the Ced-9 and/or Bcl-2 protein can be produced and used as immunoprobes to screen expression libraries of genes. Databases containing known molecular (nucleotide or amino acid) sequences can also be searched for molecules which are structurally similar to ced-9, bcl-2, or their encoded products.

One strategy for detecting novel cell death-protective genes in various organisms is to initially probe animals which are taxonomically closely related to the source of the probes, for example, probing other worms with a probe derived from ced-9 or probing other mammals with a probe derived from bcl-2. Closely related species are more likely to possess cell death-protective genes or products which are detected with the probe than are more distantly related organisms. These new genes then provide additional sequences with which to probe the molecules of other animals, some of which may share conserved regions with the new genes or gene products but not with ced-9 or bcl-2. This strategy of using related genes in taxonomically closer organisms as stepping stones to genes in more distantly related organisms can be referred to as walking along the taxonomic ladder. However, cell death-protective genes or gene products from a variety of organisms may possess considerable sequence similarity and hence, be identifiable by more direct approaches.

The ced-9 and bcl-2 gene products were found to have 23% identity and 47% similarity. The molecular similarity between the ced-9 and bcl-2 gene products is useful, because the similarities between the two proteins reveal which parts or features of these molecules are important for function. For example, an activated bcl-2 may be produced by mutation of the codon which is equivalent to the site of the n1950 mutation in ced-9. More insights on the structure-function relationship of cell death-protective genes are expected to be obtained as more genes equivalent to ced-9 and/or bcl-2 are compared. This knowledge can be used to develop novel molecules which mimic or alter the activity of ced-9, bcl-2 or other cell death-protective genes.

Cell death-protective genes identified as described above can be sequenced by standard methods. Mutated forms of the genes may be identified by such methods, and some of these mutations are expected to constitutively activate and some to inactivate the genes like the n1950 gain-of-function and the loss-of-function mutations in ced-9. Mutationally activated and inactivated forms of cell death-protective genes may be useful for treatment of various disorders, as described further below. In addition, mutagenesis and other sorts of alterations can be performed on the genes and their encoded products to obtain other activated or inactivated proteins.

Mutations may also produce cell death-protective proteins with novel properties. For example, it is conceivable that a cell death-protective gene could be altered such that the gene product actively kills cells, rather than protecting them from cell death, perhaps by activating cell death genes or interfering with the function of wild-type cell death-protective gene products. Mutations and other alterations can be accomplished using known methods, such as in vivo and in vitro mutagenesis.

Furthermore, ced-9, bcl-2, or other cell death-protective genes, the corresponding mutant genes, and encoded products can be used to develop agents that activate or inactivate or modulate the activity of the cell death-protective genes. The source of the agents can be such traditional sources as extracts (e.g., bacterial, fungal or plant) and compound libraries, or can be provided by newer methods of rationale drug design. Information on functionally important regions of the genes or gene products, gained by sequence and/or mutational analysis, as described above, would be useful in drug design. The activity of the agents can be verified both by in vivo tests on wild-type, mutant, or transgenic animals containing various forms of ced-9, bcl-2, or other cell death-protective genes, as described below, and by in vitro tests using either cells expressing such genes or the products of these genes directly in biochemical experiments. Potential agents may include all or portions of the ced-9 or bcl-2 genes or gene products (RNA, protein), all or portions of other cell death-protective genes and their encoded products, nucleic acid or peptide derivatives of cell death-protective genes and gene products (e.g., smaller polypeptides and peptides), as well as peptidomimetics, and other molecules which mimic or affect the activity of cell death-protective genes. The agents can also be portions or derivatives of genes which do not by themselves protect cells from programmed cell death but which interact with cell death-protective genes.

This invention further provides bioassays which measure the activity of cell death-protective genes, and hence, are useful for identifying cell death-protective genes, for testing mutations in these genes, and for developing agents which mimic or alter cell death-protective activity. The bioassays can be further used to screen expression gene libraries for novel cell death-protective genes from nematodes and other organisms.

In one bioassay, genes or agents are introduced into nematodes to test their effect on cell deaths in vivo. Wild-type, mutant, or transgenic nematodes can be used as appropriate for the expected effect being tested. In one embodiment of the bioassay, transgenic nematodes are produced using sample DNA containing a candidate cell death-protective gene, a mutant cell death-protective gene or a gene library, to observe the effect of the sample DNA on the pattern of cell deaths during development of the nematode, using the methods of genetic analysis described for the ced-9 mutations. For example, a candidate gene can be introduced into a nematode which has a loss-of-function mutation in ced-9 to produce a transgenic nematode. A decrease in cell deaths compared to nontransgenic nematodes would indicate that the sample gene has cell death-protective activity. Similarly, a mutant cell death-protective gene which is inactivated would fail to complement the ced-9 loss-of-function mutation in the transgenic nematode, whereas a constitutively activated gene would decrease the number of cell deaths resulting from the mutation.

In another embodiment of the nematode bioassay, wild-type, mutant, and transgenic nematodes are used to test the effects of specific peptides and other small molecules in order to identify drugs that mimic, increase or decrease cell deaths. For example, wild-type animals can be used to test agents that inactivate or decrease the activity of ced-9 and cause increased cell deaths, or that activate or increase the activity of ced-9 and decrease or prevent cell deaths. Mutant or transgenic animals in which ced-9 is underexpressed or inactivated could be used to identify agents that mimic ced-9 in preventing cell death or which act as agonists of cell death-protective activity. Likewise, mutant or transgenic animals in which ced-9 is overexpressed or constitutively activated can be used to identify agents which act as antagonists of cell death-protective activity. Nematodes expressing wild-type ced-9 could be used to identify agents which activate or inactivate the ced-9 gene. The agents may include genes which are not cell death-protective genes but which interact with, regulate, or otherwise affect the activity of ced-9. The agents can be introduced into nematodes by microinjection, diffusion, or ingestion., Furthermore, agents which affect the activity of other cell death-protective genes, such as bcl-2, can be tested by transgenic animals with a loss-of-function mutation in ced-9. Agents which are non-cell death-protective genes can be tested on cell death-protective genes other than ced-9 by constructing doubly transgenic animals. These animals can be made by crossing a transgenic line which expresses a cell death-protective gene and an inactivated ced-9 gene with a transgenic line which expresses the agent gene.

An in vitro bioassay is also provided. In this bioassay, cultured mammalian cells are used to test genes and agents. Expression gene libraries can also be screened by this method. For example, genes, including genes which are structurally similar to ced-9 or bcl-2, can be introduced into mammalian cells by standard transfection methods to see if they protect from cell death under conditions which induce cell death, such as exposure to toxins or infection by yeast or bacteria. Mutations which activate or inactivate or otherwise affect cell death-protective activity can be tested. Furthermore, transfected mammalian cells which express a wild-type or mutant cell death-protective gene can be used to test agents which increase or decrease the activity of cell death-protective genes.

Using the above-described nucleic acid and antibody probes and bioassays, the identification and expression of ced-9, bcl-2 or other cell death-protective genes in cultured cells, tissues, and whole organisms can be studied to gain insights into their role in development and pathology. For example, these methods of detection and bioassay can be used to determine if certain mutations in cell death-protective genes, such as bcl-2, are associated with a pathological condition, such as a degenerative disorder.

This invention further provides means of altering or controlling the activity of a cell death-protective gene in a cell or organism, and, thus, to affect the occurrence of cell death. Activity of the regulatory gene can be altered to either increase or decrease cells deaths in a population of cells and, thus, affect the proliferative capacity and/or longevity of a cell population, organ, or entire organism.

ced-9, bcl-2, or other cell death-protective genes, and related and derivative products can be used to protect against cell death of any sort, including degenerative disease, stroke, traumatic brain injury, myocardial infarction, and viral and other types of infection, as well as cell death associated with normal aging. The gene, its encoded RNA, the protein encoded by the gene, or a peptide derived from or related to the gene can be delivered to the affected cells by various methods appropriate for the cells or organs being treated, including gene therapy. A non-peptide molecule which mimics, activates, or enhances the activity of a protein encoded by ced-9 or other cell death-protective gene, or polypeptide or peptide derivative, and which is designed on the basis of knowledge of the encoded protein, can also be used. That is, the gene or its product may be used either directly to protect against cell death or as the basis for developing another agent that can function like or increase the activity of the gene or its encoded product.

Mutationally activated forms of the genes can also be used to protect against cell death. Again, the mutated gene, its encoded RNA, the mutant protein encoded by the gene, a peptide derived from or related to the mutant protein, or a non-peptide mimetic, activator or agonist can be used. The n1950 mutation in ced-9 defines one way to make such a gene activated. A mutation equivalent to n1950 can be placed in a cell death-protective gene similar to ced-9 to activate it. For example, a constitutively activated bcl-2 protein might be produced by making a glycine to glutamic acid change at codon 145, as shown in FIG. 6, or other sequence alteration equivalent to the one which is responsible for the phenotype of the n1950 mutation in ced-9. (It has not yet been definitively shown that the glycine to glutamic acid alteration of codon 169 of ced-9 is responsible for the activated phenotype of the n1950 mutation. If it is not, the other mutational change(s) in ced-9 responsible for the activation of this gene can be identified as described above and produced in bcl-2 by in vitro mutagenesis to activate bcl-2). The mutant Bcl-2 protein may then be used as a clinically useful molecule or as a basis for developing or identifying a clinically useful molecule which protects from cell death.

Alternatively, ced-9, bcl-2, or other cell death-protective genes and their encoded products can be inactivated, or their activity reduced, in order to increase the frequency of cell death. This would be useful, for treating diseases and conditions characterized by an abnormally low frequency of cell death or excessive cell growth, such as neoplastic growth and other cancers. Interestingly, the human cell death-protective gene bcl-2 is also an oncogene, suggesting that cell death processes can be affected in neoplasia. Methods and agents which increase cell death would also be useful for decreasing the growth of or eliminating specific cell populations. For example, populations of autoreactive immune cells may be eliminated or reduced for treating autoimmune disorders. The activity of bcl-2 or other equivalent cell death-protective gene may be inactivated by using single stranded nucleic acid having an antisense sequence which is complementary to the normal transcript of the cell death-protective gene, such as antisense RNA, or DNAs which encode the antisense nucleic acid, or inactivators or antagonists of cell death-protective activity. These agents can be delivered by a variety of methods, including gene therapy. Inactivation of cell death-protective genes may also be useful in treating viral, parasitic and other types of infection, such as human immuno-deficiency virus (HIV) infection. A recombinant gene encoding an inactivator or antagonist of cell death-protective activity, such as antisense RNA which is complementary to the transcript of a cell death-protective gene, may be linked to a viral promoter which is specifically activated by a viral protein. The recombinant gene is introduced into infected cells. Infected cells containing the viral protein would then be killed and uninfected cells would be unaffected.

Inactivation of cell death-protective genes may also be used to kill organisms for the purpose of biological containment, pest control, or other applications in which populations of undesirable organisms are to be reduced. For example, suicide genes used for biological containment of recombinant bacteria have been reported (*Genetic Engineering News*, November 1991, p. 13). The suicide genes were engineered to be expressed simultaneously with the desired recombinant gene product so that the recombinant bacteria die upon completion of their task. The present invention provides for construction of recombinant suicide genes encoding antisense RNAs or other inactivators or antagonists of ced-9 or other cell death-protective genes which are useful in organisms in addition to bacteria, for example, in insects, fungi, and transgenic rodents.

Agents which inactivate or inhibit cell death-protective genes can further be used for pest control. For example, many nematodes are human, animal, or plant parasites. Populations of such parasites could be reduced or eliminated by causing their cells to undergo-programmed cell death. Parasites present in host animals, including humans, may also be reduced by treatment with agents, such as antisense RNAs, which decrease the activity of a cell death-protective gene specific to the parasite and which leave the host animal unharmed.

The following examples illustrate the invention and are not intended to be limiting in any way.

EXAMPLE 1

Gain-of-Function Mutation in ced-9

While screening for new *C. elegans* mutations that affect programmed cell death (Ellis and Horvitz, *Development* 112:591–603 (1991)), a dominant mutation, n1950, was isolated and genetically characterized, that prevents programmed cell deaths. n1950 was mapped to the right arm of the third chromosome, close to and about 0.05 map units to the right of the mutation unc-69(e587). The n1950 mutation defines a new gene, ced-9 III.

To quantify the effects of the ced-9(n1950) mutation on programmed cell deaths, cells in the anterior half of the pharynx of ced-9(n1950) animals were counted. In wild-type animals there are 49 cell nuclei in this region (Sulston et al., *Devl. Biol.* 100:64–119 (1983); Albertson and Thomson, *Phil. Trans. R. Soc.* B275:299–325 (1976)), and in ced-3 and ced-4 animals there are 12–14 additional nuclei (Table 1a). Similarly, in ced-9(n1950) animals there are about 13 extra nuclei in the anterior pharynx. These extra nuclei correspond exactly in position as well as in number to those that fail to die in ced-3 and ced-4 mutants.

Many extra cells survive not only in ced-9(n1950) homozygotes but also in ced-9(n1950)/+heterozygotes, indicating that the n1950 phenotype is dominant (Table 1b). In addition, the ced-9(n1950) mutation has a maternal effect: about twice as many cells fail to die in heterozygotes generated by mothers carrying at least one copy of the ced-9(n1950) mutation than in heterozygotes generated by homozygous wild-type mothers (Table 1b), suggesting that maternal ced-9 gene product is contributed to the developing oocyte.

Two observations indicate that ced-9(n1950) is a gain-of-function (gf) mutation. First, n1950 is a rare mutation with dominant effects (only one allele was recovered in a screen of over 24,000 haploid genomes (Ellis and Horvitz (1991) supra), which is a frequency about 10-fold lower than that at which typical loss-of-function mutations are recovered (Brenner, *Genetics* 77:71–94 (1974); Meneely and Herman, *Genetics* 92:99–115 (1979); Greenwald and Horvitz, *Genetics* 96:147–164 (1980)). Second, a deletion (nDf40) that removes the ced-9 gene does not have a dominant effect on cell death (Table 1b).

To study the effects of ced-9(n1950) on programmed cell deaths in regions other than the anterior pharynx, it was determined whether n1950 could prevent the accumulation of cell corpses in ced-1 and ced-5 mutants. In wild-type animals, dying cells are rapidly engulfed and degraded by a neighboring cell. In ced-1 and ced-5 mutants, this engulfment process is blocked, leading to an accumulation of undegraded cell corpses that can easily be seen in young larvae (Hedgecock et al., *Science* 220:1277–1279 (1983); Ellis et al. *Genetics* 129:79–94 (1991)). Mutations that inactivate ced-3 or ced-4 block programmed cell death and therefore prevent the accumulation of dead cells in ced-1 or ced-5 animals (Ellis and Horvitz, *Cell* 44:817–829 (1986)). Similarly, very few corpses appear anywhere in ced-l; ced-9(n1950) or ced-9(n1950); ced-5 double mutants (Table 1c). Thus, the ced-9(n1950) mutation, like mutations in ced-3 and ced-4, prevents programmed cell deaths throughout the animal.

The effects of ced-9(n1950) on the survival and function of a specific pair of nerve cells, the HSNs (hermaphrodite-specific neurons) were also studied (Trent et al., *Genetics* 104:619–647 (1983); White et al., *Phil. Trans. R. Soc.* B311:1–340 (1986); Desai et al., *Nature* 336:638–646 (1988); Desai and Horvitz, *Genetics* 121:703–721 (1989)). The two HSN neurons innervate the vulval muscles and control egg-laying by hermaphrodites. Mutations in the gene egl-1 cause these cells to undergo programmed cell death, resulting in egg-laying defective animals (Ellis and Horvitz, *Cell* 44:817–829 (1986); Trent et al., (1983) supra; Desai and Horvitz (1989) supra). Mutations in ced-3 and ced-4, which block programmed cell death, prevent the HSNs from dying in egl-1 mutants and suppress the egg-laying defect (Ellis and Horvitz (1986) supra). Similarly, the HSNs are present in ced-9(n1950); egl-1 double mutants, and egg-laying by these animals is normal (Table 1d). Thus, ced-9 (n1950), like the ced-3 and ced-4 mutations, not only prevents cells from dying but, at least in this case, also generates surviving cells that are sufficiently healthy to function.

Methods

The data presented in Table 1 were obtained as follows. Cell survival was quantified by counting the cells in the procorpus and metacorpus, which together constitute the anterior half of the pharynx (Albertson and Thomson, *Phil. Trans. R. Soc.* B275:299–325 (1976)). In wild-type animals there are 49 cell nuclei in this region. Cells that die are generated in characteristic positions (Sulston et al., *Devl. Biol.* 100:64–119 (1983)), making it easy to identify and count cells that have failed to die. The genotypes of animals studied for Table la were as shown.

The complete genotypes of the animals studied for Table 1b were, from top to bottom: wild-type (N2), non-Unc progeny of eT1 unc-36/nDf40 dpy-18 males crossed with unc-36 hermaphrodites, non-Unc progeny of n1950 males crossed with unc-69 hermaphrodites, Unc Dpy progeny from n1950/unc-69 dpy-18 hermaphrodites, non-Lon non- Dpy progeny from dpy-17 lon-1/n1950 dpy-18 hermaphrodites, Unc-49 progeny from unc-69/n1950 unc-49 heterozygous hermaphrodites, non-Unc progeny of wild-type (N2) males crossed with unc-69 n1950 hermaphrodites, and n1950 self-progeny from n1950 homozygous hermaphrodites.

For the pharyngeal and head corpses in Table 1c, only young larvae with four cells in the gonad, that is, between hatching and the middle of the first larval stage, were scored (Kimble and Hirsh, *Dev. Biol.* 70:396–417 (1979)). For ventral cord corpses (descendants from the blast cells P9–P12) and for tail corpses, third larval stage animals were scored. Extra cells are the number of extra cells among the descendants of P9, P10, and P11. The divisions of these blast cells generate four programmed cell deaths in the wild-type (FIG. 6a).

In Table 1d, HSN missing (%) is the percent of missing or grossly displaced HSN neurons. only first or second larval stage animals were scored. There are two HSNs per animal, one on each side (White et al., *Phil. Trans. R. Soc.* B311:1–340 (1986)). To score egg laying, staged worms were grown at 20° C. Animals were observed using a dissecting microscope on the second day of adulthood, and those bloated with late-stage eggs were considered egg-laying-defective (Trent and Horvitz, *Genetics* 104:619–647 (1983)). The alleles used were: ced-1(e1735), ced-3(n717), ced-4(n1162), ced-5(n1812), ced-9(n1950), dpy-17(e164), dpy-18(e364), egl-1(n478sd. ts), lon-1(e1820), unc-36 (e251). eT1(e873), a translocation chromosome with a breakpoint that disrupts-unc-36 gene function, prevents crossing over on the right arm of chromosome III (Rosenbluth and Baillie, *Genetics* 99:415–428 (1981)). nDf40 is a new deficiency which was isolated as a cis-acting suppressor of n1950.

Animals were anaesthetized with 30 mM $NaN_3$ (Avery and Horvitz, *Cell* 51:1071–1078 (1987)) and observed using Nomarski optics microscopy (Sulston and Horvitz, *Devl. Biol.* 56:110–156 (1987)). Average numbers are shown with, if appropriate, their 95% confidence limits, as determined by the t-test using the StatViewII program (Abacus Concepts, Berkeley, Calif.).

EXAMPLE 2

Isolation of ced-9(1f) Mutations

Because the ced-9(n1950) mutation causes a gain of gene function (see above), mutations that reduce or eliminate ced-9 activity (ced-9 loss-of-function (lf) mutations) were isolated by screening for cis-dominant suppressors of ced-9(n1950). Second mutations in ced-9 were expected to be isolated which could suppress the dominant effects of n1950 by inactivating ced-9 (FIG. 7). After screening 9,000 haploid genomes, three candidate suppressor mutations were isolated which were tightly linked to ced-9(n1950). One of these mutations, nDf40, behaved genetically as a large deletion (see below), indicating that the screening procedure should allow the isolation of mutations that completely inactivate ced-9. The other two mutations, n2077 and n2161, seem likely to be ced-9 loss-of-function alleles: these two mutations failed to complement each other while complementing recessive mutations in all known genes in this region. The n2077 and n2161 mutations mapped within 0.1 map units of the original n1950 mutation, and were obtained at a frequency of about $3 \times 10^{-4}$ per haploid genome, which is comparable to that for loss-of-function mutations in other *C. elegans* genes (Brenner, *Genetics* 77:71–94 (1974); Meneely and Herman, *Genetics*.92:99–115 (1979); Greenwald and Horvitz, *Genetics* 96:147–164 (1980)).

It was then determined that another mutation, n1653ts, which was previously isolated in an unrelated screen for mutants with displaced or missing HSN neurons (Desai et al., *Nature* 336:638–646 (1988)), was also a ced-9(lf) allele. n1653 was shown to be allelic to n2077 and n2161 based on its position on the genetic map, the similarity of its phenotype at restrictive temperature to the phenotypes of n2077 and n2161 mutants, and its failure to complement n2077 and n2161. Programmed cell deaths occurred normally in n1950 n2077/++ and n1950 n2161/++ animals, but were blocked in n1653/n1950 trans-heterozygotes. The results of this cis-trans test demonstrate that the allelic mutations n2077, n2161 and n1653 are in the ced-9 gene, which is defined by the mutation n1950, rather than in a closely linked gene.

Methods

The screen for mutations that resulted in a loss of ced-9 function (see FIG. 7) was performed as follows. The semi-dominant mutation egl-1(n487sd) causes the two HSN neurons to die by programmed cell death, so that the animal bloats with eggs (Ellis and Horvitz, *Cell* 44:817–829 (1986); Trent et al., *Genetics* 104:619–647 (1983). Because ced-9 (n1950) dominantly suppresses egl-1(n487) by preventing the deaths of the HSN neurons, only animals that do not have ced-9(n1950) function will bloat with eggs as a result of the egl-1 mutation. Such egg-laying defective animals were screened by mating egl-1(n487) V males either with unc-69(e587) ced-9(n1950) III; unc-10(e102) xol-1(y9) dpy-6 (e14) X hermaphrodites or with unc-69(e587) ced-9(n1950) dpy-18(e364) III; lon2(e678) xol-1(y70) X hermaphrodites. Egg laying-defective cross-progeny were picked and their progeny examined for any unusual phenotype. The xol-1 mutation on the X chromosome causes male lethality (Miller et al., *Cell* 55:167–183 (1988) and so prevents mating among $F_1$ animals, which would complicate genetic analysis of new mutations. The unc-69, dpy-18, lon-2, unc-10, and dpy-6 mutations were used as closely linked genetic markers to identify the chromosomes carrying the ced-9 and xol-1 mutations. General genetic methods and techniques for mutagenesis with ethyl methanesulphonate are described in Brenner, *Genetics* 77:71–94 (1974). Two-factor mapping experiments showed the new mutations n2077 and n2161 to be tightly linked to ced-9(n1950). This screen also generated nDf40, a deficiency that fails to complement unc-69, ced-9, unc-49 and several adjoining genes. The loss-of-function mutation ced-9(n1950 n2077) complements the nearby mutations unc-50(e306), ooc-4(e2078) and emb-25(g45ts); ced-9(n1653ts) complements unc-69(e587). The ooc-4 mutation causes a defect in oogenesis, resulting in hermaphrodite sterility. The mutation emb-25(g45ts) is described in Cassada et al., *Dev. Biol.* 84:103–205 (1981). All other mutations are described in Brenner (1974) supra.

EXAMPLE 3

The ced-9(lf) Alleles Cause Ectopic Cell Deaths

Animals homozygous for ced-9(lf) mutations show several defects (Table 2). Most obviously, homozygous ced-9 (lf) mutants derived from ced-9(lf)/+ heterozygous mothers hatch and grow to normal size, but generate very few eggs (partial sterility), all of which eventually die, usually during embryogenesis (maternal effect lethality). Furthermore, such first generation ced-9(lf) animals lack many cells normally present in wild-type animals, resulting in a number of additional defects. For example, many ventral cord motor neurons involved in the control of movement are missing, resulting in uncoordinated body movement. The HSN neurons are missing in hermaphrodites, causing an egg-laying defect (Table 2). Similarly, cells are absent from the male tail, resulting in missing or deformed rays (Table 2). Furthermore, several neurons are sometimes missing from the lumbar ganglion, although their absence does not result in an obvious behavioral abnormality.

To determine why cells are missing, ced-9(lf) animals were observed as they developed. The pattern of cell divisions in wild-type C. elegans is highly reproducible among individuals, and deviations from the normal cell lineage can be identified (Sulston and Horvitz, Dev. Biol. 56:110–156 (1971); Sulston et al., Dev. Bio. 100:64–119 (1983); Kimble and Hirsh, Dev. Biol. 70:396–417 (1979); Sulston et al., Devl. Biol. 78:542–576 (1980)). The studies revealed that many cells that normally survive in wild-type animals instead undergo programmed cell death in ced-9(lf) animals.

For example, the divisions of the 12 ventral cord blast cells P1–P12 (collectively called Pn) were monitored. During the first larval (L1) stage, each P cell divides to generate an anterior daughter (Pn.a) that is a neuroblast and a posterior daughter (Pn.p) that is a hypodermal blast cell. The Pn.a cells then follow identical patterns of divisions to generate motor neurons involved in locomotion (Sulston and Horvitz (1977) supra; White et al., Phil. Trans. R. Soc. 311:1–340 (1986); Chalfie and White, in: The Nematode Caenorhabditis elegans (eds. Wood et al.), p.337–391 Cold Spring Harbor Laboratory Press, New York, 1988). Numerous ectopic cell deaths were observed in all Pn.a lineages of ced-9(lf) animals, and frequently all descendants of the Pn.a neuroblasts died.

Ectopic programmed cell death was also observed in the ray lineages. Rays are simple sensory structures located in the male tail, which is used for copulation. Each of the 18 rays arises from a single ray precursor cell (Sulston and Horvitz (1977) supra). Many ectopic cell deaths occurred in the ray lineages of ced-9(lf) males. These ectopic deaths often eliminated the ray structure cell, which is required for ray formation (Sulston and Horvitz (1977) supra). Thus, these deaths account for the absence of rays in ced-9(lf) males.

To determine the cause of the maternal-effect lethality of ced-9(lf) mutations, the embryonic cell lineages of the progeny of ced-9(lf) animals were studied. Embryos generated by mothers homozygous for the weak allele ced-9 (n1950 n2161) usually arrested during the early stages of embryo elongation (about 450 minutes after fertilization; Sulston et al. (1983) supra), although there was some variation from animal to animal. These embryos developed normally to about the 200-cell stage, at which point extensive ectopic cell deaths began to appear. These ectopic cell deaths were morphologically similar to the cell deaths that occur during normal C. elegans development and that also first appear at this stage (Sulston et al. (1983) supra). The cell lineage of a single ced-9(n1950 n2161) embryo was analyzed using a 'four-dimensional'-microscope (which allows time-lapse recording of multiple focal planes of a specimen. 49 of the cells that died (more than 100 cells died eventually) were identified. Of these 49 dying cells, 45 normally survive in the wild-type. These 45 ectopic deaths prevented the generation of 78 cells, 50 of which would have been neurons or glial cells. Mothers of hypodermal cells and of muscle cells, also died. No obvious pattern to the ectopic cell deaths could be discerned. Many of these deaths involved cells that in the wild-type do not generate any descendants that die. Therefore, these deaths were not simply consequences of premature activation of the pathway for programmed cell death.

Embryos from mothers homozygous for the strong allele ced-9(n1950 n2077) were also studied. The n2077 mutation probably results in a complete or nearly complete inactivation of ced-9, because n2077 behaves like the ced-9 deletion nDf40 when placed in trans to each of the ced-9 alleles (Table 2). Surprisingly, the defects and terminal phenotype associated with this allele were quite different from those of n1950 n2161 embryos. The $F_2$ n1950 n2077 embryos arrested much earlier in development, with different individuals having from a few dozen to a few hundred cells at most. The embryos invariably looked sick, with swollen cells and abnormal granules in the cytoplasm. Furthermore, cell divisions were slow and asynchronous. In those rare animals that developed sufficiently far before arresting, cell corpses started to appear at about the same stage as in n1950 n2161 embryos. The lineage of a single ced-9(n1950 n2077) embryo was followed with the four-dimensional-microscope. This embryo arrested with 57 cells. Nothing resembling a programmed cell death was observed. However, blocks in mitosis and cytokinesis were apparent, with incomplete cytokineses resulting in the formation of several binucleate cells. It is not known whether these defects in cell divisions and the general sickness are effects of a lack of ced-9 function in the embryo or are secondary consequences of abnormalities in the maternal germline. Because all of these defects are completely suppressed by mutations in ced-3 or ced-4 (see below), it seems likely that they are a consequence of the ced-9(n1950 n2077) allele rather than of another mutation carried in this strain. It is likely that these defects are caused by the ectopic activation of the pathway for programmed cell death in the maternal germline. Alternatively, the three genes ced-9, ced-3 and ced-4 might act not only in programmed cell death but also in an aspect of early C. elegans development that is unrelated to programmed cell death.

Methods

The loss of ced-9 function results in ectopic cell deaths. Cell lineages of the ventral cord blast cells P1–P12 in the wild-type (Sulston and Horvitz, Dev. Biol. 56:110–156 (1977)) and cell lineages of P1–P12 in a ced-9(n1950 n2077) hermaphrodite progeny of a gC1/unc-69 ced-9 (n1950 n2077) heterozygous mother were studied. The exact pattern of cell deaths varied slightly among the three mutant animals studied. Ray lineages in the wild-type (Sulston and Horvitz (1977) supra; Sulston et al., Dev. Biol. 78:542–576 (1980)) were examined, as well as cell lineages of the left and right R cells, R4L–R9L and R4R–R9R, respectively, in a single ced-9(n1950 n2077) male progeny of a gC1/unc-69 ced-9(n1950 n2077) heterozygous mother crossed with males of identical genotype. The left and right R1–R3 cell lineages were not followed in this particular animal. As in the ventral cord lineages, the exact pattern of ectopic cell deaths varied among the three mutant animals studied. Also examined were male tails. Unc-69 male tails had nine rays on each side. The male tail of a particular unc-69 ced-9 (n1950 n2077) animal has only three rays on the left side and five on the right side. A ced-4 unc-69 ced-9(n1950 n2077) male tail showed 18 rays. In wild-type embryos, 350 minutes after fertilization, only a few cell corpses could be seen in ventral view. In ced-9(n1950 n2161) embryos, generated by a ced-9(n1950 n2161) mother, many corpses could be seen 350 minutes after fertilization.

Cell lineages were followed using Nomarski optics microscopy (Sulston and Horvitz (1977) supra). Four-dimensional-microscopy of embryos was done as follows: freshly fertilized embryos were mounted for observation on 5% agar pads in a drop of M9 or egg salts (Sulston et al., Dev. Biol. 100:64–119 (1983)). Pictures of the developing embryos were taken in 18 focal planes (roughly 1 µm apart)

at 30 second intervals using an apparatus developed by J. G. White and stored on a 12-inch optical video disk for subsequent analysis.

The data for Table 2 were obtained as follows. For Table 2a, the numbers of eggs laid by first generation ced-9(lf) hermaphrodites and the stages of development at which the progeny of these hermaphrodites arrested were examined. First generation hermaphrodites were transferred to fresh plates every 12 hours, and the number of eggs they laid were counted. Note that the absence of HSNs retards but does not prevent egg-laying (Trent et al., Genetics 104:619–647 (1983)), so that the sterility observed in ced-9(lf) animals as reflected by the number of eggs laid per animal cannot be only an effect of the defect in egg release. For example, egl-1(n487sd. ts) animals, which are egg laying-defective because they lack HSNs, nonetheless lay an average of 204 eggs (Desai and Horvitz, Genetics 121:703–721 (1989)). Egg-laying defective ced-9(lf) animals do, however, fertilize a few eggs that are never laid. For example, although wild-type hermaphrodites lay all fertilized eggs within 4 days of reaching adulthood, by the seventh day ced-9(n1950 n2077) hermaphrodites still had 1.7±1.3 eggs (number of broods=12) remaining in utero, and egg-laying defective ced-9(n1950 n2161) hermaphrodites had 30±23 eggs (number of broods=6). The number of eggs laid by ced-9(lf) animals therefore usually slightly underestimates actual brood size. The percent of eggs laid that hatched within 48 hours of removal of the mother were examined; wild-type eggs hatch about 14 hours after fertilization (Sulston and Horvitz, Devl. Biol. 100:64–119 (1983)). The percent of hatched progeny that failed to develop past the first (L1) larval stage within 6 days of hatching were also examined; wild-type larvae remain in the L1 stage for about 12 hours (Sulston and Horvitz, Devl. Biol. 100:64–119 (1983)).

For Table 2b, the percent of animals defective in egg-laying was scored as in Table 1. Note however that for some genotypes (marked †) a significant fraction of the animals could not be scored accurately for egg-laying capability because of the small numaber of eggs they generated. Egg-laying defective ced-9(lf) animals do lay eggs in the presence of serotonin (assayed as in Trent et al., Genetics 104:619–647 (1983)), suggesting that the serotonergic HSN neurons are defective or absent.

For Table 2c, young adult males were anaesthetized in 30 mM NaN$_3$, placed on their backs and observed using Nomarski optics. All strains were homozygous (nDf40 strains were hemizygous) for the closely linked mutation unc-69(e587), which facilitates identification of the chromosome carrying the ced-9 mutation. All ced-9(lf) were maintained as heterozygous stocks balanced by the chromosome III balancer gC1. The nDf40 chromosome was marked with dpy-18(e364). nDf40 fails to complement both ced-9 and unc-69. For the n2161/n2077 and n1653/n2077 trans-heterozygotes, the maternally-inherited n2077 chromosome was marked with the dpy-18(e364) mutation to distinguish self- from cross-progeny. The HSN counts for the n2161/n2077 and n1653/n2077 genotypes were not determined because of the difficulty of scoring the Dpy phenotype in early larvae. The ced-9(+)/Df larvae that arrested as L1s did so as a consequence of the unc-69(e587) mutation, which decreases brood size and results in an incompletely penetrant L1-arrest phenotype when heterozygous with nDf40; by contrast, nDf40/unc-69(+) animals do not arrest development as L1 larvae.

EXAMPLE 4

The ced-9 Gene Antagonizes ced-3 and ced-4

Figure 8:
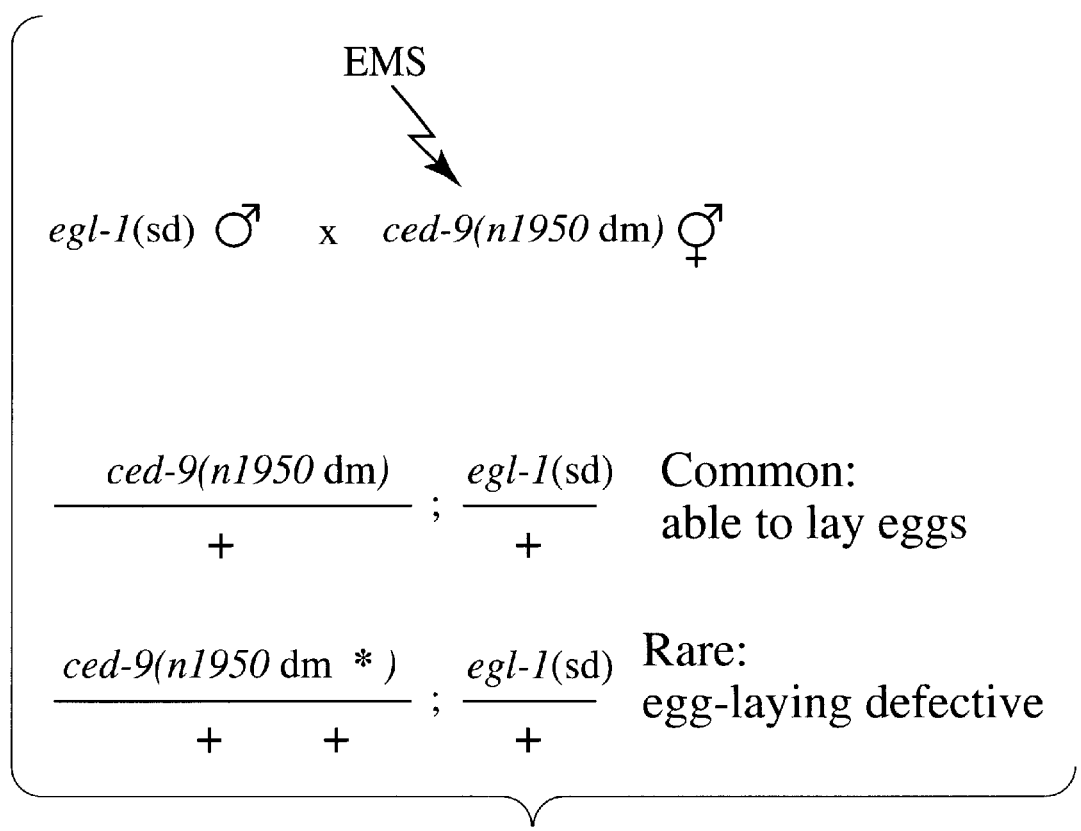
FIG. 8 shows the screen for mutations that result in a loss of ced-9 function.

If the defects associated with a loss of ced-9 function are caused entirely by the aberrant activation of the programmed cell death pathway, then mutations that prevent the process of programmed cell death might be able to suppress these defects. To test this hypothesis, double mutants were constructed using ced-9(n1950 n2077) and mutations in either ced-3 or ced-4, two genes required for programmed cell death (Ellis and Horvitz, Cell 44:817–829 (1986)). Mutations in ced-3 or ced-4 completely suppressed all defects observed in ced-9(n1950 n2077) animals (Table 3, FIG. 8g). Similar results were obtained for ced-9(n1950 n2161) and ced-9(n1653ts). These observations suggest that the defects seen in ced-9(lf) animals are indeed caused by the activation of the programmed cell death pathway. Furthermore, if these three genes are part of a regulatory pathway, these results indicate that ced-9 acts before ced-3 and ced-4, because the activities of these genes are required for ced-9(lf) mutations to have their effects.

Methods

The data for Table 3 were obtained as follows. The numbers of eggs laid were determined as described for Table 2. Viable progeny are the number of progeny that grew to the fourth larval (L4) stage within 10 days of hatching (this value includes a few animals that developed from eggs that hatched internally); wild-type larvae reach the L4 stage within 2 days. (Sulston and Horvitz, Devl. Biol. 56:110–156 (1977)). Confidence limits (95%) were determined as in Table 1. Note that ced-3 and ced-4 are able to suppress the ced-9(lf) zygotic defects in a semidominant fashion: animals homozygous for ced-9(n1950 n2077) but carrying only one wild-type copy of either the ced-3 of ced-4 genes showed milder zygotic defects than did animals with two wild-type copies of both genes, suggesting that lowering ced-3 or ced-4 activity can compensate for lower levels of the Ced-9 protein in first generation ced-9(lf) animals. However, one copy of ced-3 or ced-4 is not sufficient to suppress the maternal-effect lethality: all the viable progeny generated from ced-9(lf); ced-3/+ mothers were homozygous for the ced-3 mutation. Double mutants were also constructed between ced-9(n1950 n2077) and ced-3(n718), ced-3 (n1040), ced-3(n1128), ced-3(n1949), ced-4(n1894), or ced-4(n1920), and between ced-9(n1950 n2161) and ced-3 (n717), ced-4(n1162), ced-4(n1894), or ced-4(n1920). All of these double mutants were both viable and fertile, showing that the suppression of the ced-9(lf) defects by ced-3 and ced-4 is not allele-specific.

EXAMPLE 5

Cloning and Sequencing the ced-9 Gene and cDNA

Cloning of ced-9 ced-9 was genetically mapped to the right arm of chromosome III, approximately 0.05 map units to the right of unc-69. This position placed ced-9 between the two cloned genes lin-12 and tra-1. The whole interval between these two genes, corresponding to approximately 2 Mb, had previously been cloned as part of the C. elegans physical mapping effort (Coulson et al., Proc. Natl. Acad. Sci. USA 85:4397–4401 (1986); Coulson et al., Nature 335:184–186 (1988); Coulson et al., BioEssays 13:413–417 (1991)). To narrow down the region containing ced-9, ced-9 was mapped with respect to a series of restriction fragment length polymorphisms (RFLPs) between the common laboratory strain Bristol N2, and RC301, a strain isolated from the wild near Freiburg, Germany.

Figure 9:
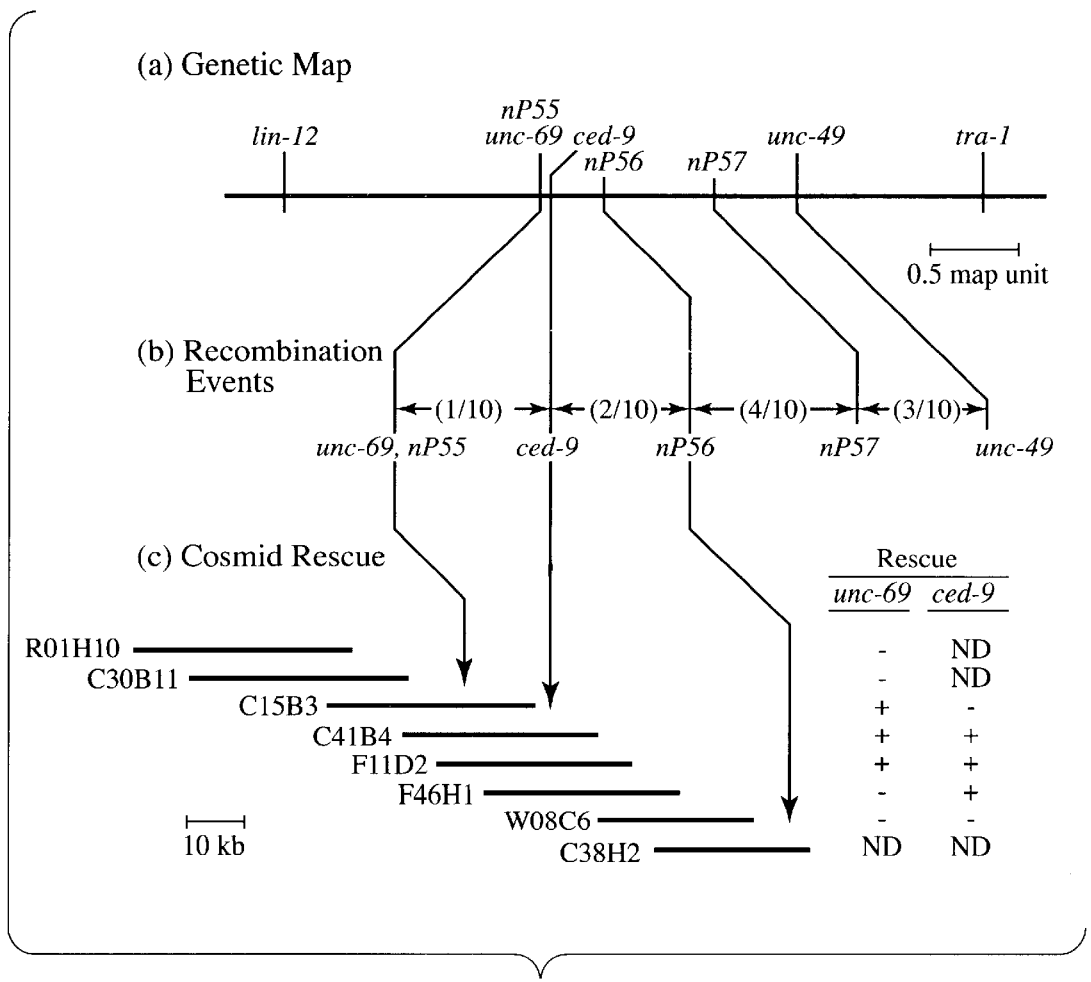
FIG. 9 is a diagram of the ced-9 cloning strategy and cosmid rescue. a) Genetic map of the ced-9 region. Relevant genes as well as the approximate position of the N2/RC301 restriction fragment length polymorphisms (RFLPs) used to map ced-9 are shown. b) Number of recombination events observed between various markers in the unc-69 to unc-49 interval. The nP55 polymorphism did not separate from unc-69 in these experiments, suggesting that unc-69 is to the right, or close and to the left of nP55. c) Cosmid rescue of unc-69 and ced-9. Cosmids situated between the nP55 and nP56 RFLPs (recognized by cosmids C15B3 and C38H2, respectively) were injected into unc-69 or unc-69 ced-9/++ animals, and established transgenic lines were tested for rescue of the unc-69 and ced-9 phenotypes. ND: not determined.
Figure 10:
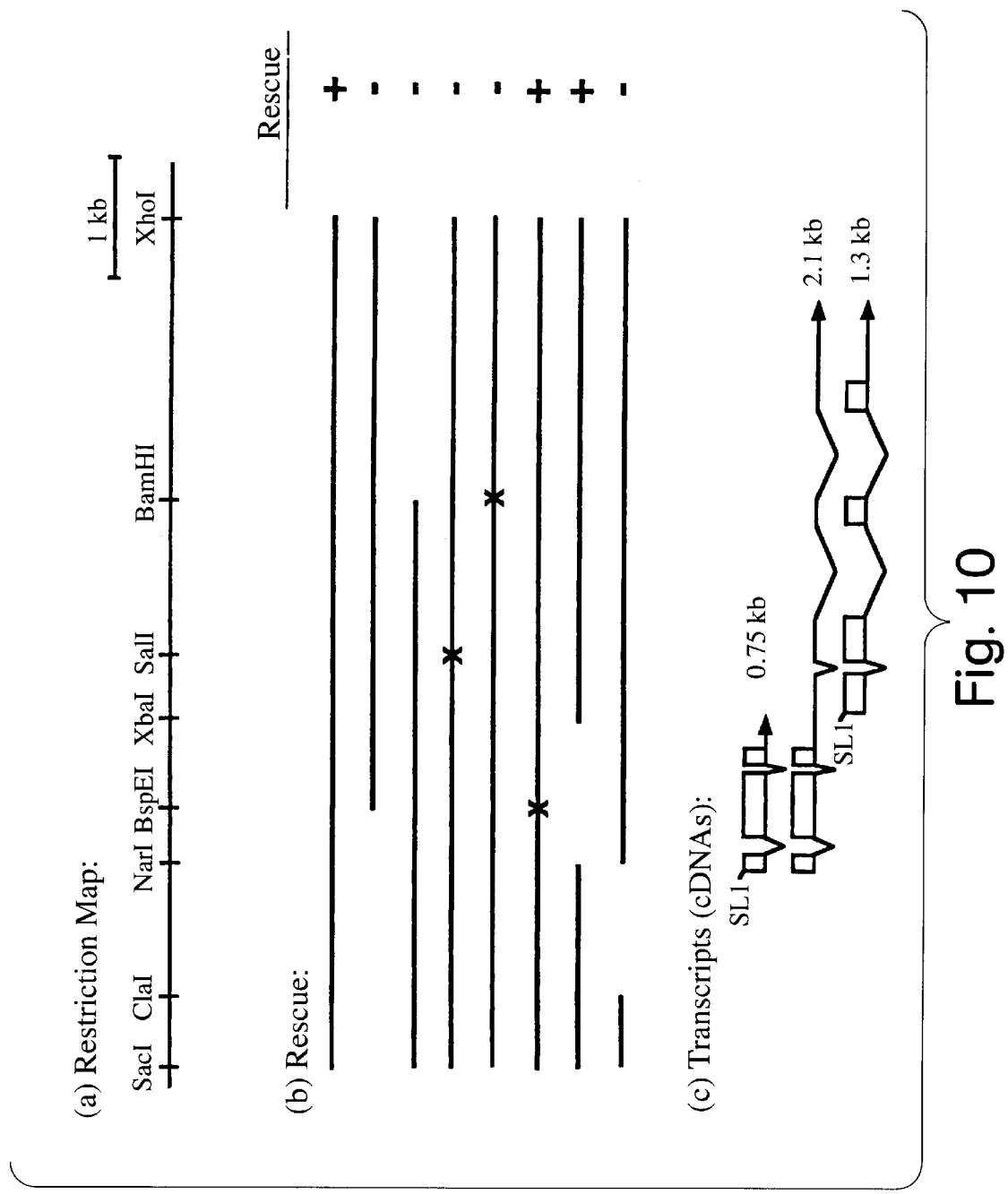
FIG. 10 shows the ced-9 locus. a) Restriction map. b) Rescue ability of deletions and point mutations in the locus. c) ced-9 transcripts and location of introns and exons.

Mapping of ced-9 with respect to these RFLPs (FIG. 9b) localized the gene to a roughly 60 Kb interval located between nP55 and nP56. Cosmids from this region were then tested for their ability to rescue the ced-9(lf)-associated defects. Three overlapping cosmids were found to be able to rescue ced-9 (FIG. 9c). Various fragments from the region common to all three cosmids were subcloned into plasmids and tested for rescue activity. A 4.7 Kb SacI-XhoI fragment was identified in this manner that efficiently rescued both the sterility and the lethality of ced-9(n1950 n2077) mutants. Further deletions into this fragment from either the right or the left abolished or greatly diminished the rescuing the activity of the fragment (FIG. 10b).

ced-9 cDNAs

A 4.2 Kb CaI-XhoI fragment was used to probe a *C. elegans* cDNA library. Three distinct classes of cDNAs were isolated, corresponding to the 0.75 Kb, 1.3 Kb, and 2.2 Kb transcripts identified on Northern blots. One cDNA of each class was sequenced. The deduced intron/exon structure of the three classes of cDNAs is shown in FIG. 10c. Both the 0.75 Kb and 2.3 Kb cDNAs sequenced had SL1 trans-spliced leaders at their 5' ends, suggesting that full-length cDNAs were isolated. The three cDNA classes are related to each other in an unusual way: the 0.75 and 2.2 Kb transcripts share the same 5' end and open reading frame and are predicted to encode identical proteins. The 1.3 Kb and 2.2 Kb transcripts are predicted to share the same polyadenylation site.

METHODS

Mutations and Strains

All mutations were generated in a Bristol N2 background, which was used as the standard wild-type strain, except where noted. The following mutations were used: LGIII: unc-69(e587), ced-9(n1950dm), ced-9(n1950 n2077), ced-9 (n1950 n2161), unc-49(e382).

Mutations other than ced-9 are described in (Brenner, *Genetics* 77:71–94 (1974)). The ced-9(n1950 n2077) and ced-9(n1950 n2161) mutations were maintained as balanced strains over the LGIII balancer gC1, which carries the mutations dpy-19(e1259ts,mat) glp-1(q339) Strains were maintained as described (Brenner, 1974 supra). All strains were grown at 20° C.

RFLP Mapping

Various cosmids from the lin-12 to tra-1 interval were tested for their ability to detect RFLPs between the common laboratory strain N2 and various strains isolated from the wild and known to contain a large number of transposon-induced RFLPS. The position of ced-9 was then determined relative to these markers as described (Ruvkun et al., *Genetics* 121:501–516 (1989)). Briefly, N2/RC301 recombinants in the ced-9 region were obtained by mating RC301 males with unc-69(e587) ced-9(n1950) unc-49(e382) hermaphrodites to generate unc-69 ced-9 unc-49 [N2]/+++[RC301] heterozygotes. From these heterozygotes, Unc-49 non-Ced-9 non-Unc-69 and Unc-49 Ced-9 non-Unc-69 recombinants were cloned, homozygozed for the recombinant chromosome, and the genotype of the various RFLP loci analyzed by genomic Southern blot analyses.

Germline Transformation of ced-9 Mutants

DNAs to be tested for ced-9 rescue activity were micro-injected into the mitotic germline of hermaphrodites according to the method developed by Mello and colleagues (Mello et al., *EMBO J*. 10:3959–3970 (1991)). The relevant DNA was injected at a concentration of 5–25 µg/ml. pRF4, a plasmid containing a dominant rol-6 mutation, was co-injected as a dominant marker to identify transgenic animals. Since ced-9(lf) mutants are almost sterile and produce only dead progeny, heterozygotes of genotype gC1 dpy-19(e1259)/unc-69(e587) ced-9(n1950 n2077) were injected, where the unc-69 was used as a linked marker to identify the ced-9 chromosome. Non-Unc non-Dpy Roller F1s were picked to establish stably transmitting roller lines. From these, Roller Unc-69 animals were picked and tested for rescue of the ced-9(lf)-associated sterility and maternal effect lethality. A clone was considered to rescue if a stable homozygous line of genotype unc-69 ced-9(lf) III; array could be established.

Molecular Biology

Standard molecular biology protocols (see (Sambrook et al., *Molecular Cloning: A Laboratory Manual*, Cold Spring Harbor Laboratory, 1989) was followed except where noted. All plasmid subcloning was done into pBluescript vectors (Stratagene).

The 4.7 Kb genomic SacI-XhoI fragment with rescuing ability was subcloned into pBluescript II (Stratagene) and both strands were sequenced using the ExoIII-S1 nested deletion method and T7 polymerase (Sequenase, USB) following the protocol suggested by the manufacturer.

A 4.2 Kb ClaI-XhoI rescuing genomic fragment was used to probe a λ cDNA library. From approximately 300,000 plaques, 11 cDNAs were isolated. The sequences present at the ends of the inserts were determined for all 11 cDNAs. 8 cDNAs corresponded to the 0.75 Kb cytochrome b560-like transcript, two (one incomplete) were from the 1.3 Kb ced-9 transcript, and one corresponded to the 2.2 Kb "fusion" transcript. One cDNA from each class was then completely sequenced (one strand only).

TABLE 1

The Gain-of-Function Allele ced-9(n1950) Prevents Programmed Cell Deaths a. ced-9(n1950) prevents programmed cell deaths

| Maternal genotype | Zygotic genotype | Extra cells in anterior pharynx | No. of Animals |
| --- | --- | --- | --- |
| ced-3/ced-3 | ced-3/ced-3 | 12.5 ± 0.7 | 30 |
| ced-4/ced-4 | ced-4/ced-4 | 13.9 ± 0.5 | 40 |
| ced-9(n1950)/ced-9(n1950) | ced-9(n1950)/ced-9(n1950) | 13.3 ± 0.6 | 45 | b. ced-9(n1950) is a dominant gain-of-function mutation and shows a maternal effect

| Maternal genotype | Zygotic genotype | Extra cells in anterior pharynx | No. of Animals |
| --- | --- | --- | --- |
| +/+ | +/+ | 0.03 ± 0.05 | 60 |
|  | Df/+ | 0.00 | 50 |
|  | ced-9(n1950)/+ | 5.3 ± 0.8 | 25 |

TABLE 1-continued

The Gain-of-Function Allele ced-9(n1950) Prevents Programmed Cell Deaths

| ced-9(n1950)/+ | +/+ | 0.2 ± 0.22 | 25 |
| | ced-9(n1950)/+ | 11.4 ± 0.8 | 30 |
| | ced-9(n1950)/ced-9(n1950) | 13.7 ± 0.5 | 30 |
| ced-9(n1950)/ced-9(n1950) | ced-9(n1950)/+ | 11.8 ± 0.6 | 30 |
| | ced-9(n1950)/ced-9(n1950) | 13.3 ± 0.6 | 45 | c. ced-9(n1950) suppresses the accumulation of cell corpses

| Genotype | Corpses Pharynx | n | Corpses Head | n | Corpses P9–P11 | Corpses P12 | Corpses Tail | Extra Cells P9–P11 | n |
|---|---|---|---|---|---|---|---|---|---|
| Wild-type (N2) | 0 | 50 | 0.0 ± 0.1 | 50 | 0 | 0 | 0 | 0 | 30 |
| ced-1 | 0.8 ± 0.2 | 100* | 28 | 10† | 3.5 ± 0.3 | 1.7 ± 0.3 | 1.7 ± 0.3 | 0.4 ± 0.3 | 30 |
| ced-1; ced-3 | 0.02 ± 0.04 | 50 | 0.3 ± 0.1 | 50 | 0.03 ± 0.07 | 0 | 0.3 ± 0.2 | 3.9 ± 0.1 | 30 |
| ced-1; ced-4 | 0.02 ± 0.04 | 50 | 0.7 ± 0.2 | 50 | 0.03 ± 0.07 | 0 | 0.3 ± 0.2 | 4.0 ± 0.1 | 30 |
| ced-1; ced-9(n1950) | 0 | 30 | 0.5 ± 0.3 | 30 | 0 | 0 | 0.3 ± 0.2 | 4.0 ± 0.1 | 30 |
| ced-5 | 3.6 ± 0.6 | 25 | 16 ± 5 | 10 | 3.0 ± 0.5 | 2.2 ± 0.3 | 4.6 ± 0.8 | 0.2 ± 0.2 | 21 |
| ced-5; ced-3 | 0.1 ± 0.1 | 40 | 0.5 ± 0.2 | 40 | 0.05 ± 0.10 | 0 | 0.4 ± 0.4 | 3.9 ± 0.1 | 20 |
| ced-4; ced-5 | 0.2 ± 0.2 | 40 | 1.0 ± 0.3 | 40 | 0.05 ± 0.10 | 0 | 1.6 ± 0.5 | 3.9 ± 0.2 | 20 |
| ced-9(n1950); ced-5 | 0.1 ± 0.1 | 100 | 0.8 ± 0.4 | 25 | 0 | 0 | 1.1 ± 0.3 | 3.8 ± 0.1 | 30 | d. ced-9(n1950) prevents the deaths of the HSN neurons in egl-1 mutants

| Genotype | HBNs missing (%) | No. of sides | Egg-laying defective (%) | n |
|---|---|---|---|---|
| Wild-type (N2) | 1 | 250 | 0.4 | 704 |
| egl-1 | 99 | 200 | 99 | 447 |
| ced-3; egl-1 | 0 | 160 | 0.2 | 599 |
| ced-4; egl-1 | 0 | 100 | 0 | 417 |
| ced-9(n1950); egl-1 | 0 | 200 | 0 | 417 | a. The genotypes of animals studied were as shown.
b. The complete genotypes are given in Example 1.
c. Extra cells, number of extra cells among the descendants of P9, P10, and P11. n, number of animals scored.
*Data from Ellis et al., Genetics 129:79–94 (1991). †Data from Ellis and Horvitz, Cell 44:817–829 (1986).
d. HSN missing (%), percent of missing or grossly displaced HSN neurons. No. of sides, number of sides scored.
n, number of animals scored.
Average numbers are shown with, if appropriate, their 95% confidence limits.

TABLE 2

Phenotypes of ced-9(1f) Mutants

| Genotype* | ced-9(+) 20° C. | ced-9(+) Df 20° C. | n1950 n2161 15° C. | n1950 n2161 20° C. | n1950 n2161 23° C. | n1950 n2161 25° C. | n1950 n2161 Df 20° C. |
|---|---|---|---|---|---|---|---|
| (a) Sterility and maternal-effect lethality | | | | | | | |
| Eggs laid per animal | 209 ± 33 | 202 ± 60 | 117 ± 36 | 97 ± 31 | 45 ± 22 | 6.3 ± 4.5 | 23 ± 14 |
| Hatching (%) | 99 ± 1 | 75 ± 2 | 12 ± 3 | 2.4 ± 0.7 | 0.4 ± 0.4 | 0 | 0 |
| L1 arrest (%) | 0 | 13 ± 3 | 100 | 100 | 100 | NA | NA |
| | n = 14 | n = 9 | n = 23 | n = 42 | n = 36 | n = 60 | n = 50 |
| (b) Egg-laying defect | | | | | | | |
| Egg-laying defective (%) | 0 | 0 | 64 ± 16 | 76 ± 13 | 94 ± 7 | 98 ± 3 | 96 ± 4 |
| | n = 100 | n = 35 | n = 23 | n = 42 | n = 36 | n = 60 | n = 50 |
| HSNs missing (%) | 0 | 0 | 77 | 87 | 94 | 95 | 95 |
| | n = 100 | n = 48 | n = 118 | n = 138 | n = 100 | n = 130 | n = 60 |
| (c) Absence of rays in male tails | | | | | | | |
| Rays per side | 8.9 ± 0.1 | 8.6 ± 0.2 | 8.0 ± 0.3 | 6.6 ± 0.3 | 5.9 ± 0.3 | 5.4 ± 0.4 | 6.0 ± 0.3 |
| | n = 68 | n = 34 | n = 40 | n = 40 | n = 58 | n = 34 | n = 62 |

| Genotype* | n1950 n2161 n1950 n2077 20° C. | n1653ts 25° C. | n1653ts Df 25° C. | n1653ts n1950 n2077 25° C. | n1950 n2077 20° C. | n1950 n2077 Df 20° C. |
|---|---|---|---|---|---|---|
| (a) Sterility and maternal-effect lethality | | | | | | |
| Eggs laid per animal | 40 ± 9 | 2.7 ± 1.1 | 0 | 0.3 ± 0.4 | 1.6 ± 1.4 | 0.8 ± 1.6 |
| Hatching (%) | 0 | 38 ± 24 | NA | 0.7 ± 1.4 | 0 | 0 |

TABLE 2-continued

Phenotypes of ced-9(1f) Mutants

| | | | | | | |
|---|---|---|---|---|---|---|
| L1 arrest (%) | NA | 40 ± 36 | NA | 100 | NA | NA |
| | n = 49 | n = 26 | n = 15 | n = 30 | n = 20 | n = 24 |
| (b) Egg-laying defect | | | | | | |
| Egg-laying defective (%) | 96 ± 6 | NA† | NA† | NA† | NA† | NA† |
| | n = 40 | | | | | |
| HSNs missing (%) | ND | ND | ND | ND | 99 | 100 |
| | | | | | n = 220 | n = 42 |
| (c) Absence of rays in male tails | | | | | | |
| Rays per side | 5.9 ± 0.3 | 8.6 ± 0.2 | 7.6 ± 0.3 | 8.1+0.3 | 4.6 ± 0.3 | 4.9 ± 0.6 |
| | n = 38 | n = 38 | n = 44 | n = 52 | n = 81 | n = 26 | a. Hatching (%), percent of eggs laid that hatched within 48 hours of removal of the mother. L1 arrest (%), percent of hatched progeny that failed to develop past the first (L1) larval stage within 6 days of hatching. n, number of broods analysed.
b. For some genotypes (marked †) a significant fraction of the animals could not be scored accurately for egg-laying capability. n, number of animals scored. HSN missing (%), percent of missing or grossly displaced HSN neurons. n, number of sides scored.
c. Rays per side, number of rays present per side in the male tail. n, number of sides scored. Confidence limits (95%) were determined as in Table 1. NA, not applicable. *All strains were homozygous (nDf40 strains were hemizygous) for the closely linked mutation unc-69(3587).

TABLE 3

Mutations in ced-3 and ced-4 Suppress the Defects Resulting From the Loss of ced-9 Function

| | Sterility and maternal-effect lethality | | | Egg-laying defect | | Male tail | |
|---|---|---|---|---|---|---|---|
| | Eggs laid | | | Egg-laying | | | |
| Genotype* | per animal | Viable progeny | n | defective (%) | n | Rays per side | n |
| ced-9(+) | 207 ± 36 | 207 ± 33 | 14 | 0 | 100 | 8.9 ± 0.1 | 68 |
| ced-9(n1950 n2077) | 1.6 ± 1.4 | 0 | 20 | NA† | 100 | 4.6 ± 0.3 | 81 |
| ced-4 ced-9(n1950 n2077) | 200 ± 19 | 160 ± 20 | 12 | 1 | 84 | 9.0 | 42 |
| ced-4 | 182 ± 17 | 148 ± 17 | 12 | 0 | 100 | 9.0 ± 0.1 | 30 |
| + ced-9(n1950 n2077) | | | | | | | |
| ced-4 ced-9(n1950 n2077) | 56 ± 20 | 3.9 ± 2.0 | 7 | 62 | 71 | 7.4 ± 0.3 | 50 |
| ced-9(n1950 n2077); ced-3 | 154 ± 29 | 94 ± 22 | 13 | 0 | 100 | 9.0 | 28 |
| ced-3 | 178 ± 51 | 146 ± 46 | 6 | 0 | 66 | 8.9 ± 0.1 | 50 |
| ced-9(n1950 n2077); ced-3/+ | 132 ± 62 | 17 ± 6 | 10 | 18 | 40 | 8.7 ± 0.1 | 50 |

Viable progeny, number of progeny that grew to the fourth larval (L4) stage within 10 days of hatching (this value includes a few animals that developed from eggs that hatched internally);
n, number of broods analysed.
Confidence limits (95%) were determined as in Table 1.
*All strains are homozygous for the closely linked mutation unc-69(e587).
†Many animals could not be accurately scored for egg-laying.

Equivalents

Those skilled in the art will know, or be able to ascertain using no more than routine experimentation, many equivalents to the specific embodiments of the invention described herein. These and all other equivalents are intended to be encompassed by the following claims.

SEQUENCE LISTING

<160> NUMBER OF SEQ ID NOS: 8

<210> SEQ ID NO 1
<211> LENGTH: 6559
<212> TYPE: DNA
<213> ORGANISM: Caenorrhabditis elegans
<220> FEATURE:
<221> NAME/KEY: misc_feature
<222> LOCATION: (1)...(6559)
<223> OTHER INFORMATION: n = A,T,C or G

<400> SEQUENCE: 1
atcgatagtc gtcaccaaat ggattttccg atttctcact agtccatggc tcacaattta      60

-continued

```
caaaatctcg agaaaagaaa ggatgcaagg agtatgaaga ggttccgaat ctaaatattt    120
taatttaaaa aaatcaattt cgaattgaaa ttcaactcct actcgttttg aaaatgccaa    180
tcctttaagt aaacttctgg atcgcccatt tcttccagaa attccttcaa agtagtggtt    240
ttgtactgat ttcctccgca aagaatagga actttcgaat ctcctggagc gaaacgggat    300
tttsataaca aaaactatc cagacaaacc ataggacttt tcaaatatt ccttatttgg      360
ctgtccattt ggaagcaccc aatctttaac gctgtccagc cagaagtgct ccactcgcca    420
aggataaaag gctcattttt gaagccgaat tttactaaaa tctctagcca tggagtcgat    480
ggatcagaaa ttcgaggaat tttagatttc atcttgaaat ttgcaatgga aaaataatt     540
attcaaagaa aatcacagaa aatgcaacaa aaaaacaaa aaagaacaa aaacaagtc       600
gaaaagtgcg cccgggtcgt ttgctgacgc atctcttcaa acgagacgcg ctgctggcga    660
cttctcgtgc cctgtgcgtg catttccgca acaaaattca acacttgttt tgaaacgcac    720
cgccctgttt cttttttcaa ttttgataag aaaatcagca ttgtttcagg atgattaaca    780
ttccaactgc gattctgtgc cgcttgggcg ccagatcgtc gatttcccgc tcctttggaa    840
catcgatcgt caccaaggtg gggattttt gaatttttcc gtgaaaattg ttgattttt      900
gtgtacgcat gaaggagaaa tgtataacag acacattctt ttcaattaat tatttataat    960
attcacagtc cgaggcaaag acgccaatcc agaagttcgg atgggaatac ctgttgaagc   1020
agcgctccaa gaatcgccca atcgctccac atctcaccgt ctaccagcca caattgacct   1080
ggatgctctc cggattccat agaatcagcg gttgtgtaat ggccggaacc cttctcgtcg   1140
gaggaatcgg attcgcagtt ttgccgttcg atttcaccgc ttttgtggat ttcatccgta   1200
gctggaactt accatgcgcg gtgaccgctg tcttcaagta catcattgct ttccccatca   1260
ttttccatac tcttaacgga attcgcttct taggattcga tttggctaag ggagtcaata   1320
atgttggaca ggtaggagtt gaaattatta atttaattgt tttaaaataa aaattaattt   1380
tcagatctac aaatcgggat atctcgtatc tggactttcg gctattcttg ctctcgccat   1440
tgtcttcaac tcttgccaga acaagagcaa caagactgcc taggcacaga tgctccgcct   1500
tctttttct tactccgccc cagccctcga caattctcgt caatttactt ttaccgttga   1560
tttcttcgat tttctctctt tccgtagat ttacctctcc tcttcgttttt tttttctctg   1620
tctagaatgt atattatgat tatgaaaacg aataaaaatt ttagatgaca cgctgcacgg   1680
cggacaactc gctgacgaat ccggcgtatc ggcgacgaac gatggcgact ggcgagatga   1740
aggagtttct ggggataaaa ggcacagagc ccaccgattt tggaatcaat agtgatgctc   1800
aggacttgcc atcaccgagt aggcaggctt cgacgcgaag aatgtccatc ggagagtcaa   1860
ttgatggaaa aatcaatgat tgggaagagc caaggcttga tatcgaggga tttgtggtaa   1920
ttttttaatt ttttttttgta aataaaatt cctgctgctt ccaggtcgac tatttcacgc   1980
accgaatccg gcaaaacgga atggaatggt ttggagcacc gggattgccg tgtggagtgc   2040
aaccggagca cgaaatgatg cgagttatgg gaacgatatt cgagaagaag cacgcggaaa   2100
attttgagac cttctgtgag cagctgctcg cagtgcccag aatctcattt tcactgtatc   2160
aggatgtggt tcggacggtt ggaaatgcac agacagatca atgtccaatg tcttatggac   2220
gtttggtaag ggagaaaata ctgaaaaaaa gtttgcaaaa attcgaaaat tcgccagaaa   2280
ggtggcagaa aaaacatttg caaaaattgt ttgttttcct tcaggaaatc agcaaaactt   2340
ggtcaaaaat agcccaatta tgtgtctttt ttgaaagttt tccattaaaa aaccacgaat   2400
```

-continued

```
tttgatcccg gattgtaatt ttttttgttg ataaattagc agaaaacttt acgaattcga    2460
ttaaaaacgt tattttctat tcgaatattt ttaaagcata ttttccttga tttgtatttg    2520
cgaaaaagat ctgctgattt atcaaaaatc ggttttaaa tgtaaaattt gtggaaaata     2580
cattaaaatt cgattttga acttttttct tcgaaaaaca ggttttctg ctgatttgct      2640
gaacgaaaaa ccccaaaaat tcaattttcg aacattaaaa accagaaaaa tcgtttttt     2700
aagcttaatt ttccgccaga atgaacgaa ttaaattgca aatttctaat tttcagatag     2760
gtctaatctc gttcggcggt ttcgtagctg caaaaatgat ggaatccgtg gaactgcagg    2820
gacaagtgcg aaacctcttc gtttacacat cgctgttcat caaaacgcgg atccgcaaca   2880
actggaagga acacaatcgg agctgggtaa ggagtatttg catagacatt agaagtcaat   2940
atccccttt ccctagtacc cttgacttcc cggggtgttg gtaagccgat aattacaggg    3000
ttcggtagcc tcttgggggg acagctggaa acatattcaa gtatattact gtttatgata   3060
atgttattgt tacgggaata caaaattcgc agaatgctat tcacaacat atttgacgcg    3120
caaaatatcc agtagagaaa actacagtaa ttctttaaat ttttaaaatt tttacaatta   3180
aagaaaataa ccactaatca aagaaatta atttcaaaaa tcgagcccgt aaatcgacta    3240
cagtaggcat ttaaagaatt actgtagttt tcgctacgag atatttccgc ctcaaatatg   3300
ttgtgaaata cgcattcacg gattttgtg ttccccggaa tatgctctaa agcattattt    3360
gtgaaaataa aaaatcaaga aaaaaattgc aggacgactt catgacactc ggaaaacaaa   3420
tgaaagagga ctacgaacga gcagaagctg aaaagtggg acgccggaag cagaacagac    3480
ggtggtcgat gattggcgct ggagtaacag ctggagccat tggaatcgtt ggagtcgtcg   3540
tgtgtgggcg gatgatgttc agcttgaagt aacgtattca atttgtgtaa ataattaatt   3600
tatgtacaac tccttacatt tgaatctcat ttttgctcac tgattctctc atcctttgaa   3660
ctggaagaag tgggaaagct aggccacaaa ttacggctct ctgtgtcgat ttacgatttt   3720
actgcaattt tttccgattg ccttttttt tggccaaacc ctacttccgc gtaatatcaa    3780
cttttccgtg ttctgtacat ttcgtcaaaa accctgaaac cctaactttt ctcgccgtgg   3840
cctagcctcc cgcttctctt ccacatttcc aaagtacccc tgtatctcaa taattcatct   3900
tcactttaac tgtctctttt cgtgtggcct cttccaactc cccccaaatt cctgtacgcg   3960
tacgcgactt tgtatttatt ttttcaaat tgttttctct ctacaacaac aaaaaaacg     4020
gttctttat tcaacccttt tttcggaacg aaactgcaat tttgataata ggcgtgcgca    4080
agagaatccg gttttcattt tcgccatcac gtcatccaaa aaagtttagt aggaaaatat   4140
catttttaa tataatgatt catctttctc gcctcttctg tctcgagacg acggtcaatt    4200
cgatggcctt gaattttcg aaaacaaaaa tgttttgtt tagtgtaaac gatcccccg      4260
ccttatcgct gtttcaccat cagataggct ccgccatttg attcccttga attttgtcgg   4320
tatataaaac aaaaaacgtt agtgcacgat tcaaaaaaca acaatgcgtg ctttactatt   4380
cacctctgtt gttcttttgg ctttggcttt tgttgaggca aagaagcaga ctatcactgt   4440
caagggtaca actatttgta ataagaagag aattcaggmg raggttacct ttgggagaaa   4500
gatactcgtg agttttcagt cttgtttagc ttgaaacggc ttaaaaagga ctaaaaaggc   4560
ctaaaaattg aagttttcca cctgtttca aaagaaagcc gaattgcaca gctttacacg    4620
agatttctca ataatttgta tttgaaattt tcatattcat ccccaaacgt tctttacacg   4680
aaattttgcg attttgagc ttaaaatacg ataccctggtc tcgacacgaa acatttttgt    4740
taaattcaaa aagatgtgcg cctttaaaga gtgctgtagt ttgaaacttc tgttgttgcg   4800
```

-continued

```
gacttttcat cgattttcg tagcgtttt ttataagaaa aatgtattta tttattcaaa    4860
aatttaattt taccgaatcg cgaaaaacaa aatgaagaac accgataaaa atatcgcagc    4920
aacaatagtt tgaaattaca gtactctttt aaggngnnca catttcctat atttcacaca    4980
aacttgtcgt gtcgnnncng ggtatcgtca ttttgatgca gaaatcaaga aaattgcata    5040
tatgttcaaa aaaccacaat tatggcgaat ttcaagcttg aaacgaaaat tcaggaaatt    5100
ctaaaaatta aaaaaaaatc attcgaaatg tgaaatttga tattcaactt gaagtccata    5160
tggcaaattt cgtctattcc gnnnttcgan nattttgttc cacgtggccg cgaaaagaga    5220
aagcacgann actgatttct ggcaatttt tcctgtaccg tgtcaattat ttgaaactct    5280
aataagctgg tatttttctg ctattgacaa ctaactgaat ccataatttg caattataat    5340
attgactttt gatgtgtggc ttagaaaaaa aaaccaaaa acctcatcta gctttaggct    5400
gccaatatat tcctaggaca tataaaaaac ccttaaaatt tctgcaaca cctacaagct    5460 atcaaacgta ctattagtat tcaattttcc agtcgacccc gatgacaagc tcgcctcaat    5520
gcaatcgaac aaagaaggag agttctcact taccggatcc gacgacgaga tcacctcaat    5580
ctctccatac ctcataatca cccacaactg caacgtgaag aaggccggat gcaagcgtgt    5640
ttcagagtat ttgattccaa aggagaagat cggtggaacc tatgatatga catacgtcac    5700
tcttgatatt ctttccgcta aagacaagga gaagtgctaa gaaaatgttt tttttgtttg    5760
gtttgcttgt ttggaaggga aggactttct atctctttta attcaacaat aaactattgg    5820
aaaaccgttg aaattttaac cttgaactgt aagaaaagtt gcgtgattat gttgacaatt    5880
ttgccaagta tatcttttgtg gatatcacaa taaacgaagt caaagcacga aatattacgg    5940
aaacacaaaa ttaatgagaa tgcgcaacat atttgaccgc aaaatatctc gtagcgaaac    6000
tacagtaatt cttcaaaaga ctactgtagc gctgtgtcga tttacgagct cgattttga    6060 aatgaatcag actagaagaa aaggaggaaa atattgaaca tcaattgaac atcaattcaa    6120
aaagtcgaac ccttgactac agtagtcttc taaagaatta ctgtagtttt cgctacgaga    6180 tatttttgngn gtcaaatatg ttgngcaata cgcatcctca gaattgtgtg ttctcgtaat    6240
gtcttgaaaa tttccattt caacatcaaa taagcaaatc taaaaatgtg ggttctgcag    6300
cgaccactat gactgtgatc gtggcaagac ccactcagaa aactacgtgt tcctttaaac    6360
aaatacattt ttaagtattg taggtataaa aattgttggc tagcagtcta ggctgccttt    6420
ttcagtcgac aaacttctaa tttaatcggc gggtcttcaa aaagtcgttt ctttgaaaat    6480
ataaagcttt atatatttat atattaaaaa ttttgattac atgatatcaa aagcgactag    6540
tttgtataaa aattatcaa                                                6559
```

<210> SEQ ID NO 2
<211> LENGTH: 1315
<212> TYPE: DNA
<213> ORGANISM: Caenorhabditis elegans
<220> FEATURE:
<221> NAME/KEY: CDS
<222> LOCATION: (7)...(846)

<400> SEQUENCE: 2

```
tttgag atg aca cgc tgc acg gcg gac aac tcg ctg acg aat ccg gcg      48
       Met Thr Arg Cys Thr Ala Asp Asn Ser Leu Thr Asn Pro Ala
       1               5                  10 tat cgg cga cga acg atg gcg act ggc gag atg aag gag ttt ctg ggg    96
Tyr Arg Arg Arg Thr Met Ala Thr Gly Glu Met Lys Glu Phe Leu Gly
15                  20                  25                  30
```

```
ata aaa ggc aca gag ccc acc gat ttt gga atc aat agt gat gct cag      144
Ile Lys Gly Thr Glu Pro Thr Asp Phe Gly Ile Asn Ser Asp Ala Gln
             35                  40                  45 gac ttg cca tca ccg agt agg cag gct tcg acg cga aga atg tcc atc      192
Asp Leu Pro Ser Pro Ser Arg Gln Ala Ser Thr Arg Arg Met Ser Ile
             50                  55                  60 gga gag tca att gat gga aaa atc aat gat tgg gaa gag cca agg ctt      240
Gly Glu Ser Ile Asp Gly Lys Ile Asn Asp Trp Glu Glu Pro Arg Leu
             65                  70                  75 gat atc gag gga ttt gtg gtc gac tat ttc acg cac cga atc cgg caa      288
Asp Ile Glu Gly Phe Val Val Asp Tyr Phe Thr His Arg Ile Arg Gln
         80                  85                  90 aac gga atg gaa tgg ttt gga gca ccg gga ttg ccg tgt gga gtg caa      336
Asn Gly Met Glu Trp Phe Gly Ala Pro Gly Leu Pro Cys Gly Val Gln
 95                 100                 105                 110 ccg gag cac gaa atg atg cga gtt atg gga acg ata ttc gag aag aag      384
Pro Glu His Glu Met Met Arg Val Met Gly Thr Ile Phe Glu Lys Lys
                115                 120                 125 cac gcg gaa aat ttt gag acc ttc tgt gag cag ctg ctc gca gtg ccc      432
His Ala Glu Asn Phe Glu Thr Phe Cys Glu Gln Leu Leu Ala Val Pro
            130                 135                 140 aga atc tca ttt tca ctg tat cag gat gtg gtt cgg acg gtt gga aat      480
Arg Ile Ser Phe Ser Leu Tyr Gln Asp Val Val Arg Thr Val Gly Asn
            145                 150                 155 gca cag aca gat caa tgt cca atg tct tat gga cgt ttg ata ggt cta      528
Ala Gln Thr Asp Gln Cys Pro Met Ser Tyr Gly Arg Leu Ile Gly Leu
    160                 165                 170 atc tcg ttc ggc ggt ttc gta gct gca aaa atg atg gaa tcc gtg gaa      576
Ile Ser Phe Gly Gly Phe Val Ala Ala Lys Met Met Glu Ser Val Glu
175                 180                 185                 190 ctg cag gga caa gtg cga aac ctc ttc gtt tac aca tcg ctg ttc atc      624
Leu Gln Gly Gln Val Arg Asn Leu Phe Val Tyr Thr Ser Leu Phe Ile
                195                 200                 205 aaa acg cgg atc cgc aac aac tgg aag gaa cac aat cgg agc tgg gac      672
Lys Thr Arg Ile Arg Asn Asn Trp Lys Glu His Asn Arg Ser Trp Asp
            210                 215                 220 gac ttc atg aca ctc gga aaa caa atg aaa gag gac tac gaa cga gca      720
Asp Phe Met Thr Leu Gly Lys Gln Met Lys Glu Asp Tyr Glu Arg Ala
            225                 230                 235 gaa gct gaa aaa gtg gga cgc cgg aag cag aac aga cgg tgg tcg atg      768
Glu Ala Glu Lys Val Gly Arg Arg Lys Gln Asn Arg Arg Trp Ser Met
    240                 245                 250 att ggc gct gga gta aca gct gga gcc att gga atc gtt gga gtc gtc      816
Ile Gly Ala Gly Val Thr Ala Gly Ala Ile Gly Ile Val Gly Val Val
255                 260                 265                 270 gtg tgt ggg cgg atg atg ttc agc ttg aag taacgtattc aatttgtgta       866
Val Cys Gly Arg Met Met Phe Ser Leu Lys
                275                 280 aataattaat ttatgtacaa ctccttacat ttgaatctca ttttkgctca ctgattctct    926
catcctttga actggaagaa gtgggaaagc taggccacaa attacggctc tctgtgtcga    986
tttacgattt tactgcaatt ttttccgatt gcctttttt ttggccaaac cctacttccg    1046
cgtaatatca acttttccgt gttctgtaca tttcgtcaaa aaccctgaaa ccctaacttt    1106
tctcgccgtg gcctagcctc ccgcttctct tccacatttc caaagtaccc ctgtatctca    1166
ataattcatc ttcactttaa ctgtctcttt tcgtgtggcc tcttccaact ccccccaaat    1226
tcctgtacgc gtacgcgact ttgtatttat tttttttcaaa ttgttttctc tctacaacaa    1286
```
caaaaaaaac ggttcaaaaa aaaaaaaaa                          1315

<210> SEQ ID NO 3
<211> LENGTH: 280
<212> TYPE: PRT
<213> ORGANISM: Caenorrhabditis elegans

<400> SEQUENCE: 3

Met Thr Arg Cys Thr Ala Asp Asn Ser Leu Thr Asn Pro Ala Tyr Arg
 1               5                  10                  15

Arg Arg Thr Met Ala Thr Gly Glu Met Lys Glu Phe Leu Gly Ile Lys
            20                  25                  30

Gly Thr Glu Pro Thr Asp Phe Gly Ile Asn Ser Asp Ala Gln Asp Leu
        35                  40                  45

Pro Ser Pro Ser Arg Gln Ala Ser Thr Arg Arg Met Ser Ile Gly Glu
    50                  55                  60

Ser Ile Asp Gly Lys Ile Asn Asp Trp Glu Pro Arg Leu Asp Ile
65                  70                  75                  80

Glu Gly Phe Val Val Asp Tyr Phe Thr His Arg Ile Arg Gln Asn Gly
                85                  90                  95

Met Glu Trp Phe Gly Ala Pro Gly Leu Pro Cys Gly Val Gln Pro Glu
            100                 105                 110

His Glu Met Met Arg Val Met Gly Thr Ile Phe Glu Lys Lys His Ala
        115                 120                 125

Glu Asn Phe Glu Thr Phe Cys Glu Gln Leu Leu Ala Val Pro Arg Ile
    130                 135                 140

Ser Phe Ser Leu Tyr Gln Asp Val Val Arg Thr Val Gly Asn Ala Gln
145                 150                 155                 160

Thr Asp Gln Cys Pro Met Ser Tyr Gly Arg Leu Ile Gly Leu Ile Ser
                165                 170                 175

Phe Gly Gly Phe Val Ala Ala Lys Met Met Glu Ser Val Glu Leu Gln
            180                 185                 190

Gly Gln Val Arg Asn Leu Phe Val Tyr Thr Ser Leu Phe Ile Lys Thr
        195                 200                 205

Arg Ile Arg Asn Asn Trp Lys Glu His Asn Arg Ser Trp Asp Asp Phe
    210                 215                 220

Met Thr Leu Gly Lys Gln Met Lys Glu Asp Tyr Glu Arg Ala Glu Ala
225                 230                 235                 240

Glu Lys Val Gly Arg Arg Lys Gln Asn Arg Arg Trp Ser Met Ile Gly
                245                 250                 255

Ala Gly Val Thr Ala Gly Ala Ile Gly Ile Val Gly Val Val Cys
            260                 265                 270

Gly Arg Met Met Phe Ser Leu Lys
        275                 280

<210> SEQ ID NO 4
<211> LENGTH: 1315
<212> TYPE: DNA
<213> ORGANISM: Caenorrhabditis elegans
<220> FEATURE:
<221> NAME/KEY: CDS
<222> LOCATION: (7)...(846)

<400> SEQUENCE: 4 tttgag atg aca cgc tgc acg gcg gac aac tcg ctg acg aat ccg gcg    48
       Met Thr Arg Cys Thr Ala Asp Asn Ser Leu Thr Asn Pro Ala
        1               5                  10

```
                                                                -continued tat cgg cga cga acg atg gcg act ggc gag atg aag gag ttt ctg ggg        96
Tyr Arg Arg Arg Thr Met Ala Thr Gly Glu Met Lys Glu Phe Leu Gly
 15              20                  25                  30 ata aaa ggc aca gag ccc acc gat ttt gga atc aat agt gat gct cag       144
Ile Lys Gly Thr Glu Pro Thr Asp Phe Gly Ile Asn Ser Asp Ala Gln
             35                  40                  45 gac ttg cca tca ccg agt agg cag gct tcg acg cga aga atg tcc atc       192
Asp Leu Pro Ser Pro Ser Arg Gln Ala Ser Thr Arg Arg Met Ser Ile
         50                  55                  60 gga gag tca att gat gga aaa atc aat gat tgg gaa gag cca agg ctt       240
Gly Glu Ser Ile Asp Gly Lys Ile Asn Asp Trp Glu Glu Pro Arg Leu
             65                  70                  75 gat atc gag gga ttt gtg gtc gac tat ttc acg cac cga atc cgg caa       288
Asp Ile Glu Gly Phe Val Val Asp Tyr Phe Thr His Arg Ile Arg Gln
 80                  85                  90 aac gga atg gaa tgg ttt gga gca ccg gga ttg ccg tgt gga gtg caa       336
Asn Gly Met Glu Trp Phe Gly Ala Pro Gly Leu Pro Cys Gly Val Gln
 95                 100                 105                 110 ccg gag cac gaa atg atg cga gtt atg gga acg ata ttc gag aag aag       384
Pro Glu His Glu Met Met Arg Val Met Gly Thr Ile Phe Glu Lys Lys
                115                 120                 125 cac gcg gaa aat ttt gag acc ttc tgt gag cag ctg ctc gca gtg ccc       432
His Ala Glu Asn Phe Glu Thr Phe Cys Glu Gln Leu Leu Ala Val Pro
            130                 135                 140 aga atc tca ttt tca ctg aat cag gat gtg gtt cgg acg gtt gga aat       480
Arg Ile Ser Phe Ser Leu Asn Gln Asp Val Val Arg Thr Val Gly Asn
        145                 150                 155 gca cag aca gat caa tgt cca atg tct tat gga cgt ttg ata ggt cta       528
Ala Gln Thr Asp Gln Cys Pro Met Ser Tyr Gly Arg Leu Ile Gly Leu
160                 165                 170 atc tcg ttc ggc ggt ttc gta gct gca aaa atg atg gaa tcc gtg gaa       576
Ile Ser Phe Gly Gly Phe Val Ala Ala Lys Met Met Glu Ser Val Glu
175                 180                 185                 190 ctg cag gga caa gtg cga aac ctc ttc gtt tac aca tcg ctg ttc atc       624
Leu Gln Gly Gln Val Arg Asn Leu Phe Val Tyr Thr Ser Leu Phe Ile
                195                 200                 205 aaa acg cgg atc cgc aac aac tgg aag gaa cac aat cgg agc tgg gac       672
Lys Thr Arg Ile Arg Asn Asn Trp Lys Glu His Asn Arg Ser Trp Asp
            210                 215                 220 gac ttc atg aca ctc gga aaa caa atg aaa gag gac tac gaa cga gca       720
Asp Phe Met Thr Leu Gly Lys Gln Met Lys Glu Asp Tyr Glu Arg Ala
        225                 230                 235 gaa gct gaa aaa gtg gga cgc cgg aag cag aac aga cgg tgg tcg atg       768
Glu Ala Glu Lys Val Gly Arg Arg Lys Gln Asn Arg Arg Trp Ser Met
240                 245                 250 att ggc gct gga gta aca gct gga gcc att gga atc gtt gga gtc gtc       816
Ile Gly Ala Gly Val Thr Ala Gly Ala Ile Gly Ile Val Gly Val Val
255                 260                 265                 270 gtg tgt ggg cgg atg atg ttc agc ttg aag taacgtattc aatttgtgta         866
Val Cys Gly Arg Met Met Phe Ser Leu Lys
                275                 280 aataattaat ttatgtacaa ctccttacat ttgaatctca ttttkgctca ctgattctct     926
catcctttga actggaagaa gtgggaaagc taggccacaa attacggctc tctgtgtcga     986
tttacgattt tactgcaatt ttttccgatt gcctttttt ttggccaaac cctacttccg     1046
cgtaatatca acttttccgt gttctgtaca tttcgtcaaa aaccctgaaa ccctaacttt    1106
tctcgccgtg gcctagcctc ccgcttctct tccacatttc caaagtaccc ctgtatctca    1166
ataattcatc ttcactttaa ctgtctcttt tcgtgtggcc tcttccaact cccccccaaat   1226
```

-continued

```
tcctgtacgc gtacgcgact ttgtatttat tttttcaaa ttgttttctc tctacaacaa      1286
caaaaaaaac ggttcaaaaa aaaaaaaaa                                        1315
```

<210> SEQ ID NO 5
<211> LENGTH: 1315
<212> TYPE: DNA
<213> ORGANISM: Caenorrhabditis elegans
<220> FEATURE:
<221> NAME/KEY: CDS
<222> LOCATION: (7)...(846)

<400> SEQUENCE: 5

```
tttgag atg aca cgc tgc acg gcg gac aac tcg ctg acg aat ccg gcg          48
       Met Thr Arg Cys Thr Ala Asp Asn Ser Leu Thr Asn Pro Ala
       1               5                  10 tat cgg cga cga acg atg gcg act ggc gag atg aag gag ttt ctg ggg         96
Tyr Arg Arg Arg Thr Met Ala Thr Gly Glu Met Lys Glu Phe Leu Gly
15                  20                  25                  30 ata aaa ggc aca gag ccc acc gat ttt gga atc aat agt gat gct cag        144
Ile Lys Gly Thr Glu Pro Thr Asp Phe Gly Ile Asn Ser Asp Ala Gln
                35                  40                  45 gac ttg cca tca ccg agt agg cag gct tcg acg cga aga atg tcc atc        192
Asp Leu Pro Ser Pro Ser Arg Gln Ala Ser Thr Arg Arg Met Ser Ile
        50                  55                  60 gga gag tca att gat gga aaa atc aat gat tgg gaa gag cca agg ctt        240
Gly Glu Ser Ile Asp Gly Lys Ile Asn Asp Trp Glu Glu Pro Arg Leu
65                  70                  75 gat atc gag gga ttt gtg gtc gac tat ttc acg cac cga atc cgg caa        288
Asp Ile Glu Gly Phe Val Val Asp Tyr Phe Thr His Arg Ile Arg Gln
            80                  85                  90 aac gga atg gaa tgg ttt gga gca ccg gga ttg ccg tgt gga gtg caa        336
Asn Gly Met Glu Trp Phe Gly Ala Pro Gly Leu Pro Cys Gly Val Gln
95                  100                 105                 110 ccg gag cac gaa atg atg cga gtt atg gga acg ata ttc gag aag aag        384
Pro Glu His Glu Met Met Arg Val Met Gly Thr Ile Phe Glu Lys Lys
                115                 120                 125 cac gcg gaa aat ttt gag acc ttc tgt gag cag ctg ctc gca gtg ccc        432
His Ala Glu Asn Phe Glu Thr Phe Cys Glu Gln Leu Leu Ala Val Pro
        130                 135                 140 aga atc tca ttt tca ctg tat cag gat gtg gtt cgg acg gtt gga aat        480
Arg Ile Ser Phe Ser Leu Tyr Gln Asp Val Val Arg Thr Val Gly Asn
145                 150                 155 gca tag aca gat caa tgt cca atg tct tat gga cgt ttg ata ggt cta        528
Ala  *  Thr Asp Gln Cys Pro Met Ser Tyr Gly Arg Leu Ile Gly Leu
            160                 165                 170 atc tcg ttc ggc ggt ttc gta gct gca aaa atg atg gaa tcc gtg gaa        576
Ile Ser Phe Gly Gly Phe Val Ala Ala Lys Met Met Glu Ser Val Glu
175                 180                 185 ctg cag gga caa gtg cga aac ctc ttc gtt tac aca tcg ctg ttc atc        624
Leu Gln Gly Gln Val Arg Asn Leu Phe Val Tyr Thr Ser Leu Phe Ile
190                 195                 200                 205 aaa acg cgg atc cgc aac aac tgg aag gaa cac aat cgg agc tgg gac        672
Lys Thr Arg Ile Arg Asn Asn Trp Lys Glu His Asn Arg Ser Trp Asp
                210                 215                 220 gac ttc atg aca ctc gga aaa caa atg aaa gag gac tac gaa cga gca        720
Asp Phe Met Thr Leu Gly Lys Gln Met Lys Glu Asp Tyr Glu Arg Ala
        225                 230                 235 gaa gct gaa aaa gtg gga cgc cgg aag cag aac aga cgg tgg tcg atg        768
Glu Ala Glu Lys Val Gly Arg Arg Lys Gln Asn Arg Arg Trp Ser Met
240                 245                 250
```

-continued

```
att ggc gct gga gta aca gct gga gcc att gga atc gtt gga gtc gtc        816
Ile Gly Ala Gly Val Thr Ala Gly Ala Ile Gly Ile Val Gly Val Val
    255                 260                 265 gtg tgt ggg cgg atg atg ttc agc ttg aag taacgtattc aatttgtgta          866
Val Cys Gly Arg Met Met Phe Ser Leu Lys
270                 275 aataattaat ttatgtacaa ctccttacat ttgaatctca ttttkgctca ctgattctct       926
catcctttga actggaagaa gtgggaaagc taggccacaa attacggctc tctgtgtcga       986
tttacgattt tactgcaatt ttttccgatt gcctttttt ttggccaaac cctacttccg       1046
cgtaatatca acttttccgt gttctgtaca tttcgtcaaa aaccctgaaa ccctaacttt      1106
tctcgccgtg gcctagcctc ccgcttctct tccacatttc caaagtaccc ctgtatctca      1166
ataattcatc ttcactttaa ctgtctcttt tcgtgtggcc tcttccaact cccccaaat      1226 tcctgtacgc gtacgcgact ttgtatttat tttttcaaa ttgttttctc tctacaacaa      1286
caaaaaaaac ggttcaaaaa aaaaaaaaa                                         1315

<210> SEQ ID NO 6
<211> LENGTH: 1315
<212> TYPE: DNA
<213> ORGANISM: Caenorrhabditis elegans
<220> FEATURE:
<221> NAME/KEY: CDS
<222> LOCATION: (7)...(846)

<400> SEQUENCE: 6 tttgag atg aca cgc tgc acg gcg gac aac tcg ctg acg aat ccg gcg         48
       Met Thr Arg Cys Thr Ala Asp Asn Ser Leu Thr Asn Pro Ala
         1               5                  10 tat cgg cga cga acg atg gcg act ggc gag atg aag gag ttt ctg ggg        96
Tyr Arg Arg Arg Thr Met Ala Thr Gly Glu Met Lys Glu Phe Leu Gly
 15                  20                  25                  30 ata aaa ggc aca gag ccc acc gat ttt gga atc aat agt gat gct cag       144
Ile Lys Gly Thr Glu Pro Thr Asp Phe Gly Ile Asn Ser Asp Ala Gln
             35                  40                  45 gac ttg cca tca ccg agt agg cag gct tcg acg cga aga atg tcc atc       192
Asp Leu Pro Ser Pro Ser Arg Gln Ala Ser Thr Arg Arg Met Ser Ile
         50                  55                  60 gga gag tca att gat gga aaa atc aat gat tgg gaa gag cca agg ctt       240
Gly Glu Ser Ile Asp Gly Lys Ile Asn Asp Trp Glu Glu Pro Arg Leu
     65                  70                  75 gat atc gag gga ttt gtg gtc gac tat ttc acg cac cga atc cgg caa       288
Asp Ile Glu Gly Phe Val Val Asp Tyr Phe Thr His Arg Ile Arg Gln
 80                  85                  90 aac gga atg gaa tgg ttt gga gca ccg gga ttg ccg tgt gga gtg caa       336
Asn Gly Met Glu Trp Phe Gly Ala Pro Gly Leu Pro Cys Gly Val Gln
 95                 100                 105                 110 ccg gag cac gaa atg atg cga gtt atg gga acg ata ttc gag aag aag       384
Pro Glu His Glu Met Met Arg Val Met Gly Thr Ile Phe Glu Lys Lys
            115                 120                 125 cac gcg gaa aat ttt gag acc ttc tgt gag cag ctg ctc gca gtg ccc       432
His Ala Glu Asn Phe Glu Thr Phe Cys Glu Gln Leu Leu Ala Val Pro
        130                 135                 140 aga atc tca ttt tca ctg tat cag gat gtg gtt cgg acg gtt gga aat       480
Arg Ile Ser Phe Ser Leu Tyr Gln Asp Val Val Arg Thr Val Gly Asn
    145                 150                 155 gca cag aca gat caa tgt cca atg tct tat gaa cgt ttg ata ggt cta       528
Ala Gln Thr Asp Gln Cys Pro Met Ser Tyr Glu Arg Leu Ile Gly Leu
160                 165                 170
```

```
atc tcg ttc ggc ggt ttc gta gct gca aaa atg atg gaa tcc gtg gaa    576
Ile Ser Phe Gly Gly Phe Val Ala Ala Lys Met Met Glu Ser Val Glu
175                 180                 185                 190 ctg cag gga caa gtg cga aac ctc ttc gtt tac aca tcg ctg ttc atc    624
Leu Gln Gly Gln Val Arg Asn Leu Phe Val Tyr Thr Ser Leu Phe Ile
            195                 200                 205 aaa acg cgg atc cgc aac aac tgg aag gaa cac aat cgg agc tgg gac    672
Lys Thr Arg Ile Arg Asn Asn Trp Lys Glu His Asn Arg Ser Trp Asp
        210                 215                 220 gac ttc atg aca ctc gga aaa caa atg aaa gag gac tac gaa cga gca    720
Asp Phe Met Thr Leu Gly Lys Gln Met Lys Glu Asp Tyr Glu Arg Ala
    225                 230                 235 gaa gct gaa aaa gtg gga cgc cgg aag cag aac aga cgg tgg tcg atg    768
Glu Ala Glu Lys Val Gly Arg Arg Lys Gln Asn Arg Arg Trp Ser Met
240                 245                 250 att ggc gct gga gta aca gct gga gcc att gga atc gtt gga gtc gtc    816
Ile Gly Ala Gly Val Thr Ala Gly Ala Ile Gly Ile Val Gly Val Val
255                 260                 265                 270 gtg tgt ggg cgg atg atg ttc agc ttg aag taacgtattc aatttgtgta      866
Val Cys Gly Arg Met Met Phe Ser Leu Lys
                275                 280 aataattaat ttatgtacaa ctccttacat ttgaatctca ttttkgctca ctgattctct   926
catcctttga actggaagaa gtgggaaagc taggccacaa attacggctc tctgtgtcga   986
tttacgattt tactgcaatt ttttccgatt gccttttttt ttggccaaac cctacttccg  1046
cgtaatatca acttttccgt gttctgtaca tttcgtcaaa aaccctgaaa ccctaacttt  1106
tctcgccgtg gcctagcctc ccgcttctct tccacatttc caaagtaccc ctgtatctca  1166
ataattcatc ttcactttaa ctgtctcttt tcgtgtggcc tcttccaact cccccaaat   1226
tcctgtacgc gtacgcgact ttgtatttat tttttcaaa ttgttttctc tctacaacaa   1286
caaaaaaac ggttcaaaaa aaaaaaaaa                                     1315
```

<210> SEQ ID NO 7
<211> LENGTH: 5086
<212> TYPE: DNA
<213> ORGANISM: Homo sapiens
<220> FEATURE:
<221> NAME/KEY: CDS
<222> LOCATION: (1459)...(2178)

<400> SEQUENCE: 7

```
gcgcccgccc ctccgcgccg cctgcccgcc cgcccgccgc gctcccgccc gccgctctcc    60
gtggccccgc cgcgctgccg ccgccgccgc tgccagcgaa ggtgccgggg ctccgggccc   120
tccctgccgg cggccgtcag cgctcggagc gaactgcgcg acgggaggtc cgggaggcga   180
ccgtagtcgc gccgccgcgc aggaccagga ggaggagaaa gggtgcgcag cccggaggcg   240
gggtgcgccg gtggggtgca gcggaagagg gggtccaggg gggagaactt cgtagcagtc   300
atccttttta ggaaaagagg gaaaaaataa aaccctcccc caccacctcc ttctccccac   360
ccctcgccgc accacacaca gcgcgggctt ctagcgctcg gcaccggcgg gccaggcgcg   420
tcctgccttc atttatccag cagcttttcg gaaaatgcat ttgctgttcg gagtttaatc   480
agaagacgat tcctgcctcc gtccccggct ccttcatcgt cccatctccc ctgtctctct   540
cctggggagg cgtgaagcgg tcccgtggat agagattcat gcctgtgtcc gcgcgtgtgt   600
gcgcgcgtat aaattgccga aaggggaaa acatcacagg acttctgcga ataccggact    660
gaaaattgta attcatctgc cgccgccgct gccaaaaaaa aactcgagct cttgagatct   720
```

```
ccggttggga ttcctgcgga ttgacatttc tgtgaagcag aagtctggga atcgatctgg    780
aaatcctcct aattttact ccctctcccc ccgactcctg attcattggg aagtttcaaa    840
tcagctataa ctggagagtg ctgaagattg atgggatcgt tgccttatgc atttgttttg    900
gttttacaaa aaggaaactt gacagaggat catgctgtac ttaaaaaata caagtaagtc    960
tcgcacagga aattggttta atgtaacttt caatggaaac ctttgagatt ttttacttaa   1020
agtgcattcg agtaaattta atttccaggc agcttaatac attgtttta gccgtgttac   1080 ttgtagtgtg tatgccctgc tttcactcag tgtgtacagg gaaacgcacc tgattttta   1140 cttattagtt tgttttttct taacctttc agcatcacag aggaagtaga ctgatattaa   1200
caatacttac taataataac gtgcctcatg aaataaagat ccgaaaggaa ttggaataaa   1260
aatttcctgc gtctcatgcc aagagggaaa caccagaatc aagtgttccg cgtgattgaa   1320 gacacccct cgtccaagaa tgcaaagcac atccaataaa atagctggat tataactcct   1380
cttctttctc tgggggccgt ggggtgggag ctggggcgag aggtgccgtt ggccccgtt    1440
```
gcttttcctc tgggaagg atg gcg cac gct ggg aga acg ggg tac gac aac    1491
                             Met Ala His Ala Gly Arg Thr Gly Tyr Asp Asn
                              1               5                10 cgg gag ata gtg atg aag tac atc cat tat aag ctg tcg cag agg ggc    1539
Arg Glu Ile Val Met Lys Tyr Ile His Tyr Lys Leu Ser Gln Arg Gly
         15               20                25 tac gag tgg gat gcg gga gat gtg ggc gcc gcg ccc ccg ggg gcc gcc    1587
Tyr Glu Trp Asp Ala Gly Asp Val Gly Ala Ala Pro Pro Gly Ala Ala
       30               35               40 ccc gca ccg ggc atc ttc tcc tcc cag ccc ggg cac acg ccc cat cca    1635
Pro Ala Pro Gly Ile Phe Ser Ser Gln Pro Gly His Thr Pro His Pro
 45                50               55 gcc gca tcc cgc gac ccg gtc gcc agg acc tcg ccg ctg cag acc ccg    1683
Ala Ala Ser Arg Asp Pro Val Ala Arg Thr Ser Pro Leu Gln Thr Pro
 60                65              70              75 gct gcc ccc ggc gcc gcc gcg ggg cct gcg ctc agc ccg gtg cca cct    1731
Ala Ala Pro Gly Ala Ala Ala Gly Pro Ala Leu Ser Pro Val Pro Pro
                 80                85              90 gtg gtc cac ctg gcc ctc cgc caa gcc ggc gac gac ttc tcc cgc cgc    1779
Val Val His Leu Ala Leu Arg Gln Ala Gly Asp Asp Phe Ser Arg Arg
         95              100              105 tac cgc ggc gac ttc gcc gag atg tcc agc cag ctg cac ctg acg ccc    1827
Tyr Arg Gly Asp Phe Ala Glu Met Ser Ser Gln Leu His Leu Thr Pro
      110             115              120 ttc acc gcg cgg gga cgc ttt gcc acg gtg gtg gag gag ctc ttc agg    1875
Phe Thr Ala Arg Gly Arg Phe Ala Thr Val Val Glu Glu Leu Phe Arg
125                130                135 gac ggg gtg aac tgg ggg agg att gtg gcc ttc ttt gag ttc ggt ggg    1923
Asp Gly Val Asn Trp Gly Arg Ile Val Ala Phe Phe Glu Phe Gly Gly
140                145              150             155 gtc atg tgt gtg gag agc gtc aac cgg gag atg tcg ccc ctg gtg gac    1971
Val Met Cys Val Glu Ser Val Asn Arg Glu Met Ser Pro Leu Val Asp
                160              165             170 aac atc gcc ctg tgg atg act gag tac ctg aac cgg cac ctg cac acc    2019
Asn Ile Ala Leu Trp Met Thr Glu Tyr Leu Asn Arg His Leu His Thr
        175             180              185 tgg atc cag gat aac gga ggc tgg gat gcc ttt gtg gaa ctg tac ggc    2067
Trp Ile Gln Asp Asn Gly Gly Trp Asp Ala Phe Val Glu Leu Tyr Gly
               190              195             200 ccc agc atg cgg cct ctg ttt gat ttc tcc tgg ctg tct ctg aag act    2115
Pro Ser Met Arg Pro Leu Phe Asp Phe Ser Trp Leu Ser Leu Lys Thr -continued

```
            205                 210                 215
ctg ctc agt ttg gcc ctg gtg gga gct tgc atc acc ctg ggt gcc tat    2163
Leu Leu Ser Leu Ala Leu Val Gly Ala Cys Ile Thr Leu Gly Ala Tyr
220                 225                 230                 235 ctg agc cac aag tga agtcaacatg cctgcccaa acaaatatgc aaaaggttca     2218
Leu Ser His Lys  * ctaaagcagt agaataata tgcattgtca gtgatgtacc atgaaacaaa gctgcaggct   2278
gtttaagaaa aataacaca catataaaca tcacacacac agacagacac acacacacac   2338
aacaattaac agtcttcagg caaaacgtcg aatcagctat ttactgccaa agggaaatat  2398
catttatttt ttacattatt aagaaaaaag atttatttat ttaagacagt cccatcaaaa  2458
ctccgtcttt ggaaatccga ccactaattg ccaaacaccg cttcgtgtgg ctccacctgg  2518
atgttctgtg cctgtaaaca tagattcgct ttccatgttg ttggccggat caccatctga  2578
agagcagacg gatggaaaaa ggacctgatc attgggaag ctggctttct ggctgctgga   2638
ggctggggag aaggtgttca ttcacttgca tttcttgcc ctgggggcgt gatattaaca   2698
gagggagggt tcccgtgggg ggaagtccat gcctccctgg cctgaagaag agactctttg  2758
catatgactc acatgatgca tacctggtgg gaggaaaaga gttgggaact tcagatggac  2818
ctagtaccca ctgagatttc cacgccgaag gacagcgatg ggaaaaatgc ccttaaatca  2878
taggaaagta ttttttaag ctaccaattg tgccgagaaa agcattttag caatttatac   2938
aatatcatcc agtaccttaa accctgattg tgtatattca tatattttgg atacgcaccc  2998
cccaactccc aatactggct ctgtctgagt aagaaacaga atcctctgga acttgaggaa  3058
gtgaacattt cggtgacttc cgatcaggaa ggctagagtt acccagagca tcaggccgcc  3118
acaagtgcct gcttttagga gaccgaagtc cgcagaacct acctgtgtcc cagcttggag  3178
gcctggtcct ggaactgagc cgggccctca ctggcctcct ccaggatga tcaacagggt   3238
agtgtggtct ccgaatgtct ggaagctgat ggatggagct cagaattcca ctgtcaagaa  3298
agagcagtag agggtgtgg ctgggcctgt caccctgggg ccctccaggt aggcccgttt   3358
tcacgtggag cataggagcc acgacccttc ttaagacatg tatcactgta gagggaagga  3418
acagaggccc tgggccttcc tatcagaagg acatggtgaa ggctgggaac gtgaggagag  3478
gcaatggcca cggcccattt tggctgtagc acatggcacg ttggctgtgt ggccttggcc  3538
acctgtgagt ttaaagcaag gctttaaatg actttggaga gggtcacaaa tcctaaaaga  3598
agcattgaag tgaggtgtca tggattaatt gacccctgtc tatggaatta catgtaaaac  3658
attatcttgt cactgtagtt tggttttatt tgaaaacctg acaaaaaaaa agttccaggt  3718
gtggaatatg ggggttatct gtacatcctg ggcattaaa aaaaaatcaa tggtggggaa   3778
ctataaagaa gtaacaaaag aagtgacatc ttcagcaaat aaactaggaa atttttttt   3838
cttccagttt agaatcagcc ttgaaacatt gatggaataa ctctgtggca ttattgcatt  3898
ataccatt tatctgtatt aactttggaa tgtactctgt tcaatgtta atgctgtggt    3958
tgatatttcg aaagctgctt taaaaaata catgcatctc agcgttttt tgtttttaat    4018
tgtatttagt tatggcctat acactatttg tgagcaaagg tgatcgtttt ctgtttgaga  4078
tttttatctc ttgattcttc aaaagcattc tgagaaggtg agataagccc tgagtctcag  4138
ctacctaaga aaaacctgga tgtcactggc cactgaggag ctttgtttca accaagtcat  4198
gtgcatttcc acgtcaacag aattgtttat tgtgacagtt atatctgttg tcccttttgac 4258
cttgtttctt gaaggttttcc tcgtccctgg gcaattccgc atttaattca tggtattcag 4318
```

```
gattacatgc atgtttggtt aaacccatga gattcattca gttaaaaatc cagatggcga    4378
atgaccagca gattcaaatc tatggtggtt tgacctttag agagttgctt tacgtggcct    4438
gtttcaacac agacccaccc agagccctcc tgccctcctt ccgcggggc tttctcatgg     4498 ctgtccttca gggtcttcct gaaatgcagt ggtcgttacg ctccaccaag aaagcaggaa    4558
acctgtggta tgaagccaga cctccccggc gggcctcagg gaacagaatg atcagacctt    4618
tgaatgattc taatttttaa gcaaaatatt attttatgaa aggtttacat tgtcaaagtg    4678
atgaatatgg aatatccaat cctgtgctgc tatcctgcca aaatcatttt aatgagtca    4738 gtttgcagta tgctccacgt ggtaagatcc tccaagctgc tttagaagta acaatgaaga    4798
acgtggacgt ttttaatata aagcctgttt tgtcttttgt tgttgttcaa acgggattca    4858
cagagtattt gaaaaatgta tatatattaa gaggtcacgg gggctaattg ctagctggct    4918 gcctttgct gtggggtttt gttacctggt tttaataaca gtaaatgtgc ccagcctctt     4978
ggccccagaa ctgtacagta ttgtggctgc acttgctcta agagtagttg atgttgcatt    5038
ttccttattg ttaaaaacat gttagaagca atgaatgtat ataaaagc                 5086
```

<210> SEQ ID NO 8
<211> LENGTH: 239
<212> TYPE: PRT
<213> ORGANISM: Homo sapiens

<400> SEQUENCE: 8

```
Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Ala
                85                  90                  95

Leu Arg Gln Ala Gly Asp Asp Phe Ser Arg Arg Tyr Arg Gly Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Ser His Lys
225                 230                 235
```

What is claimed is:

1. An isolated polypeptide comprising the amino acid sequence set forth in SEQ ID NO:3, wherein said polypeptide functions to protect cells against cell death.

2. An isolated polypeptide comprising the amino acid sequence set forth in SEQ ID NO:3 having a glycine to glutamic acid substitution at amino acid position 169, wherein said polypeptide functions to protect cells against cell death.

3. An isolated polypeptide comprising the amino acid sequence set forth in SEQ ID NO: 3, wherein said polypeptide contains a change selected from:

a) a tyrosine to asparagine substitution at amino acid 149 of SEQ ID NO: 3; and b) a truncated carboxy terminus, wherein the carboxy-terminal amino acid is glutamine 160 of SEQ ID NO: 3, and wherein said change inactivates said polypeptide, and wherein said polypeptide does not protect cells against cell death.

4. The protein of claim 1, 2, or 3, wherein said protein is from *C. elegans*.

* * * * *

UNITED STATES PATENT AND TRADEMARK OFFICE
CERTIFICATE OF CORRECTION

PATENT NO. : 6,465,617 B1
DATED : October 15, 2002
INVENTOR(S) : Horvitz et al.

It is certified that error appears in the above-identified patent and that said Letters Patent is hereby corrected as shown below:

Item [56], References Cited, OTHER PUBLICATIONS, reference, "Sentman et al.", replace "Selectrion" with -- Selection --; and reference, "Seto et al.", replace "Bci-2-1g" with -- Bcl-2-1g --.

Column 4,
Line 67, replace "constituatively" with -- constitutively --.

Column 13,
Line 13, replace "apoptic" with -- apoptotic --.

Column 17,
Line 27, replace "ingestion.," with -- ingestion, --.

Column 25,
Line 14, replace "n487sd. ts" with -- n487sd, ts --; and
Line 37, replace "numaber" with -- number --.

Signed and Sealed this

Twenty-fourth Day of August, 2004

JON W. DUDAS
*Director of the United States Patent and Trademark Office*